US011723348B2

(12) United States Patent
Shen et al.

(10) Patent No.: US 11,723,348 B2
(45) **Date of Patent: *Aug. 15, 2023**

(54) GENETICALLY MODIFIED MICE EXPRESSING HUMANIZED CD47

(71) Applicant: Biocytogen Pharmaceuticals (Beijing) Co., Ltd., Beijing (CN)

(72) Inventors: Yuelei Shen, Beijing (CN); Yang Bai, Beijing (CN); Jian Ni, Beijing (CN); Rui Huang, Beijing (CN); Chengzhang Shang, Beijing (CN); Yanan Guo, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 315 days.

This patent is subject to a terminal disclaimer.

(21) Appl. No.: 17/087,487

(22) Filed: Nov. 2, 2020

(65) Prior Publication Data

US 2021/0120790 A1 Apr. 29, 2021

Related U.S. Application Data

(60) Division of application No. 16/435,368, filed on Jun. 7, 2019, now Pat. No. 10,918,095, which is a continuation of application No. PCT/CN2018/081628, filed on Apr. 2, 2018.

(30) Foreign Application Priority Data

Mar. 31, 2017 (CN) ......................... 201710205646.7
Oct. 27, 2017 (CN) ......................... 201711039543.4

(51) Int. Cl.
*A01K 67/027* (2006.01)

(52) U.S. Cl.
CPC ...... *A01K 67/0278* (2013.01); *A01K 2207/15* (2013.01); *A01K 2217/072* (2013.01); *A01K 2227/105* (2013.01); *A01K 2267/03* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 7,145,055 | B2 | 12/2006 | Ito et al. |
| 7,381,560 | B2 | 6/2008 | Anderson et al. |
| 10,820,580 | B2 | 11/2020 | Shen et al. |
| 10,918,095 | B2 * | 2/2021 | Shen ................ G01N 33/57492 |
| 10,973,212 | B2 * | 4/2021 | Shen .................... C07K 14/705 |
| 2015/0106961 | A1 | 4/2015 | Rojas et al. |
| 2016/0295844 | A1 | 10/2016 | Herndler-Brandstetter et al. |
| 2016/0345549 | A1 * | 12/2016 | Gurer ................. G01N 33/5011 |
| 2019/0320631 | A1 | 10/2019 | Shen et al. |
| 2019/0343097 | A1 | 11/2019 | Shen |
| 2019/0373867 | A1 | 12/2019 | Shent |
| 2021/0105982 | A1 | 4/2021 | Shen et al. |

FOREIGN PATENT DOCUMENTS

| | | |
|---|---|---|
| CN | 101809156 | 8/2010 |
| CN | 103409468 | 11/2013 |
| CN | 104039821 | 9/2014 |
| CN | 104561095 | 4/2015 |
| CN | 104904661 | 9/2015 |
| CN | 105592695 | 5/2016 |
| CN | 106119284 | 11/2016 |
| CN | 106456749 | 2/2017 |
| CN | 106755115 | 5/2017 |
| CN | 107205368 | 9/2017 |
| CN | 108467873 | 8/2018 |
| CN | 108531487 | 9/2018 |
| CN | 108588126 | 9/2018 |
| CN | 109735498 | 5/2019 |
| WO | WO 200148020 | 7/2001 |
| WO | WO 2007033221 | 3/2007 |
| WO | WO 2010070047 | 6/2010 |
| WO | WO 2012040207 | 3/2015 |
| WO | WO 2015042557 | 3/2015 |
| WO | WO 2015155904 | 10/2015 |
| WO | WO 2016089692 | 5/2016 |
| WO | WO 2016094679 | 6/2016 |
| WO | WO 2016168212 | 10/2016 |
| WO | WO 2016179399 | 11/2016 |
| WO | WO2018001241 | 1/2018 |
| WO | WO2018041118 | 3/2018 |
| WO | WO2018041119 | 3/2018 |
| WO | WO2018041120 | 3/2018 |
| WO | WO2018041121 | 3/2018 |
| WO | WO2018068756 | 4/2018 |
| WO | WO2018086583 | 5/2018 |
| WO | WO2018086594 | 5/2018 |
| WO | WO2018113774 | 6/2018 |

(Continued)

OTHER PUBLICATIONS

Cao et al., “Defective lymphoid development in mice lacking expression of the common cytokine receptor gamma chain,” Immunity, 1995, 2(3):223-38.

Chang et al., “Modeling human severe combined immunodeficiency and correction by CRISPR/Cas9-enhanced gene targeting,” Cell Reports, 2015, 12:1668-1677.

Cheah et al., “Contemporary gene targeting strategies for the novice,” Molecular biotechnology, Dec. 2001, 19(3):297-304.

DiSanto et al., “Lymphoid development in mice with a targeted deletion of the interleukin 2 receptor gamma chain,” Proceedings of the National Academy of Sciences, Jan. 17, 1995, 92(2):377-381.

Disanto et al., “The murine interleukin-2 receptor γ chain gene: Organization, chromosomal localization and expression in the adult thymus,” European journal of immunology, Dec. 1994, 24(12):3014-3018.

(Continued)

*Primary Examiner* — Michael C Wilson
(74) *Attorney, Agent, or Firm* — Fish & Richardson P.C.

(57) ABSTRACT

The present disclosure relates to genetically modified non-human animals that express a human or chimeric (e.g., humanized) CD47, and methods of use thereof.

13 Claims, 41 Drawing Sheets

Specification includes a Sequence Listing.

(56) References Cited

FOREIGN PATENT DOCUMENTS

| | | |
|---|---|---|
| WO | WO2018121787 | 7/2018 |
| WO | WO 2018177441 | 10/2018 |
| WO | WO 2019095358 | 5/2019 |

OTHER PUBLICATIONS

GenBank Accession No. NC_000003.12, "*Homo sapiens* chromosome 3, GRCh38.p13 Primary Assembly," dated May 16, 2021, 3 pages.
GenBank Accession No. NC_000020.11, "*Homo sapiens* chromosome 20, GRCh38.p13 Primary Assembly," Dated May 16, 2021, 3 pages.
GenBank Accession No. NC_000068.7, "*Mus musculus* strain C57BL/6J chromosome 2, GRCm38.p6 C57BL/6J," dated Jun. 24, 2020, 2 pages.
GenBank Accession No. NC_000082.6, "*Mus musculus* strain C57BL/6J chromosome 16, GRCm38.p6 C57BL/6J," dated Jun. 24, 2020, 2 pages.
GenBank Accession No. NC_000086.7, "*Mus musculus* strain C57BL/6J chromosome X, GRCm38.p6 C57BL/6J," dated Jun. 24, 2022, 2 pages.
GenBank Accession No. NM_000206.2, "*Homo sapiens* interleukin 2 receptor subunit gamma (IL2RG), mRNA," dated Sep. 21, 2019, 6 pages.
GenBank Accession No. NM_001777.3, "*Homo sapiens* CD47 molecule (CD47), transcript variant 1, mRNA," dated Apr. 24, 2020, 6 pages.
GenBank Accession No. NM_007547.4, "*Mus musculus* signal-regulatory protein alpha (Sirpa), transcript variant 1, mRNA," dated Jun. 13, 2021, 7 pages.
GenBank Accession No. NM_010581.3, "*Mus musculus* CD47 antigen (Rh-related antigen, integrin-associated signal transducer) (Cd47), transcript variant 4, mRNA," dated Jun. 13, 2021, 4 pages.
GenBank Accession No. NM_013563.4, "*Mus musculus* interleukin 2 receptor, gamma chain (Il2rg), transcript variant a, mRNA," dated Jun. 1, 2021, 4 pages.
GenBank Accession No. NM_080792.2, "*Homo sapiens* signal regulatory protein alpha (Sirpa), transcript variant 3, mRNA," dated May 14, 2019, 7 pages.
GenBank Accession No. NP_000197.1, "cytokine receptor common subunit gamma precursor [*Homo sapiens*]," dated Apr. 19, 2021, 4 pages.
GenBank Accession No. NP_001768.1, "leukocyte surface antigen CD47 isoform 1 precursor [*Homo sapiens*]," dated May 24, 2021, 4 pages.
GenBank Accession No. NP_031573.2, "tyrosine-protein phosphatase non-receptor type substrate 1 isoform 1 precursor [*Mus musculus*]," dated Jun. 13, 2021, 4 pages.
GenBank Accession No. NP_034711.1, "leukocyte surface antigen CD47 isoform 4 precursor [*Mus musculus*]," dated Jun. 13, 2021, 3 pages.
GenBank Accession No. NP_038591.1, "cytokine receptor common subunit gamma isoform a precursor [*Mus musculus*]," dated Jun. 1, 2021, 3 pages.
GenBank Accession No. NP_542970.1, "tyrosine-protein phosphatase non-receptor type substrate 1 isoform 1 precursor [*Homo sapiens*]," dated May 24, 2021, 4 pages.
Henthorn et al., "IL-2Rγ gene microdeletion demonstrates that canine X-linked severe combined immunodeficiency is a homologue of the human disease," Genomics, Sep. 1, 1994, 23(1):69-74.
Hsu et al., "DNA targeting specificity of RNA-guided Cas9 nucleases," Nature biotechnology, Sep. 2013, 31(9):827-832.
International Preliminary Report on Patentability in International Appln. No. PCT/CN2018/079365, dated Sep. 26, 2019, 7 pages.
International Search Report and Written Opinion in International Appln. No. PCT/CN2018/079365, dated Jun. 11, 2018, 11 pages.
International Search Report and Written Opinion in International Appln. No. PCT/CN2020/142546, dated Mar. 26, 2021, 14 pages.
Ishikawa et al., "Development of functional human blood and immune systems in NOD/SCID/IL2 receptor γ chainnull mice," Blood, Sep. 1, 2005, 106(5):1565-1573.
Katano et al., "NOD-Rag2null IL-2Rγnull mice: an alternative to NOG mice for generation of humanized mice," Experimental animals, 2014,63(3):321-330.
Liao et al., "IL-2 family cytokines: new insights into the complex roles of IL-2 as a broad regulator of T helper cell differentiation," Current opinion in immunology, Oct. 1, 2011, 23(5):598-604.
Mou et al., "A novel deletion mutation in IL2RG gene results in X-linked severe combined immunodeficiency with an atypical phenotype," Immunogenetics, Jan. 2017, 69(1):29-38.
Noguchi et al., "Characterization of the human interleukin-2 receptor gamma chain gene," Journal of Biological Chemistiy, Jun. 25, 1993, 268(18):13601-13608.
Noguchi et al., "Interleukin-2 receptor γ chain: a functional component of the interleukin-7 receptor," Science, Dec. 17, 1993, 262(5141):1877-1880.
Ohbo et al., "Modulation of hematopoiesis in mice with a truncated mutant of the interleukin-2 receptor gamma chain," Blood, Feb. 1, 1996, 87(3):956-967.
Shultz et al., "Human cancer growth and therapy in NOD/SCID/IL2Rγnull (NSG) mice," Cold Spring Harbor protocols, Jul. 2014, 2014(7): 16 pages.
Shultz et al., "Human lymphoid and myeloid cell development in NOD/LtSz-scid IL2Rγnull mice engrafted with mobilized human hemopoietic stem cells," The Journal of Immunology, May 15, 2005, 174(10): 14 pages.
UniProt Accession No. P78324, "Tyrosine-protein phosphatase non-receptor type substrate 1," Jun. 2, 2021, 12 pages.
Zhao et al., "Construction of severe combined immunodeficiency mice based on CRISPR/Cas9 technology," Acta Laboratorium Animals Scientia Sinica, 2016, 24(4):339-343 (with English abstract only).
PCT International Preliminary Report on Patentability in International Appln. No PCT/CN2018/081629, dated Oct. 1, 2019, 6 pages.
PCT International Preliminary Report on Patentability in International Appln. No PCT/CN2018/081628, dated Oct. 1, 2019, 6 pages.
Ansell et al., "A phase 1 study of TTI-621, a novel immune checkpoint inhibitor targeting CD47, in patients with relapsed refractory hematologic malignancies," Blood, 2016, 1812.
Auerbach et al., "Establishment and Chimera Analysis of 129/SvEv- and C57BL/6-Derived mouse embryonic stem cell lines," BioTechniques, 2000, 29:1024-1032.
Barclay et al., "The interaction between signal regulatory protein alpha (SIRPa) and CD47: structure, functino, and therapeutic target," The Annual Review of Immunology, 2013, 32:25-50.
Barthold, "Genetically altered mice: phenotypes, no phenotypes, and Faux phenotypes," Genetica, Sep. 2004, 122(1):75-88.
Brevini et al., "No shortcuts to pig embryonic stem cells," Theriogenology, Sep. 2010, 74(4):544-550.
Buta et al. "Reconsidering pluripotency tests: do we still need teratoma assays?," Stem Cell Res., Jul. 2013, 11(1):552-562.
Festing et al., "Revised nomenclature for strain 129 mice," Mammalian Genome, 1999, 10:836.
Garcia-Arocena, "Same Mutation, Different Phenotype?," The Jackson Laboratory, retrieved from URL <https://www.jax.org/news-and-insights/jax-blog/2014/november/same-mutation-different-phenotype#>, Nov. 11, 2014, 5 pages.
GenBank Accession No. AB012693.1, "*Mus musculus* mRNA for CD47, complete cds," Mar. 30, 1998, 3 pages.
GenBank Accession No. BC062197.1, "*Mus musculus* signal-regulatory protein alpha, mRNA (cDNA clone MGC:70224 Image:5368250), complete cds," GenBank, Nov. 13, 2003, 4 pages.
GenBank Accession No. KJ903815.1, "Synthetic construct *Homo sapiens* clone ccsbBroadEn_13209 Sirpa gene, encodes complete protein," GenBank, May 28, 2014, 3 pages.
GenBank Accession No. LN680437.1, "*Homo sapiens* mRNA for CD47," GenBank, Nov. 14, 2014, 2 pages.
Gomez et al. "Derivation of cat embryonic stem-like cells from in vitro-produced blastocysts on homologous and heterologous feeder cells," Theriogenology, Sep. 2010, 74(4):498-515.

(56) References Cited

OTHER PUBLICATIONS

Harms et al., "Mouse Genome Editing Using the CRISPR/Cas System," Curr Protoc Hum Genetics, 2014, 15.7.1-15.7.27.
Heiman-Patterson et al., "Effect of genetic background on phenotype variability in transgenic mouse models of amyotrophic lateral sclerosis: A window of opportunity in the search for genetic modifiers," Amyotrophic Lateral Sclerosis, 2011, 12:79-86.
Hong et al., "Derivation and Characterization of Embryonic Stem Cells Lines Derived from Transgenic Fischer 344 and Dark Agouti Rats," Stem Cells and Development, 2012, 21(9):1571-1586.
Huang et al., "Targeting CD47: the acievements and concerns of current studies on cnacer immunotherapy," Journal of thoracic diseases, 2017, 9(2):E168.
Inagaki et al., "SHPS-1 regulates integrin-mediated cytoskeletal reorganization and cell motility," The Embo Journal, 2000, 19(24):6721-6731.
International Search Report and Written Opinion in International Appln. No. PCT/CN2018/081628, dated Jun. 27, 2018, 12 pages.
International Search Report and Written Opinion in International Appln. No. PCT/CN2018/081629, dated Jun. 27, 2018, 13 pages.
Ito et al., NOD/SCID/ ycnull mouse: an excellent recipient mouse model for engraftment of human cells, Blood, 2002, 100(9):3175-3182.
Ivics et al., "Germline transgenesis in pigs by cytoplasmic microinjection of Sleeping Beauty transposons," Nature Protocols, Apr. 2014, 9(4):810-827.
Legrand et al., "Functional CD47/signal regulatory protein alpha (SIRPa) interaction is required for optimal human T- and natural killer-(NK) cell homeostasis in vivo," PNAS, 2011, 108(32):13224-13229.
Liu et al., "Is CD47 an innate immune checkpoint for tumor evasion?" Journal of hematology & oncology, 2017, 10(1):12.
Liu et al., "Pre-clinical development of a humanized anti-CD47 antibody with anti-cancer therapeutic potential," PloS one, 2015, 10(9):e013745.
Liu, "Strategies for designing transgenic DNA constructs," Methods Mol. Biol., 2013, 1027:183-201.
Meng et al., "Optimized production of transgenic buffalo embryos and offspring by cytoplasmic zygote injection," J. Animal Sci. and Biotech., Oct. 2015, 1-7.
Murata et al., "Autoimmune animal models in the analysis of the CD47-SIRPa signaling pathway," Methods, 2013, pp. 1-6.
Paris et al. "Equine embryos and embryonic stem cells: defining reliable markers of pluripotency," Theriogenology, Sep. 2010, 74(4):516-524.
Schilit et al., "Pronuclear Injection-Based Targeted Transgenesis," Curr Protoc Hum Genet., Oct. 2016, 91(1):15.10.1-15.10.28.
Seiffert et al. "Signal-regulatory protein a (SIRPa) but not SIRPb is involved in T-cell activation, binds to CD47 with high affinity, and is expressed on immature CD34+ CD38-hematopoietic cells." Blood, 2001, 97(9):2741-2749.
Shultz et al., "Humanized mice for immune system investigation: progress, promise, and challenges," Nature Reviews Immunology, 2012, 12:786-798.
Strowig et al., "Transgenic expression of human signal regulatory protein alpha in Rag2-/-yc-/-mice improves engraftment of human hematopoietic cells in humanized mice," PNAS, 2011, 108(32):1-6.
Tena et al., "Transgenic expression of human CD47 markedly increases engraftment in a murine model of pig-to-human hematopoietic cell transplantation," Am J. Transplantation, 2014, 14(12):2713-2722.
Tong et al., "Production of p53 gene knockout rats by homologous recombination in embryonic stem cells," Nature, Sep. 2010, 467(7312):211-213.
West et al., "Genome Editing in Large Animals," J. Equine Vet. Sci., Jun. 2016, 41:1-12.
Yanagita et al. "Anti-SIRPa antibodies as a potential new tool for cancer immunotherapy." JCI insight 2.1 (2017).
Yin et al., "Delivery technologies for genome editing," Nature Reviews Drug Discovery, 2017, 16(6):387-399.
Zeng et al., "Generation and expression analysis of human [*Homo sapiens*] CD47 transgenic Bama Miniature Pig (*Sus scrofa*)," Journal of Agricultural Biotechnology, 2016, 24(8):1251-1258 (with English abstract).

* cited by examiner (A) Primers : L-GT-F/L-GT-R (B) Primers : R-GT-F/R-GT-R 1612 bp

B-F1-1 B-F1-2 B-F1-4 B-F1-5 B-F1-7 M B-F1-10 + WT H2O

UTR
Mouse coding
Human coding

5'UTR
Exon1
Exon2
Exon3
Exon4
Exon5
Exon6
Exon7
Exon8
Exon9
Exon10
3'UTR

| Score | Expect | Method | Identities | Positives | Gaps |
|---|---|---|---|---|---|
| 421 bits(1082) | 2e-153 | Compositional matrix adjust. | 213/325(66%) | 250/325(76%) | 23/325(7%) |

```
Mouse  1    MWPLAAALLLGSCCCGSAQLLFSNVNSIEFTSCNETVVIPCIVRNVEAQSTEEMFVKWKL  60
            MWPL AALLLGS CCGSAQLLF+   S+EFT CN+TVVIPC V N+EAQ+T E++VKWK
Human  1    MWPLVAALLLGSACCGSAQLLFNKTKSVEFTFCNDTVVIPCFVTNMEAQNTTEVYVKWKF  60

Mouse  61   NKSYIFIYDGNKNSTTTDQNFTSAKISVSDLINGIASLKMDKRDAM--VGNYTCEVTELS  118
                I+ +DG  N +T   +F+SAKI VS L+ G ASLKMDK DA+   GNYTCEVTEL+
Human  61   KGRDIYTFDGALNKSTVPTDFSSAKIEVSQLLKGDASLKMDKSDAVSHTGNYTCEVTELT  120

Mouse  119  REGKTVIELKNRTAFNTDQGSACSYEEEKGGCKLVSWFSPNEKILIVIFPILAILLFWGK  178
            REG+T+IELK R                     +VSWFSPNE ILIVIFPI AILLFWG+
Human  121  REGETIIELKYR---------------------VVSWFSPNENILIVIFPIFAILLFWGQ  159

Mouse  179  FGILTLKYKSSHTNKRIILLLVAGLVLTVIVVVGAILLIPGEKPVKNASGLGLIVISTGI  238
            FGI TLKY+S   +++ I LLVAGLV+TVIV+VGAIL +PGE   +KNA+GLGLIV STGI
Human  160  FGIKTLKYRSGGMDEKTIALLVAGLVITVIVIVGAILFVPGEYSLKNATGLGLIVTSTGI  219

Mouse  239  LILLQYNVFMTAFGMTSFTIAILITQVLGYVLALVGLCLCIMACEPVHGPLLISGLGIIA  298
            LILL Y VF TA G+TSF IAIL+ QV+ Y+LA+VGL LCI AC P+HGPLLISGL I+A
Human  220  LILLHYYVFSTAIGLTSFVIAILVIQVIAYILAVVGLSLCIAACIPMHGPLLISGLSILA  279

Mouse  299  LAELLGLVYMKFVASNQRTIQPPRN  323
            LA+LLGLVYMKFVASNQ+TIQPPR
Human  280  LAQLLGLVYMKFVASNQKTIQPPRK  304
```

GENETICALLY MODIFIED MICE EXPRESSING HUMANIZED CD47

CLAIM OF PRIORITY

This application is a continuation of U.S. application Ser. No. 16/435,368, now U.S. Pat. No. 10,918,095, which is a continuation of and claims priority to international Application No. PCT/CN2018/081628, filed on Apr. 2, 2018, which claims the benefit of Chinese Patent Application No. 201710205646.7, filed on Mar. 31, 2017, Chinese Patent Application No. 201711039543.4, filed on Oct. 27, 2017. The entire contents of the foregoing are incorporated herein by reference.

TECHNICAL FIELD

This disclosure relates to genetically modified animal expressing human or chimeric (e.g., humanized) CD47, and methods of use thereof.

BACKGROUND

The immune system has developed multiple mechanisms to prevent deleterious activation of T cells. One such mechanism is the intricate balance between positive and negative costimulatory signals delivered to T cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, thus the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human CD47 or chimeric CD47. The animal model can express human CD47 or chimeric CD47 (e.g., humanized CD47) protein in its body. It can be used in the studies on the function of CD47 gene, and can be used in the screening and evaluation of anti-human CD47 and anti-SIRPα antibodies. In addition, the animal models prepared by the methods described herein can be used in drug screening, pharmacodynamics studies, treatments for immune-related diseases (e.g., autoimmune disease), and cancer therapy for human CD47 target sites; they can also be used to facilitate the development and design of new drugs, and save time and cost. In summary, this disclosure provides a powerful tool for studying the function of CD47 protein and a platform for screening cancer drugs.

In one aspect, the disclosure provides a genetically-modified, non-human animal whose genome comprises at least one chromosome comprising a sequence encoding a human or chimeric CD47.

In some embodiments, the sequence encoding the human or chimeric CD47 is operably linked to an endogenous regulatory element at the endogenous CD47 gene locus in the at least one chromosome.

In some embodiments, the sequence encoding a human or chimeric CD47 comprises a sequence encoding an amino acid sequence that is at least 50%, 55%, 65%, 70%, 75%, 80%, 85%, 90%, 95%, 99%, or 100% identical to human CD47 (SEQ ID NO: 63, 64, 65, or 66).

In some embodiments, the sequence encoding a human or chimeric CD47 comprises a sequence encoding an amino acid sequence that is at least 50%, 55%, 65%, 70%, 75%, 80%, 85%, 90%, 95%, 99%, or 100% identical to SEQ ID NO: 74, 75, 76, 77, 78, 79, or 80.

In some embodiments, the sequence encoding a human or chimeric CD47 comprises a sequence that is at least 50%, 55%, 65%, 70%, 75%, 80%, 85%, 90%, 95%, 99%, or 100% identical to amino acids 23-126 of SEQ ID NO: 63.

In some embodiments, the animal is a mammal, e.g., a monkey, a rodent or a mouse. In some embodiments, the animal is a BALB/c mouse or a C57BL/6 mouse.

In some embodiments, the animal does not express endogenous CD47. In some embodiments, the animal has one or more cells expressing human or chimeric CD47. In some embodiments, the animal has one or more cells expressing human or chimeric CD47, and the expressed human or chimeric CD47 can bind to endogenous SIRPα. In some embodiments, the animal has one or more cells expressing human or chimeric CD47, and the expressed human or chimeric CD47 cannot bind to endogenous SIRPα.

In another aspect, the disclosure is related to a genetically-modified, non-human animal, wherein the genome of the animal comprises a replacement of a sequence encoding a region of endogenous CD47 with a sequence encoding a corresponding region of human CD47 at an endogenous CD47 gene locus.

In some embodiments, the sequence encoding the corresponding region of human CD47 is operably linked to an endogenous regulatory element at the endogenous CD47 locus, and one or more cells of the animal expresses a chimeric CD47.

In some embodiments, the animal does not express endogenous CD47. In some embodiments, the replaced locus is the extracellular N-terminal IgV domain of CD47.

In some embodiments, the animal has one or more cells expressing a chimeric CD47 having an extracellular N-terminal IgV domain, wherein the extracellular N-terminal IgV domain comprises a sequence that is at least 50%, 60%, 70%, 80%, 90%, 95%, or 99% identical to the extracellular N-terminal IgV domain of human CD47.

In some embodiments, the extracellular N-terminal IgV domain of the chimeric CD47 has a sequence that has at least 10, 20, 30, 40, 50, 60, 70, 80, 90, or 100 contiguous amino acids that are identical to a contiguous sequence present in the extracellular N-terminal IgV domain of human CD47.

In some embodiments, the animal is a mouse, and the replaced endogenous CD47 locus is exon 1, exon 2, exon 3, exon 4, exon 5, exon 6, exon 7, exon 8, exon 9, and/or exon 10 of the endogenous mouse CD47 gene.

In some embodiments, the animal is heterozygous with respect to the replacement at the endogenous CD47 gene locus. In some embodiments, the animal is homozygous with respect to the replacement at the endogenous CD47 gene locus.

In another aspect, the disclosure is related to methods for making a genetically-modified, non-human animal. The methods involve replacing in at least one cell of the animal, at an endogenous CD47 gene locus, a sequence encoding a region of an endogenous CD47 with a sequence encoding a corresponding region of human CD47.

In some embodiments, the sequence encoding the corresponding region of human CD47 comprises exon 2 of a human CD47 gene.

In some embodiments, the sequence encoding the corresponding region of CD47 comprises at least 100, 150, 200, 250, or 300 nucleotides of exon 2 of a human CD47 gene.

In some embodiments, the sequence encoding the corresponding region of human CD47 encodes a sequence that is at least 90% identical to amino acids 23-126 of SEQ ID NO: 63.

In some embodiments, the locus is located within the extracellular N-terminal IgV domain of CD47.

In some embodiments, the animal is a mouse, and the locus is exon 1, exon 2, exon 3, exon 4, exon 5, exon 6, exon 7, exon 8, exon 9, and/or exon 10 of the mouse CD47 gene (e.g., exon 2).

In another aspect, the disclosure is also related to a non-human animal comprising at least one cell comprising a nucleotide sequence encoding a chimeric CD47 polypeptide, wherein the chimeric CD47 polypeptide comprises at least 50 contiguous amino acid residues that are identical to the corresponding contiguous amino acid sequence of a human CD47, wherein the animal expresses the chimeric CD47.

In some embodiments, the chimeric CD47 polypeptide has at least 50 contiguous amino acid residues that are identical to the corresponding contiguous amino acid sequence of a human CD47 extracellular N-terminal IgV domain.

In some embodiments, the chimeric CD47 polypeptide comprises a sequence that is at least 90%, 95%, or 99% identical to amino acids 23-126 of SEQ ID NO: 63.

In some embodiments, the nucleotide sequence is operably linked to an endogenous CD47 regulatory element of the animal.

In some embodiments, the chimeric CD47 polypeptide comprises five endogenous CD47 transmembrane regions and/or an endogenous CD47 C-terminal intracellular tail.

In some embodiments, the nucleotide sequence is integrated to an endogenous CD47 gene locus of the animal.

In some embodiments, the chimeric CD47 has at least one mouse CD47 activity and/or at least one human CD47 activity.

In another aspect, the disclosure is also related to methods of making a genetically-modified mouse cell that expresses a chimeric CD47. The methods involve replacing, at an endogenous mouse CD47 gene locus, a nucleotide sequence encoding a region of mouse CD47 with a nucleotide sequence encoding a corresponding region of human CD47, thereby generating a genetically-modified mouse cell that includes a nucleotide sequence that encodes the chimeric CD47, wherein the mouse cell expresses the chimeric CD47.

In some embodiments, the chimeric CD47 comprises: an extracellular N-terminal IgV domain of human CD47; and one or more transmembrane domains of mouse CD47 and/or a C-terminal intracellular tail of mouse CD47.

In some embodiments, the nucleotide sequence encoding the chimeric CD47 is operably linked to an endogenous CD47 regulatory region, e.g., promoter.

In some embodiments, the animal further comprises a sequence encoding an additional human or chimeric protein (e.g., SIRPα, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, or TNF Receptor Superfamily Member 4 (OX40)).

In some embodiments, the additional human or chimeric protein is SIRPα and/or PD-1.

In one aspect, the disclosure also provides methods of determining effectiveness of a CD47 antagonist (e.g., an anti-CD47 antibody) for the treatment of cancer. The methods involve administering the CD47 antagonist to the animal described herein, wherein the animal has a tumor; and determining the inhibitory effects of the CD47 antagonist to the tumor.

In some embodiments, the animal comprises one or more cells that express SIRPα. In some embodiments, the tumor comprises one or more cells that express SIRPα.

In some embodiments, the tumor comprises one or more cancer cells that are injected into the animal.

In some embodiments, determining the inhibitory effects of the CD47 antagonist (e.g., an anti-CD47 antibody) to the tumor involves measuring the tumor volume in the animal.

In some embodiments, the tumor cells are melanoma cells, non-small cell lung carcinoma (NSCLC) cells, small cell lung cancer (SCLC) cells, non-Hodgkin lymphoma cells, bladder cancer cells, prostate cancer cells, breast cancer cells, ovarian cancer cells, colorectal cancer cells, and/or refractory solid tumor cells.

In another aspect, the disclosure also provides methods of determining effectiveness of a CD47 antagonist (e.g., an anti-CD47 antibody) and an additional therapeutic agent for the treatment of a tumor. The methods involve administering the CD47 antagonist and the additional therapeutic agent to the animal as described herein, wherein the animal has a tumor; and determining the inhibitory effects on the tumor.

In some embodiments, the animal further comprises a sequence encoding a human or chimeric SIRPα.

In some embodiments, the additional therapeutic agent is an anti-SIRPα antibody.

In some embodiments the additional therapeutic agent is an anti-PD-1 antibody, an anti-PD-L1 antibody, an anti-CTLA4 antibody, an anti-CD20 antibody, an anti-EGFR antibody, or an anti-CD319 antibody.

In some embodiments, the tumor comprises one or more tumor cells that express CD47.

In some embodiments, the tumor is caused by injection of one or more cancer cells into the animal.

In some embodiments, determining the inhibitory effects of the treatment involves measuring the tumor volume in the animal.

In some embodiments the tumor comprises melanoma cells, non-small cell lung carcinoma (NSCLC) cells, small cell lung cancer (SCLC) cells, non-Hodgkin lymphoma cells, bladder cancer cells, prostate cancer cells, breast cancer cells, ovarian cancer cells, colorectal cancer cells, and/or refractory solid tumor cells.

In another aspect, the disclosure further provides methods of determining toxicity of an agent (e.g., a CD47 antagonist). The methods involve administering the agent to the animal as described herein; and determining weight change of the animal. In some embodiments, the method further involve performing a blood test (e.g., determining red blood cell count).

In one aspect, the disclosure relates to proteins comprising an amino acid sequence, wherein the amino acid sequence is one of the following:

(a) an amino acid sequence set forth in SEQ ID NO: 74, 75, 76, 77, 78, 79, or 80;

(b) an amino acid sequence that is at least 90%, 91%, 92%, 93%, 94%, 95%, 96%, 97%, 98%, or 99% identical to SEQ ID NO: 74, 75, 76, 77, 78, 79, or 80;

(c) an amino acid sequence that is different from the amino acid sequence set forth in SEQ ID NO: 74, 75, 76, 77, 78, 79, or 80 by no more than 10, 9, 8, 7, 6, 5, 4, 3, 2 or 1 amino acid; and (d) an amino acid sequence that comprises a substitution, a deletion and/or insertion of one, two, three, four, five or more amino acids to the amino acid sequence set forth in SEQ ID NO: 74, 75, 76, 77, 78, 79, or 80.

In some embodiments, provided herein are cells comprising the proteins disclosed herein. In some embodiments, provided herein are animals having the proteins disclosed herein.

In another aspect, the disclosure relates to nucleic acids comprising a nucleotide sequence, wherein the nucleotide sequence is one of the following:

(a) a sequence that encodes the protein as described herein;

(b) SEQ ID NO: 67, 68, 69, 70, 71, 72, or 73;

(c) SEQ ID NO: 23;

(d) a sequence that is at least 90%, 91%, 92%, 93%, 94%, 95%, 96%, 97%, 98%, or 99% identical to SEQ ID NO: 67, 68, 69, 70, 71, 72, or 73; and (e) a sequence that is at least 90%, 91%, 92%, 93%, 94%, 95%, 96%, 97%, 98%, or 99% identical to SEQ ID NO: 23.

In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous CD47 gene, wherein the disruption of the endogenous CD47 gene comprises deletion of exon 2 or part thereof of the endogenous CD47 gene.

In some embodiments, the disruption of the endogenous CD47 gene further comprises deletion of one or more exons or part of exons selected from the group consisting of exon 1, exon 3, exon 4, exon 5, exon 6, exon 7, exon 8, exon 9, and exon 10 of the endogenous CD47 gene.

In some embodiments, the disruption of the endogenous CD47 gene further comprises deletion of one or more introns or part of introns selected from the group consisting of intron 1, intron 2, intron 3, intron 4, intron 5, intron 6, intron 7, intron 8, and intron 9 of the endogenous CD47 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous CD47 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, exon 8, exon 9, or exon 10 (e.g., deletion of at least 300 nucleotides of exon 2).

In some embodiments, the mice described in the present disclosure can be mated with the mice containing other human or chimeric genes (e.g., chimeric SIRPα, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In one aspect, the disclosure relates to a targeting vector, including a) a DNA fragment homologous to the 5' end of a region to be altered (5' arm), which is selected from the CD47 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD47 gene genomic DNAs in the length of 100 to 10,000 nucleotides.

In some embodiments, a) the DNA fragment homologous to the 5' end of a region to be altered (5' arm) is selected from the nucleotide sequences that have at least 90% homology to the NCBI accession number NC 000082.6; c) the DNA fragment homologous to the 3' end of the region to be altered (3' arm) is selected from the nucleotide sequences that have at least 90% homology to the NCBI accession number NC 000082.6.

In some embodiments, a) the DNA fragment homologous to the 5' end of a region to be altered (5' arm) is selected from the nucleotides from the position 49866727 to the position 49867784 of the NCBI accession number NC 000082.6; c) the DNA fragment homologous to the 3' end of the region to be altered (3' arm) is selected from the nucleotides from the position 49868091 to the position 49869239 of the NCBI accession number NC 000082.6.

In some embodiments, a length of the selected genomic nucleotide sequence is about 3 kb, 3.5 kb, 4 kb, 4.5 kb, or 5 kb. In some embodiments, the region to be altered is exon 1, exon 2, exon 3, exon 4, exon 5, exon 6, exon 7, exon 8, exon 9, and/or exon 10 of mouse CD47 gene.

In some embodiments, the sequence of the 5' arm is shown in SEQ ID NO: 24. In some embodiments, the sequence of the 3' arm is shown in SEQ ID NO: 32.

In some embodiments, the targeting vector further includes a selectable gene marker.

In some embodiments, the target region is derived from human. In some embodiments, the target region is a part or entirety of the nucleotide sequence of a humanized CD47. In some embodiments, the nucleotide sequence is shown as one or more of exon 1, exon 2, exon 3, exon 4, exon 5, exon 6, exon 7, exon 8, exon 9, exon 10, and exon 11 of the human CD47.

In some embodiments, the nucleotide sequence of the human CD47 encodes the human CD47 protein with the NCBI accession number NP_001768.1 (SEQ ID NO: 63). In some emboldens, the nucleotide sequence of the human CD47 is selected from the nucleotides from the position 108080013 to the position 108080324 of NC_000003.12 with T→C point mutation at 108080196 (SEQ ID NO: 27).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a CD47 gene humanized animal model to obtain a CD47 gene genetically modified humanized mouse;
(b) mating the CD47 gene genetically modified humanized mouse obtained in step (a) with another humanized mouse, and then screening to obtain a double humanized mouse model.

In some embodiments, in step (b), the CD47 gene genetically modified humanized mouse obtained in step (a) is mated with a SIRPα humanized mouse to obtain a CD47 and SIRPα double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CD47 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a CD47 amino acid sequence of a humanized mouse, wherein the amino acid sequence is selected from the group consisting of:

a) an amino acid sequence shown in SEQ ID NO: 74, 75, 76, 77, 78, 79, or 80;
b) an amino acid sequence having a homology of at least 90% with the amino acid sequence shown in SEQ ID NO: 74, 75, 76, 77, 78, 79, or 80;
c) an amino acid sequence encoded by a nucleic acid sequence, wherein the nucleic acid sequence is able to hybridize to a nucleotide sequence encoding the amino acid shown in SEQ ID NO: 74, 75, 76, 77, 78, 79, or 80 under a low stringency condition or a strict stringency condition;
d) an amino acid sequence having a homology of at least 90%, 91%, 92%, 93%, 94%, 95%, 96%, 97%, 98%, or at least 99% with the amino acid sequence shown in SEQ ID NO: 74, 75, 76, 77, 78, 79, or 80;
e) an amino acid sequence that is different from the amino acid sequence shown in SEQ ID NO: 74, 75, 76, 77, 78, 79, or 80 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 74, 75, 76, 77, 78, 79, or 80.

The disclosure also relates to a CD47 nucleic acid sequence of a humanized mouse, wherein the nucleic acid sequence is selected from the group consisting of:

a) a nucleic acid sequence that encodes the CD47 amino acid sequence of a humanized mouse;
b) a nucleic acid sequence that is set forth in SEQ ID NO: 23;
c) a nucleic acid sequence having a coding DNA sequence (CDS) as shown in SEQ ID NO: 67, 68, 69, 70, 71, 72, or 73;
d) a nucleic acid sequence that can hybridize to the nucleotide sequence as shown in SEQ ID NO: 67, 68, 69, 70, 71, 72, or 73 or SEQ ID NO: 23 under a low stringency condition or a strict stringency condition;
e) a nucleic acid sequence that has a homology of at least 90%, 91%, 92%, 93%, 94%, 95%, 96%, 97%, 98%, or at least 99% with the nucleotide sequence as shown in SEQ ID NO: 67, 68, 69, 70, 71, 72, or 73 or SEQ ID NO: 23;
f) a nucleic acid sequence that encodes an amino acid sequence, wherein the amino acid sequence has a homology of at least 90% with the amino acid sequence shown in SEQ ID NO: 74, 75, 76, 77, 78, 79, or 80;
g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 74, 75, 76, 77, 78, 79, or 80;
h) a nucleic acid sequence that encodes an amino acid sequence, wherein the amino acid sequence is different from the amino acid sequence shown in SEQ ID NO: 74, 75, 76, 77, 78, 79, or 80 by no more than 10, 9, 8, 7, 6, 5, 4, 3, 2 or no more than 1 amino acid; and/or
i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 74, 75, 76, 77, 78, 79, or 80.

The disclosure further relates to a CD47 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD47 gene function, human CD47 antibodies, the drugs or efficacies for human CD47 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 17C-17D show results from PCR confirming that humanized mice are homozygous for humanized SIRPα. WT indicates wildtype. PC is positive control.

FIG. 26 is a schematic diagram showing a map of an example of humanized CD47 gene in mouse.

FIG. 28 shows the alignment between mouse CD47 amino acid sequence (NP_034711.1; SEQ ID NO: 52) and human CD47 amino acid sequence (NP_001768.1; SEQ ID NO: 63).

DETAILED DESCRIPTION

Figure 1B:
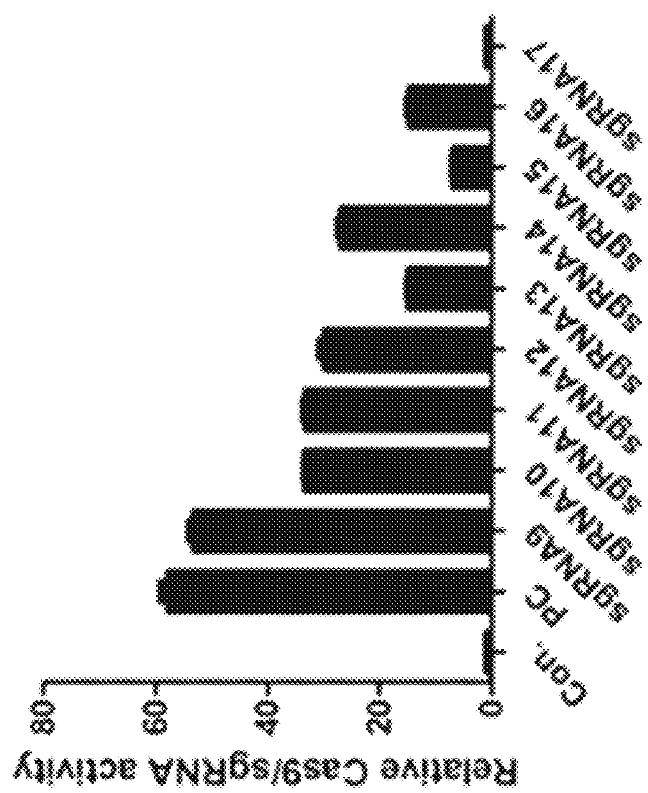
FIG. 1B is a graph showing activity testing results for sgRNA9-sgRNA17 (Con is a negative control; PC is a positive control).

This disclosure relates to transgenic non-human animal with human or chimeric (e.g., humanized) CD47, and methods of use thereof.

CD47, also known as integrin associated protein (IAP), is a transmembrane protein that in humans is encoded by the CD47 gene. CD47 belongs to the immunoglobulin superfamily and partners with membrane integrins and also binds the ligands thrombospondin-1 (TSP-1) and signal-regulatory protein alpha (SIRPα). It is involved in a range of cellular processes, including apoptosis, proliferation, adhesion, and migration.

CD47 provides a "do not eat" signal by binding to the N-terminus of signal regulatory protein alpha (SIRPα) on immune cells and suppresses phagocytosis, and it is ubiquitously expressed in human cells and has been found to be overexpressed in many different tumor cells. Thus, targeting CD47 is in the spotlight of cancer immunotherapy. Blocking CD47 triggers the recognition and elimination of cancer cells by the innate immunity. There are at least three CD47 antagonists in phase I clinical trials, including Hu5F9-G4, CC-90002, and TTI-621. These antibodies or binding agents can be used to treat various tumors and cancers, e.g., solid tumors, hematologic malignancies (e.g., relapsed or refractory hematologic malignancies), acute myeloid leukemia, non-Hodgkin's lymphoma, breast cancer, bladder cancer, ovarian cancer, and small cell lung cancer tumors. These CD47 antagonists are described, e.g., in Huang et al. "Targeting CD47: the achievements and concerns of current studies on cancer immunotherapy." Journal of thoracic disease 9.2 (2017): E168; Liu et al. "Pre-clinical development of a humanized anti-CD47 antibody with anti-cancer therapeutic potential." PloS one 10.9 (2015): e0137345; Ansell et al. "A phase 1 study of TTI-621, a novel immune checkpoint inhibitor targeting CD47, in patients with relapsed or refractory hematologic malignancies." (2016): 1812-1812; which are incorporated herein by reference in its entirety.

Experimental animal models are an indispensable research tool for studying the effects of these antibodies. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels. Furthermore, because of interaction between human CD47 and human SIRPα, a desirable animal model for the investigation of anti-CD47 should faithfully mimic the interaction between human CD47 and human SIRPα, elicit robust responses from both the innate and adaptive immunity, and recapitulate side effects of CD47 blockade on RBCs and platelets (Huang et al. "Targeting CD47: the achievements and concerns of current studies on cancer immunotherapy." Journal of thoracic disease 9.2 (2017): E168).

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullis et al U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD47

CD47 is a ~50 kDa heavily glycosylated, ubiquitously expressed membrane protein of the immunoglobulin superfamily with a single IgV-like domain at its N-terminus, a highly hydrophobic stretch with five membrane-spanning segments and an alternatively spliced cytoplasmic C-terminus. Each of the four alternatively spliced cytoplasmic tails exists in vivo at different frequencies, but all lack a substantial signaling domain.

While CD47 was first identified as a membrane protein involved in β3 integrin-mediated signaling on leukocytes, it is now known to also interact with thrombospondin-1, signal regulatory protein-alpha (SIRPα, also known as SIRPA, Sirpα, Sirpa, or CD172A), and others to regulate various cellular functions including cell migration, axon extension, cytokine production, and T cell activation.

Recent studies have focused most on CD47-SIRPα axis for its inhibitory role in phagocytosis. SIRPα, also known as Src homology 2 domain-containing protein tyrosine phosphatase substrate 1/brain Ig-like molecule with tyrosine-based activation motif/cluster of differentiation antigen-like family member A (SHPS-1/BIT/CD172a), is another membrane protein of the immunoglobulin superfamily that is particularly abundant in the myeloid-lineage hematopoietic cells such as macrophages and dendritic cells. The ligation of SIRPα on phagocytes by CD47 expressed on a neighboring cell results in phosphorylation of SIRPα cytoplasmic immunoreceptor tyrosine-based inhibition (ITIM) motifs, leading to the recruitment of SHP-1 and SHP-2 phosphatases. One resulting downstream effect is the prevention of myosin-IIA accumulation at the phagocytic synapse and consequently inhibition of phagocytosis. Thus, CD47-SIRPα interaction functions as a negative immune checkpoint to send a "don't eat me" signal to ensure that healthy autologous cells are not inappropriately phagocytosed.

Overexpression of CD47 has been found in nearly all types of tumors, some of which include acute myeloid leukemia, non-Hodgkin's lymphoma, bladder cancer, and breast cancer. While CD47 is implicated in the regulation of cancer cell invasion and metastasis, its most well-studied and important function related to tumor development is prevention of phagocytosis via ligating with SIRPα on the surrounding phagocytes. Also, CD47 expression on cancer stem cells (CSCs) implies its role in cancer recurrence. It can increase the chance of CSC survival, which in turn could repopulate a new tumor mass and cause a tumor relapse.

CD47 down-regulation is also involved in the clearance of red blood cells (RBCs) and platelets by splenic macrophages, which may cause hemolytic anemia and idiopathic thrombocytopenic purpura, respectively. Thus, when CD47 antagonists are used as therapies, it is also very important to assess its toxicities.

A detailed description of CD47 and its function can be found, e.g., in Liu, Xiaojuan, et al. "Is CD47 an innate immune checkpoint for tumor evasion?." Journal of hematology & oncology 10.1 (2017): 12; Huang et al. "Targeting CD47: the achievements and concerns of current studies on cancer immunotherapy." Journal of thoracic disease 9.2 (2017): E168; which are incorporated by reference herein in the entirety.

In human genomes, CD47 gene (Gene ID: 961) locus has 11 exons, exon 1, exon 2, exon 3, exon 4, exon 5, exon 6, exon 7, exon 8, exon 9, exon 10, and exon 11. The CD47 protein has an extracellular N-terminal IgV domain, five transmembrane domains, a short C-terminal intracellular tail. In addition, it has two extracellular regions and two intracellular regions between neighboring transmembrane domains. The signal peptide is located at the extracellular N-terminal IgV domain of CD47. The nucleotide sequence for human CD47 mRNA is NM_001777.3 (SEQ ID NO: 59), and the amino acid sequence for human CD47 is NP_001768.1 (SEQ ID NO: 63). The location for each exon and each region in human CD47 nucleotide sequence and amino acid sequence is listed below:

TABLE 1

| Human CD47 (approximate location) | NM_001777.3 5346 bp (SEQ ID NO: 59) | NP_001768.1 323 aa (SEQ ID NO: 63) |
|---|---|---|
| Exon 1 | 1-226 | 1-15 |
| Exon 2 | 227-580 | 16-133 |
| Exon 3 | 581-670 | 134-163 |
| Exon 4 | 671-778 | 164-199 |
| Exon 5 | 779-871 | 200-230 |
| Exon 6 | 872-964 | 231-261 |
| Exon 7 | 965-1057 | 262-292 |
| Exon 8 | 1058-1089 | 293-303 |
| Exon 9 | 1090-1114 | 304-311 |
| Exon 10 | 1115-1147 | 312-322 |
| Exon 11 | 1148-5346 | 323 |
| Signal peptide | 181-234 | 1-18 |
| Donor region in one example | 247-558* (with point mutation 375(T→C)) | 23-126 |

The extracellular N-terminal IgV domain is 19-141 of SEQ ID NO: 63, and the C-terminal intracellular tail is located at 290-323 of SEQ ID NO: 63. Thus, the donor region is located within the extracellular N-terminal IgV domain.

Human CD47 also have several transcript variants. These variants are summarized below.

TABLE 2

| Human CD47 transcript variants | Amino acid sequences |
|---|---|
| NM_001777.3 | NP_001768.1 |
| SEQ ID NO: 59 (5346bp) | SEQ ID NO: 63 (323 aa) |
| NM_198793.2 | NP_942088.1 |
| SEQ ID NO: 60 (5288bp) | SEQ ID NO: 64 (305 aa) |
| XM_005247909.1 | XP_005247966.1 |
| SEQ ID NO: 61 (5021bp) | SEQ ID NO: 65 (293 aa) |
| XM_005247908.1 | XP_005247965.1 |
| SEQ ID NO: 62 (5078bp) | SEQ ID NO: 66 (312 aa) |

Figure 25:
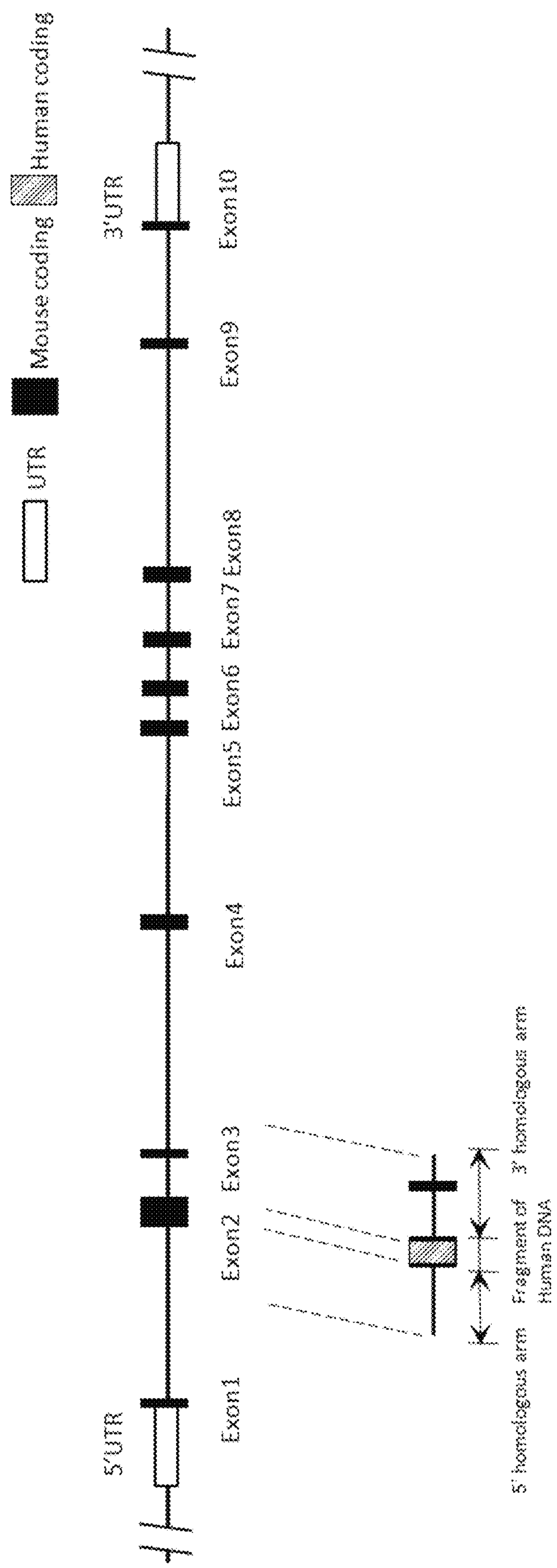
FIG. 25 is a schematic diagram showing mouse CD47 gene targeting strategy.
Figure 27:
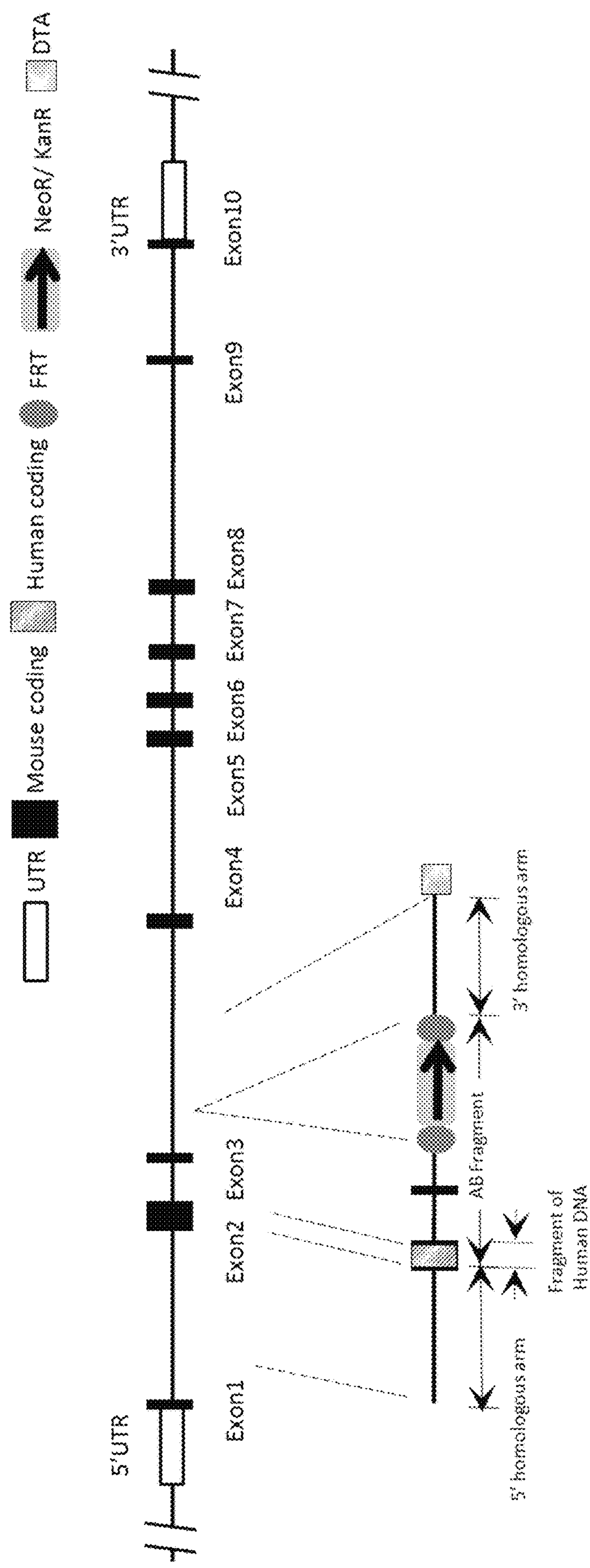
FIG. 27 is a schematic diagram showing gene targeting strategy using embryonic stem (ES) cells.

In mice, CD47 gene locus has 10 exons, exon 1, exon 2, exon 3, exon 4, exon 5, exon 6, exon 7, exon 8, exon 9, and exon 10 (FIG. 25). The mouse CD47 protein also has an extracellular N-terminal IgV domain, five transmembrane domains, and a short C-terminal intracellular tail, and the signal peptide is located at the extracellular N-terminal IgV domain of CD47. The nucleotide sequence for mouse CD47 cDNA is NM_010581.3 (SEQ ID NO: 45), the amino acid sequence for mouse CD47 is NP_034711.1 (SEQ ID NO: 52). The location for each exon and each region in the mouse CD47 nucleotide sequence and amino acid sequence is listed below:

TABLE 3

| Mouse CD47 (approximate location) | NM_010581.3 1928 bp (SEQ ID NO: 45) | NP_034711.1 324 aa (SEQ ID NO: 52) |
|---|---|---|
| Exon 1 | 1-179 | 1-15 |
| Exon 2 | 180-527 | 16-131 |
| Exon 3 | 528-590 | 132-152 |
| Exon 4 | 591-680 | 153-182 |
| Exon 5 | 681-788 | 183-218 |
| Exon 6 | 789-881 | 219-249 |
| Exon 7 | 882-974 | 250-280 |
| Exon 8 | 975-1067 | 281-311 |
| Exon 9 | 1068-1099 | 312-322 |
| Exon 10 | 1100-1919 | 323-324 |
| Signal peptide | 134-187 | 1-18 |
| Replaced region in one example | 200-505 | 23-124 |

The mouse CD47 gene (Gene ID: 16423) is located in Chromosome 16 of the mouse genome, which is located from 49855253 to 49912424, of NC_000082.6 (GRCm38.p4 (GCF_000001635.24)). The 5'-UTR is from 49855618 to 49855786, exon 1 is from 49,855,618 to 49,855,832, the first intron is from 49,855,833 to 49,867,764, exon 2 is from 49,867,765 to 49,868,112, the second intron is from 49,868,113 to 49,869,017, exon 3 is from 49,869,018 to 49,869,080, the third intron is from 49,869,081 to 49,884,164, exon 4 is from 49,884,165 to 49,884,254, the fourth intron is from 49,884,255 to 49,894,176, exon 5 is from 49,894,177 to 49,894,284, the fifth intron is from 49,894,285 to 49,895,368, exon 6 is from 49,895,369 to 49,895,461, the sixth intron is from 49,895,462 to 49,896,355, exon 7 is from 49,896,356 to 49,896,448, the seventh intron is from 49,896,449 to 49,898,039, exon 8 is from 49,898,040 to 49,898,132, the eighth intron is from 49,898,133 to 49,906,780, exon 9 is from 49,906,781 to 49,906,812, the ninth intron is from 49,906,813 to 49,910,868, exon 10 is from 49,910,869 to 49,915,010, the 3'-UTR is from 49910878 to 49,915,010, based on transcript NM_010581.3. All relevant information for mouse CD47 locus can be found in the NCBI website with Gene ID: 16423, which is incorporated by reference herein in its entirety.

Like human CD47, mouse CD47 also have several transcript variants. These variants are summarized in Table 4.

FIG. 28 shows the alignment between mouse CD47 amino acid sequence (NP_034711.1; SEQ ID NO: 52) and human CD47 amino acid sequence (NP_001768.1; SEQ ID NO: 63). Thus, the corresponding amino acid residue or region between human and mouse CD47 can also be found in FIG. 28.

CD47 genes, proteins, and locus of the other species are also known in the art. For example, the gene ID for CD47 in *Rattus norvegicus* is 29364, the gene ID for CD47 in *Macaca mulatta* (Rhesus monkey) is 704980, the gene ID for CD47 in *Canis lupus familiaris* (dog) is 478552, and the gene ID for CD47 in *Cavia porcellus* (domestic guinea pig) is 100727770. The relevant information for these genes (e.g., intron sequences, exon sequences, amino acid residues of these proteins) can be found, e.g., in NCBI database.

The present disclosure provides human or chimeric (e.g., humanized) CD47 nucleotide sequence and/or amino acid sequences. In some embodiments, the entire sequence of mouse exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region are replaced by the corresponding human sequence. As used herein, the first transmembrane domain refers to the first transmembrane domain starting from the N-terminal of CD47. Similarly, the second, third, fourth, and fifth transmembrane domain refers to the second, third, fourth, and fifth transmembrane domain starting from the N-terminal of CD47.

In some embodiments, a "region" or "portion" of mouse exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region is replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues.

In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region. In some embodiments, a region, a portion, or the entire sequence of mouse exon 2 is replaced by a region, a portion, or the entire sequence of human exon 2.

In some embodiments, a "region" or "portion" of mouse exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region is deleted.

The mouse CD47 has several transcript variants. A portion of these sequences can also be replaced by corresponding human sequences. Some exemplary sequences are shown in Table 4.

TABLE 4

| Mouse CD47 sequence | | Humanized CD47 sequence | |
|---|---|---|---|
| mRNA sequence | Amino acid sequence | mRNA sequence | Amino acid sequence |
| NM_010581.3 SEQ ID NO: 45 (1928bp) | NP_034711.1 SEQ ID NO: 52 (324aa) | SEQ ID NO: 67 (1934bp) | SEQ ID NO: 74 (326aa) |
| XM_006521809.3 SEQ ID NO: 46 (3101bp) | XP_006521872.1 SEQ ID NO: 53 (320aa) | SEQ ID NO: 68 (3107bp) | SEQ ID NO: 75 (322aa) |
| XM_006521806.3 SEQ ID NO: 47 (3114bp) | XP_006521869.1 SEQ ID NO: 54 (342aa) | SEQ ID NO: 69 (3120bp) | SEQ ID NO: 76 (344aa) |
| XM_006521807.3 SEQ ID NO: 48 (3081bp) | XP_006521870.1 SEQ ID NO: 55 (331aa) | SEQ ID NO: 70 (3087bp) | SEQ ID NO: 77 (333aa) |
| XM_006521810.3 SEQ ID NO: 49 (3024bp) | XP_006521873.1 SEQ ID NO: 56 (312aa) | SEQ ID NO: 71 (3030bp) | SEQ ID NO: 78 (314aa) |
| XM_006521808.3 SEQ ID NO: 50 (3051bp) | XP_006521871.1 SEQ ID NO: 57 (321aa) | SEQ ID NO: 72 (3057bp) | SEQ ID NO: 79 (323aa) |
| XM_006521811.3 SEQ ID NO: 51 (2993bp) | XP_006521874.1 SEQ ID NO: 58 (303aa) | SEQ ID NO: 73 (2999bp) | SEQ ID NO: 80 (305aa) |

Thus, in some embodiments, the present disclosure also provides a chimeric (e.g., humanized) CD47 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD47 mRNA sequence (e.g., SEQ ID NO: 45, 46, 47, 48, 49, 50, or 51), mouse CD47 amino acid sequence (e.g., SEQ ID NO: 52, 53, 54, 55, 56, 57, 58), or a portion thereof (e.g., exon 1, exon 2, exon 3, exon 4, exon 5, exon 6, exon 7, exon 8, exon 9, or exon 10); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD47 mRNA sequence (e.g., SEQ ID NO: 59, 60, 61, or 62), human CD47 amino acid sequence (e.g., SEQ ID NO: 63, 64, 65, or 66), or a portion thereof (e.g., exon 1, exon 2, exon 3, exon 4, exon 5, exon 6, exon 7, exon 8, exon 9, exon 10, or exon 11).

In some embodiments, the sequence encoding amino acids 23-124 of mouse CD47 (SEQ ID NO: 52) is replaced. In some embodiments, the sequence is replaced by a sequence encoding a corresponding region of human CD47 (e.g., amino acids 23-126 of human CD47 (SEQ ID NO: 63).

In some embodiments, the nucleic acids as described herein are operably linked to a promotor or regulatory element, e.g., an endogenous mouse CD47 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD47 nucleotide sequence (e.g., exon 1, exon 2, exon 3, exon 4, exon 5, exon 6, exon 7, exon 8, exon 9, exon 10, or SEQ ID NO: 45, 46, 47, 48, 49, 50, or 51).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD47 nucleotide sequence (e.g., exon 1, exon 2, exon 3, exon 4, exon 5, exon 6, exon 7, exon 8, exon 9, exon 10, or SEQ ID NO: 45, 46, 47, 48, 49, 50, or 51).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD47 nucleotide sequence (e.g., exon 1, exon 2, exon 3, exon 4, exon 5, exon 6, exon 7, exon 8, exon 9, exon 10, exon 11, or SEQ ID NO: 59, 60, 61, or 62).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD47 nucleotide sequence (e.g., exon 1, exon 2, exon 3, exon 4, exon 5, exon 6, exon 7, exon 8, exon 9, exon 10, exon 11, or SEQ ID NO: 59, 60, 61, or 62).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD47 amino acid sequence (e.g., exon 1, exon 2, exon 3, exon 4, exon 5, exon 6, exon 7, exon 8, exon 9, exon 10, or SEQ ID NO: 52, 53, 54, 55, 56, 57, or 58).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD47 amino acid sequence (e.g., exon 1, exon 2, exon 3, exon 4, exon 5, exon 6, exon 7, exon 8, exon 9, exon 10, or SEQ ID NO: 52, 53, 54, 55, 56, 57, or 58).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD47 amino acid sequence (e.g., exon 1, exon 2, exon 3, exon 4, exon 5, exon 6, exon 7, exon 8, exon 9, exon 10, exon 11, or SEQ ID NO: 63, 64, 65, or 66).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD47 amino acid sequence (e.g., exon 1, exon 2, exon 3, exon 4, exon 5, exon 6, exon 7, exon 8, exon 9, exon 10, exon 11, or SEQ ID NO: 63, 64, 65, or 66).

The present disclosure also provides a humanized CD47 mouse amino acid sequence, wherein the amino acid sequence is selected from the group consisting of:

a) an amino acid sequence shown in SEQ ID NO: 74, 75, 76, 77, 78, 79, or 80;
b) an amino acid sequence having a homology of at least 90% with or at least 90% identical to the amino acid sequence shown in SEQ ID NO: 74, 75, 76, 77, 78, 79, or 80;
c) an amino acid sequence encoded by a nucleic acid sequence, wherein the nucleic acid sequence is able to hybridize to a nucleotide sequence encoding the amino acid shown in SEQ ID NO: 74, 75, 76, 77, 78, 79, or 80 under a low stringency condition or a strict stringency condition;
d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 74, 75, 76, 77, 78, 79, or 80;
e) an amino acid sequence that is different from the amino acid sequence shown in SEQ ID NO: 74, 75, 76, 77, 78, 79, or 80 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 74, 75, 76, 77, 78, 79, or 80.

The present disclosure also relates to a CD47 nucleic acid (e.g., DNA or RNA) sequence, wherein the nucleic acid sequence can be selected from the group consisting of:

a) a nucleic acid sequence as shown in SEQ ID NO: 67, 68, 69, 70, 71, 72, or 73, or a nucleic acid sequence encoding a homologous CD47 amino acid sequence of a humanized mouse;
b) a nucleic acid sequence that is shown in SEQ ID NO: 23;
c) a nucleic acid sequence that is able to hybridize to the nucleotide sequence as shown in SEQ ID NO: 23, 67, 68, 69, 70, 71, 72, or 73 under a low stringency condition or a strict stringency condition;
d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 23, 67, 68, 69, 70, 71, 72, or 73;
e) a nucleic acid sequence that encodes an amino acid sequence, wherein the amino acid sequence has a homology of at least 90% with or at least 90% identical to the amino acid sequence shown in SEQ ID NO: 74, 75, 76, 77, 78, 79, or 80;
f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 74, 75, 76, 77, 78, 79, or 80;
g) a nucleic acid sequence that encodes an amino acid sequence, wherein the amino acid sequence is different from the amino acid sequence shown in SEQ ID NO: 74, 75, 76, 77, 78, 79, or 80 by no more than 10, 9, 8, 7, 6, 5, 4, 3, 2 or no more than 1 amino acid; and/or
h) a nucleic acid sequence that encodes an amino acid sequence, wherein the amino acid sequence comprises a substitution, a deletion and/or insertion of one or more amino acids to the amino acid sequence shown in SEQ ID NO: 74, 75, 76, 77, 78, 79, or 80.

The present disclosure further relates to a CD47 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 23, 67, 68, 69, 70, 71, 72, or 73.

The disclosure also provides an amino acid sequence that has a homology of at least 90% with, or at least 90% identical to the sequence shown in SEQ ID NO: 74, 75, 76, 77, 78, 79, or 80, and has protein activity. In some embodiments, the homology with the sequence shown in SEQ ID NO: 74, 75, 76, 77, 78, 79, or 80 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 74, 75, 76, 77, 78, 79, or 80 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 67, 68, 69, 70, 71, 72, or 73, and encodes a polypeptide that has protein activity. In some embodiments, the homology with the sequence shown in SEQ ID NO: 67, 68, 69, 70, 71, 72, or 73 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 67, 68, 69, 70, 71, 72, or 73 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of identical residues (percent identity) and the percentage of residues conserved with similar physicochemical properties (percent homology), e.g. leucine and isoleucine, can be used to measure sequence similarity. Residues conserved with similar physicochemical properties are well known in the art. The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) CD47 from an endogenous non-human CD47 locus.

Genetically Modified Animals

As used herein, the term "genetically-modified non-human animal" refers to a non-human animal having genetic modification (e.g., exogenous DNA) in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the genetic modification in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous CD47 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CD47 gene or a humanized CD47 nucleic acid. In some embodiments, at least one or more portions of the gene or the nucleic acid is from the human CD47 gene, at least one or more portions of the gene or the nucleic acid is from a non-human CD47 gene. In some embodiments, the gene or the nucleic acid comprises a sequence that encodes a CD47 protein. The encoded CD47 protein is functional or has at least one activity of the human CD47 protein or the non-human CD47 protein, e.g., binding to human or non-human SIRPα, promoting phosphorylation of SIRPα cytoplasmic ITIM motif, inhibiting phagocytosis, downregulating immune response, binding TSP-1, suppressing c-Myc expression, and/or inhibiting self-renewal.

In some embodiments, the chimeric protein or the chimeric polypeptide is a humanized CD47 protein or a humanized CD47 polypeptide. In some embodiments, at least one or more portions of the amino acid sequence of the protein or the polypeptide is from a human CD47 protein, and at least one or more portions of the amino acid sequence of the protein or the polypeptide is from a non-human CD47 protein. The humanized CD47 protein or the humanized CD47 polypeptide is functional or has at least one activity of the human CD47 protein or the non-human CD47 protein.

In some embodiments, the humanized CD47 protein or the humanized CD47 polypeptide can bind to mouse SIRPα, inhibit phagocytosis, and/or downregulate immune response. In some embodiments, the humanized CD47 protein or the humanized CD47 polypeptide cannot bind to mouse SIRPα, thus cannot inhibit phagocytosis.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CD47 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CD47 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SOD/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature CD47 coding sequence with human mature CD47 coding sequence.

The mouse genetic background can affect the interaction of CD47 and SIRPα in the mouse. In mice with C57BL/6 background, the mouse SIRPα has a relatively weak binding affinity with humanized or human CD47 protein. In contrast, in mice with BALB/c background, the binding affinity between mouse SIRPα and human (or humanized) CD47 protein is similar to the binding affinity between mouse SIRPα and mouse CD47 protein. Thus, in some embodiments, the humanized CD47 mouse with C57BL/6 background can be used to test the toxicity of anti-hCD47 antibodies. In some embodiments, the humanized CD47 mouse with BALB/c background can be used to test the toxicity of anti-hCD47 antibodies and/or the efficacy of anti-hCD47 antibodies in terms of inhibiting tumor growth. In some embodiments, mice (any background) with both humanized CD47 and humanized SIRPα can be used to test the toxicity of anti-hCD47 antibodies and/or the efficacy of anti-hCD47 antibodies in terms of inhibiting tumor growth.

Genetically modified non-human animals can comprise a modification of an endogenous non-human CD47 locus. In some embodiments, the modification can comprise a human nucleic acid sequence encoding at least a portion of a mature CD47 protein (e.g., at least 10%, 20%, 30%, 40%, 50%, 60%, 70%, 80%, 90%, 95%, 96%, 97%, 98%, or 99% identical to the mature CD47 protein sequence). Although genetically modified cells are also provided that can comprise the modifications described herein (e.g., ES cells, somatic cells), in many embodiments, the genetically modified non-human animals comprise the modification of the endogenous CD47 locus in the germline of the animal.

Genetically modified animals can express a human CD47 and/or a chimeric (e.g., humanized) CD47 from endogenous mouse loci, wherein the endogenous mouse CD47 gene has been replaced with a human CD47 gene and/or a nucleotide sequence that encodes a region of human CD47 sequence or an amino acid sequence that is at least 10%, 20%, 30%, 40%, 50%, 60%, 70&, 80%, 90%, 95%, 96%, 97%, 98%, or 99% identical to the human CD47 sequence. In various embodiments, an endogenous non-human CD47 locus is modified in whole or in part to comprise human nucleic acid sequence encoding at least one protein-coding sequence of a mature CD47 protein.

In some embodiments, the genetically modified mice express the human CD47 and/or chimeric CD47 (e.g., humanized CD47) from endogenous loci that are under control of mouse promoters and/or mouse regulatory elements. The replacement(s) at the endogenous mouse loci provide non-human animals that express human CD47 or chimeric CD47 (e.g., humanized CD47) in appropriate cell types and in a manner that does not result in the potential pathologies observed in some other transgenic mice known in the art. The human CD47 or the chimeric CD47 (e.g., humanized CD47) expressed in animal can maintain one or more functions of the wildtype mouse or human CD47 in the animal. For example, CD47 can bind to human or non-human SIRPα, and downregulate immune response, e.g., downregulate immune response by at least 10%, 20%, 30%, 40%, or 50%. Furthermore, in some embodiments, the animal does not express endogenous CD47. As used herein, the term "endogenous CD47" refers to CD47 protein that is expressed from an endogenous CD47 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human CD47 (e.g., SEQ ID NO: 63, 64, 65, or 66). In some embodiments, the genome comprises a sequence encoding an amino acid sequence that is at least 70%, 75%, 80%, 85%, 90%, 95%, 99%, or 100% identical to SEQ ID NO: 74, 75, 76, 77, 78, 79, or 80.

The genome of the genetically modified animal can comprise a replacement at an endogenous CD47 gene locus of a sequence encoding a region of endogenous CD47 with a sequence encoding a corresponding region of human CD47. In some embodiments, the sequence that is replaced is any sequence within the endogenous CD47 gene locus, e.g., exon 1, exon 2, exon 3, exon 4, exon 5, exon 6, exon 7, exon 8, exon 9, exon 10, 5'-UTR, 3'UTR, the first intron, the second intron, and the third intron, the fourth intron, the fifth intron, the sixth intron, the seventh intron, the eighth intron, or the ninth intron etc. In some embodiments, the sequence that is replaced is within the regulatory region of the endogenous CD47 gene. In some embodiments, the sequence that is replaced is exon 2 or part thereof, of an endogenous mouse CD47 gene locus.

The genetically modified animal can have one or more cells expressing a human or chimeric CD47 (e.g., humanized CD47) having a N-terminal IgV domain and a C-terminal intracellular region, wherein the N-terminal IgV domain comprises a sequence that is at least 50%, 60%, 70%, 80%, 90%, 95%, 99% identical to the N-terminal IgV domain of human CD47. In some embodiments, the N-terminal IgV domain of the humanized CD47 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human CD47.

Because human CD47 and non-human CD47 (e.g., mouse CD47) sequences, in many cases, are different, antibodies that bind to human CD47 will not necessarily have the same binding affinity with non-human CD47 or have the same effects to non-human CD47. Therefore, the genetically modified animal having a human or a humanized extracellular region can be used to better evaluate the effects of anti-human CD47 antibodies in an animal model. In some embodiments, the genome of the genetically modified animal comprises a sequence encoding an amino acid sequence that corresponds to part or the entire sequence of exon 2 of human CD47, part or the entire sequence of the extracellular N-terminal IgV domain of human CD47 (with or without signal peptide), or part or the entire sequence of amino acids 23-126 of SEQ ID NO: 63.

In some embodiments, the non-human animal can have, at an endogenous CD47 gene locus, a nucleotide sequence encoding a chimeric human/non-human CD47 polypeptide, wherein a human portion of the chimeric human/non-human CD47 polypeptide comprises a portion of human CD47 extracellular N-terminal IgV domain, and wherein the animal expresses a functional CD47 on a surface of a cell of the animal. The human portion of the chimeric human/non-human CD47 polypeptide can comprise a portion of exon 2 of human CD47. In some embodiments, the human portion of the chimeric human/non-human CD47 polypeptide can comprise a sequence that is at least 80%, 85%, 90%, 95%, or 99% identical to amino acids 23-126 of SEQ ID NO: 63.

In some embodiments, the non-human portion of the chimeric human/non-human CD47 polypeptide comprises transmembrane domains, C-terminal intracellular region, and/or regions between transmembrane domains of an endogenous non-human CD47 polypeptide.

Furthermore, the genetically modified animal can be heterozygous with respect to the replacement at the endogenous CD47 locus, or homozygous with respect to the replacement at the endogenous CD47 locus.

In some embodiments, the humanized CD47 locus lacks a human CD47 5'-UTR. In some embodiment, the humanized CD47 locus comprises a rodent (e.g., mouse) 5'-UTR. In some embodiments, the humanization comprises a human 3'-UTR. In appropriate cases, it may be reasonable to presume that the mouse and human CD47 genes appear to be similarly regulated based on the similarity of their 5'-flanking sequence. As shown in the present disclosure, humanized CD47 mice that comprise a replacement at an endogenous mouse CD47 locus, which retain mouse regulatory elements but comprise a humanization of CD47 encoding sequence, do not exhibit obvious pathologies. Both genetically modified mice that are heterozygous or homozygous for humanized CD47 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CD47 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized CD47 in the genome of the animal.

In some embodiments, the non-human mammal comprises the genetic construct as described herein. In some embodiments, a non-human mammal expressing human or humanized CD47 is provided. In some embodiments, the tissue-specific expression of human or humanized CD47 protein is provided.

In some embodiments, the expression of human or humanized CD47 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CD47 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized CD47 protein.

Vectors

The present disclosure relates to a targeting vector, comprising: a) a DNA fragment homologous to the 5' end of a region to be altered (5' arm), which is selected from the CD47 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD47 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000082.6; c) the DNA fragment homologous to the 3' end of the region to be altered (3' arm) is selected from the nucleotide sequences that have at least 90% homology to the NCBI accession number NC_000082.6.

In some embodiments, a) the DNA fragment homologous to the 5' end of a region to be altered (5' arm) is selected from the nucleotides from the position 49866727 to the position 49867784 of the NCBI accession number NC_000082.6; c) the DNA fragment homologous to the 3' end of the region to be altered (3' arm) is selected from the nucleotides from the position 49868091 to the position 49869239 of the NCBI accession number NC_000082.6.

In some embodiments, the length of the selected genomic nucleotide sequence in the targeting vector can be about 3 kb, about 3.5 kb, about 4 kb, about 4.5 kb, or about 5 kb.

In some embodiments, the region to be altered is exon 1, exon 2, exon 3, exon 4, exon 5, exon 6, exon 7, exon 8, exon 9, or exon 10 of CD47 gene (e.g., exon 2 of mouse CD47 gene).

The targeting vector can further include a selected gene marker.

In some embodiments, the sequence of the 5' arm is shown in SEQ ID NO: 24; and the sequence of the 3' arm is shown in SEQ ID NO: 32.

In some embodiments, the sequence is derived from human (e.g., 108080013-108080324 of NC_000003.12). For example, the target region in the targeting vector is a part or entirety of the nucleotide sequence of a human CD47, preferably exon 2 of the human CD47. In some embodiments, the nucleotide sequence of the humanized CD47 encodes the entire or the part of human CD47 protein (e.g., SEQ ID NO: 63, 64, 65, or 66).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., “Delivery technologies for genome editing,” Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CD47 gene locus, a sequence encoding a region of an endogenous CD47 with a sequence encoding a corresponding region of human or chimeric CD47. In some embodiments, the replacement occurs in a germ cell, a somatic cell, a blastocyst, or a fibroblast, etc. The nucleus of a somatic cell or the fibroblast can be inserted into an enucleated oocyte.

FIG. 25 shows a humanization strategy for a mouse CD47 locus. In FIG. 25, the targeting strategy involves a vector comprising the 5' end homologous arm, human CD47 gene fragment, 3' homologous arm. The process can involve replacing endogenous CD47 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CD47 sequence with human CD47 sequence.

Thus, in some embodiments, the methods for making a genetically modified, humanized animal, can include the step of replacing at an endogenous CD47 locus (or site), a nucleic acid encoding a sequence encoding a region of endogenous CD47 with a sequence encoding a corresponding region of human CD47. The sequence can include a region (e.g., a part or the entire region) of exon 1, exon 2, exon 3, exon 4, exon 5, exon 6, exon 7, exon 8, exon 9, exon 10, and/or exon 11 of a human CD47 gene. In some embodiments, the sequence includes a region of exon 2 of a human CD47 gene (e.g., amino acids 23-126 of SEQ ID NO: 63). In some embodiments, the region is located within the extracellular N-terminal IgV domain of CD47. In some embodiments, the endogenous CD47 locus is exon 2 of mouse CD47.

In some embodiments, the methods of modifying a CD47 locus of a mouse to express a chimeric human/mouse CD47 peptide can include the steps of replacing at the endogenous mouse CD47 locus a nucleotide sequence encoding a mouse CD47 with a nucleotide sequence encoding a human CD47, thereby generating a sequence encoding a chimeric human/mouse CD47.

In some embodiments, the nucleotide sequence encoding the chimeric human/mouse CD47 can include a first nucleotide sequence encoding a region of the extracellular N-terminal IgV domain of mouse CD47 (with or without the mouse or human signal peptide sequence); a second nucleotide sequence encoding a region of the extracellular N-terminal IgV domain of human CD47; a third nucleotide sequence encoding the five transmembrane regions, the regions between the transmembrane regions, and/or the C-terminal intracellular tail of a mouse CD47.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a CD47 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 or BALB/c mouse).

In some embodiments, the non-human mammal in step (c) is a female with pseudo pregnancy (or false pregnancy).

In some embodiments, the fertilized eggs for the methods described above are C57BL/6 or BALB/c fertilized eggs. Other fertilized eggs that can also be used in the methods as described herein include, but are not limited to, FVB/N fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized CD47 protein, e.g., in a physiologically appropriate manner, provide a variety of uses that include, but are not limited to, developing therapeutics for human diseases and disorders, and assessing the toxicity and/or efficacy of these human therapeutics in the animal models.

In various aspects, genetically modified animals are provided that express human or humanized CD47, which are useful for testing agents that can decrease or block the interaction between CD47 and SIRPα or the interaction between CD47 and other CD47 receptors or ligands (e.g., TSP-1), testing whether an agent can increase or decrease the immune response, and/or determining whether an agent is an CD47 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CD47 antibody for the treatment of cancer. The methods involve administering the anti-CD47 antibody to the animal as described herein, wherein the animal has a tumor; and determining the inhibitory effects of the anti-CD47 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, Mill or CT.

In some embodiments, the tumor comprises one or more cancer cells (e.g., human or mouse cancer cells) that are injected into the animal. In some embodiments, the anti-CD47 antibody or anti-SIRPα antibody prevents CD47 from binding to SIRPα. In some embodiments, the anti-CD47 antibody or anti-SIRPα antibody cannot prevent CD47 from binding to SIRPα.

In some embodiments, the genetically modified animals can be used for determining whether an anti-CD47 antibody is a CD47 agonist or antagonist. In some embodiments, the methods as described herein are also designed to determine the effects of the agent (e.g., anti-CD47 antibodies) on CD47, e.g., whether the agent can stimulate macrophages, whether the agent can initiate an antitumor T-cell immune response, and/or whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-CD47 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CD47 antibody or anti-SIRPα antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the antibody is designed for treating hepatocellular, ovarian, colon, or cervical carcinomas. In some embodiments, the antibody is designed for treating advanced breast cancer, advanced ovarian cancer, and/or advanced refractory solid tumor. In some embodiments, the antibody is designed for treating metastatic solid tumors, NSCLC, melanoma, non-Hodgkin lymphoma, colorectal cancer, and multiple myeloma. In some embodiments, the treatment is designed for treating acute myeloid leukemia, non-Hodgkin's lymphoma, bladder cancer, or breast cancer.

In some embodiments, the antibody is designed for treating various autoimmune diseases. Thus, the methods as described herein can be used to determine the effectiveness of an antibody in inhibiting immune response.

The present disclosure also provides methods of determining toxicity of an antibody (e.g., anti-CD47 antibody or anti-SIRPα antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the CD47 gene function, human CD47 antibodies, drugs for human CD47 targeting sites, the drugs or efficacies for human CD47 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric CD47 gene and a sequence encoding one or more additional human or chimeric protein.

In some embodiments, the additional human or chimeric protein can be SIRPα, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, or TNF Receptor Superfamily Member 4 (TNFRSF4 or OX40).

In some embodiments, the additional human or chimeric protein is SIRPα. The animal that have a human or chimeric CD47 gene and a human or chimeric SIRPα gene can be used to determine the toxicities and the efficacy of an anti-CD47 antibody or an anti-SIRPα antibody at the same time. In some embodiments, one or more exons of SIRPα are replaced by human sequences. In some embodiments, the replaced SIRPα region is exon 2, exon 3, and/or exon 4 of the endogenous mouse SIRPα gene.

The methods of generating genetically modified animal model with two or more human or chimeric genes (e.g., humanized genes) can include the following steps:

(a) using the methods of introducing human CD47 gene or chimeric CD47 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, TIGIT, TIM-3, GITR, OX40, CD137, or SIRPα. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/117984, PCT/CN2017/120388; each of which is incorporated herein by reference in its entirety.

In some embodiments, the CD47 humanization is directly performed on a genetically modified animal having a human or chimeric SIRPα, PD-1, CTLA-4, BTLA, PD-L1, CD27, CD28, TIGIT, TIM-3, GITR, CD137, or OX40 gene.

In some embodiments, the CD47 humanization is directly performed on a genetically modified animal having a human or chimeric SIRPα.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CD47 antibody and an additional therapeutic agent for the treatment of cancer. The methods include administering the anti-CD47 antibody and the additional therapeutic agent to the animal, wherein the animal has a tumor; and determining the inhibitory effects of the combined treatment to the tumor.

In some embodiments, the additional therapeutic agent is an antibody that specifically binds to SIRPα, PD-1, CTLA-4, BTLA, PD-L1, CD27, CD28, CD47, TIGIT, TIM-3, GITR, CD137, or OX40. In some embodiments, the additional therapeutic agent is an anti-CTLA4 antibody (e.g., ipilimumab), an anti-CD20 antibody (e.g., rituximab), an anti-EGFR antibody (e.g., cetuximab), and an anti-CD319 antibody (e.g., elotuzumab), or anti-PD-1 antibody (e.g., nivolumab).

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD47, CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the treatment is designed for treating acute myeloid leukemia, non-Hodgkin's lymphoma, bladder cancer, and breast cancer.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

C57BL/6 mice were purchased from the China Food and Drugs Research Institute

National Rodent Experimental Animal Center.

BALB/c mice were obtained from Beijing Vital River Laboratory Animal Technology Co., Ltd.

AIO kit was obtained from Beijing Biocytogen Co., Ltd. (Catalog number: BCG-DX-004).

UCA kit was obtained from Beijing Biocytogen Co., Ltd. (Catalog number: BCG-DX-001)

BbsI, EcoRI, BamHI, EcoRV, XbaI, and HindIII restriction enzymes were purchased from NEB (Catalog numbers: R0539L, R3101M, R3136M, R0195S, R0145M, and R3104M).

TOP10 competent cells were purchased from the Tiangen Biotech (Beijing) Co. (Catalog number: CB104-02).

Anti-mCD3 antibody was obtained from BD (Catalog number: 553057).

Reverse Transcription Kit was obtained from Takara (Catalog number: 6110A).

PerCP/Cy5.5 anti-mouse TCR β chain (mTcRβ PerCP) antibody was purchased from Biolegend (Catalog number: 109228).

Alexa Fluor® 647 anti-mouse CD47 (mCD47 Aleax Fluor 647, mCD47 AF647) was purchased from Biolegend (Catalog number: 127510).

PE anti-human CD47 (hCD47 PE) antibody was purchased from Biolegend (Catalog number: 323108).

PE anti-mouse CD172a (SIRPα) Antibody (mSIRPα PE) was purchased from Biolegend (Catalog number: 144012).

APC anti-human CD172a/b (SIRPα/β) Antibody (hSIRPα APC) was purchased from Biolegend (Catalog number: 323810).

PE anti-mouse CD11b (mCD11b PE) antibody was purchased from Biolegend (Catalog number: 101208).

FITC anti-mouse F4/80 (mF4/80 FITC) antibody was purchased from Biolegend (Catalog number: 123108).

The pHSG299 was purchased from Takara (Catalog number: 3299).

KOD enzyme was purchased from Toyobo (Catalog number: KOD-101).

Flow cytometer was purchased from BD Biosciences (model: FACS Calibur™).

Example 1: Design of sgRNA for CD47 Gene

The 5'-terminal targeting sites (sgRNA1 to sgRNA8) and the 3'-terminal targeting sites (sgRNA9 to sgRNA17) were designed and synthesized.

The 5'-terminal targeting sites and the 3'-terminal targeting sites were all located in exon 2 of mouse CD47 gene. The targeting site sequences on CD47 for each sgRNA are shown below:

```
sgRNA1 target sequence (SEQ ID NO: 1):
5'- cccttgcatcgtccgtaatgtgg -3'

sgRNA2 target sequence (SEQ ID NO: 2):
5'- tccacattacggacgatgcaagg -3'

sgRNA3 target sequence (SEQ ID NO: 3):
5'- tgctttgcgcctccacattacgg -3'

sgRNA4 target sequence (SEQ ID NO: 4):
5'- cacttcatgcaatgaaactgtgg -3'

sgRNA5 target sequence (SEQ ID NO: 5):
5'- ccgaagaaatgtttgtgaagtgg -3'

sgRNA6 target sequence (SEQ ID NO: 6):
5'- attgcatgaagtgaactctatgg -3'

sgRNA7 target sequence (SEQ ID NO: 7):
5'- tcgtatattttcatctatgatgg-3'

sgRNA8 target sequence (SEQ ID NO: 8):
5'- ccacttcacaaacatttcttcgg -3'

sgRNA9 target sequence (SEQ ID NO: 9):
5'- aatggataagcgcgatgccatgg -3'

sgRNA10 target sequence (SEQ ID NO: 10):
5'-gataagcgcgatgccatggtggg-3'

sgRNA11 target sequence (SEQ ID NO: 11):
5'- gcaagtgtagtttcccaccatgg -3'

sgRNA12 target sequence (SEQ ID NO: 12):
5'- tcagtctcagacttaatcaatgg -3'

sgRNA13 target sequence (SEQ ID NO: 13):
5'-tgagactgagatttttgcactgg-3'

sgRNA14 target sequence (SEQ ID NO: 14):
5'- gcgcttatccattttcaaagagg -3'
```

-continued

```
sgRNA15 target sequence (SEQ ID NO: 15):
5'-tggcattgcctctttgaaaatgg-3'

sgRNA16 target sequence (SEQ ID NO: 16):
5'-gtgacagagttatccagagaagg-3'

sgRNA17 target sequence (SEQ ID NO: 17):
5'-tataactgttttgccttctctgg-3'
```

Example 2: Testing sgRNA Activity

Figure 1A:
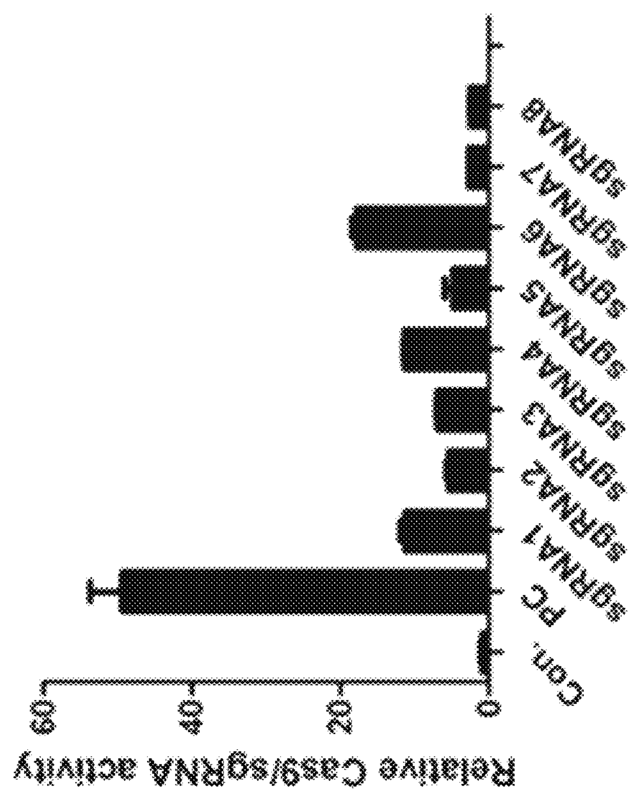
FIG. 1A is a graph showing activity testing results for sgRNA1-sgRNA8 (Con is a negative control; PC is a positive control).

The UCA kit was used to detect the activities of sgRNAs (FIG. 1). The results show that the guide sgRNAs had different activities. Two of them (sgRNA6 (SEQ ID NO: 6) and sgRNA9 (SEQ ID NO: 9)) were selected for further experiments.

The synthesized sgRNA sequences based on sgRNA6 and sgRNA9 target sequences are listed in the following table:

TABLE 5

| sgRNA6 and sgRNA9 sequences | |
|---|---|
| sgRNA6 sequences | |
| SEQ ID NO: 18 | Upstream: 5'- taggcatgaagtgaactcta- -3' |
| SEQ ID NO: 19 | Downstream: 5'- aaactagagttcacttcatg -3' |
| sgRNA9 sequences | |
| SEQ ID NO: 20 | Upstream: 5'- taggataagcgcgatgcca -3' |
| SEQ ID NO: 21 | Downstream: 5'- aaactggcatcgcgcttat -3' |

Example 3: Constructing pT7-sgRNA G2 Plasmids

Figure 2:
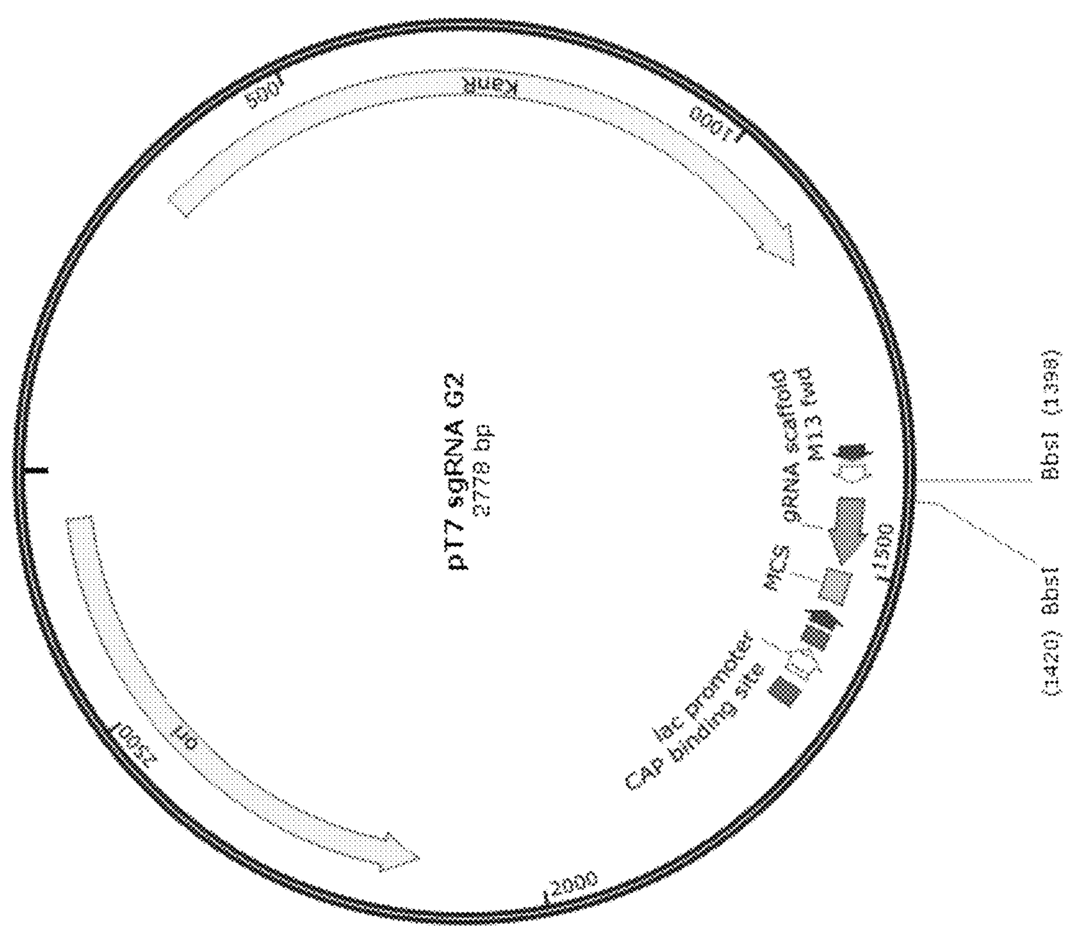
FIG. 2 is a schematic diagram showing the structure of pT7-sgRNA plasmid.

A map of pT7-sgRNA G2 vector is shown in FIG. 2. The plasmid backbone was obtained from Takara (Catalog No. 3299).

The DNA fragment containing T7 promoter and sgRNA scaffold was synthesized, and linked to the backbone vector by restriction enzyme digestion (EcoRI and BamHI) and ligation. The target plasmid was confirmed by the sequencing results.

The DNA fragment containing the T7 promoter and sgRNA scaffold (SEQ ID NO: 22) is shown below:

```
GAATTCTAATACGACTCACTATAGGGGGTCTTCGAGAAGACCTGTTTTAGA

GCTAGAAATAGCAAGTTAAAATAAGGCTAGTCCGTTATCAACTTGAAAAAG

TGGCACCGAGTCGGTGCTTTTAAAGGATCC
```

Example 4: Constructing Recombinant Expression Vectors pT7-CD47-6 and pT7-CD47-9

After annealing, the chosen sgRNA (sgRNA6 and sgRNA9) were ligated to pT7-sgRNA plasmids (linearized with BbsI) to produce the expression vectors pT7-CD47-6 and pT7-CD47-9. The ligation reaction was set up as follows:

TABLE 6

| The ligation reaction mix (10 μL) | |
|---|---|
| sgRNA after annealing | 1 μL (0.5 μM) |
| pT7-sgRNA vector | 1 μL (10 ng) |
| T4 DNA Ligase | 1 μL (5U) |
| 10 × T4 DNA Ligase buffer | 1 μL |
| 50% PEG4000 | 1 μL |
| $H_2O$ | Add to 10 μL |

The ligation reaction was carried out at room temperature for 10 to 30 minutes. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Clones were randomly selected and sequenced to verify their sequences. The vectors with correct sequences were selected for subsequent experiments.

Example 5: Sequence Design for Humanized CD47

Genomic DNA 12533-12838 on exon 2 of mouse CD47 gene was replaced with the corresponding portion of human CD47 gene (SEQ ID NO: 27), producing humanized mouse with the modified CD47 sequence as follows (the chimeric portion; SEQ ID NO: 23):

SEQ ID NO: 23 tatatgcagattgtaatgaaatatttttgtgtatgtattccaggttcagct caactactgttt*aataaaacaaaatctgtagaattcacgttttgtaatgac*

*actgtcgtcattccatgctttgttactaatatggaggcacaaaacactact*

*gaagtatacgtaaagtggaaatttaaaggaagagatatCtacacctttgat*

*ggagctctaaacaagtccactgtccccactgactttagtagtgcaaaaatt*

*gaagtctcacaattactaaaaggagatgcctctttgaagatggataagagt*

*gatgctgtctcacacacaggaaactacacttgtgaagtaacagaattaacc*

*agagaaggtgaaacgatc*catagagctgaaaaaccgcacgggtaagtgacac agtttgcctgttttgaaacgtgtgttgagatatggttgccactgtgggagt gctgtaaggtggaaccttgcagaagtc shows only the modified portion of DNA sequence, wherein the italicized underlined region is from human CD47. The capital letter indicates a point mutation.

Mice with humanized CD47 gene (modified exon 2 with human CD47 sequence) were generated. Because the human CD47 gene and the mouse CD47 gene both have multiple variants, the humanized mice can have different humanized CD47 gene variants as well. Non-limiting examples of mRNA sequences of humanized CD47 gene include SEQ ID NOs: 67-73, corresponding to amino acid sequences shown in SEQ ID NOs: 74-80. The same methods described herein can be used to generate other variants of humanized versions of mouse CD47 gene and the transgenic mice containing these variants.

Example 6: Construction of Homologous Recombination Targeting Vector

The 5' homologous arm, and the 3' homologous arm were designed, amplified and ligated to the corresponding human sequence.

The 5' Homologous Arm

The 5' homologous arm comprises nucleic acid 49866727-49867784 of NCBI Accession No. NC_000082.6 (SEQ ID NO: 24). The primers for the 5' homologous arm include:

```
Upstream primer (SEQ ID NO: 25):
F: 5'- tttaagaaggagatatacatgaattctgtctggtttacatagaa

ggaggaact -3'

Downstream primer (SEQ ID NO: 26):
R: 5'- gaattctacagattttgttttattaaacagtagttgagctgaac

ctggaa -3'
```

The Human Sequence Fragment

The human sequence fragment (312 bp) (SEQ ID NO: 27) corresponds to 108080324-108080013 of NCBI Accession No. NC_000003.12 with point mutation T→C at position 108080196 (129th bp). The difference does not affect protein expression.

The nucleic acid was introduced by amplifying two segments of DNA by PCR and using overlap PCR to produce the desired sequence (SEQ ID NO: 27). The PCR primers include the following:

```
Group I:
Upstream (SEQ ID NO: 28):
F: 5'- gttcagctcaactactgtttaataaaacaaaatctgtagaattc

acg - 3'

Downstream (SEQ ID NO: 29):
R: 5'- gtttagagctccatcaaaggtgtagatatctcttcctttaaatt

tccac - 3'

Group II:
Upstream (SEQ ID NO: 30):
F: 5'- gtggaaatttaaaggaagagatatctacacctttgatggagctc

taaac - 3'

Downstream (SEQ ID NO: 31):
R: 5'- gtgcggtttttcagctctatgatcgtttcaccttctctggttaa

ttc - 3'
```

The 3' Homologous Arm

The 3' homologous arm comprises nucleic acid 49868091-49869239 of NCBI Accession No. NC_000082.6 (SEQ ID NO: 32). The primers for the 5' homologous arm include:

```
Upstream primer (SEQ ID NO: 33):
F: 5'- ccagagaaggtgaaacgatcatagagctgaaaaaccgcacgggt

aag-3'

Downstream primer (SEQ ID NO: 34):
R: 5'-ttgttagcagccggatctcaggatcctaacaacactgctgtccgc

aactc-3'
```

Genomic DNA of C57BL/6 mouse was used as template for PCR amplifications of the 5' homologous arm and the 3' homologous arm. Genomic DNA of human was used as template for PCR amplification of the human DNA fragment. The AIO kit was used to ligate the 5' homologous arm, the 3' homologous arm, and the human sequence fragment into the pClon-4G plasmid, thereby generating the pClon-4G-CD47 vector.

Example 7: Verification of Vector pClon-4G-CD47

Six pClon-4G-CD47 clones were randomly selected and tested by three sets of restriction enzymes. Among them, EcoRI should generate 3579 bp+1371 bp+1082 bp fragments, EcoRV+XbaI should generate 4100 bp+1385 bp+547 bp fragments, HindIII+BamHI should generate 3456 bp+2576 bp fragments.

Figure 3:
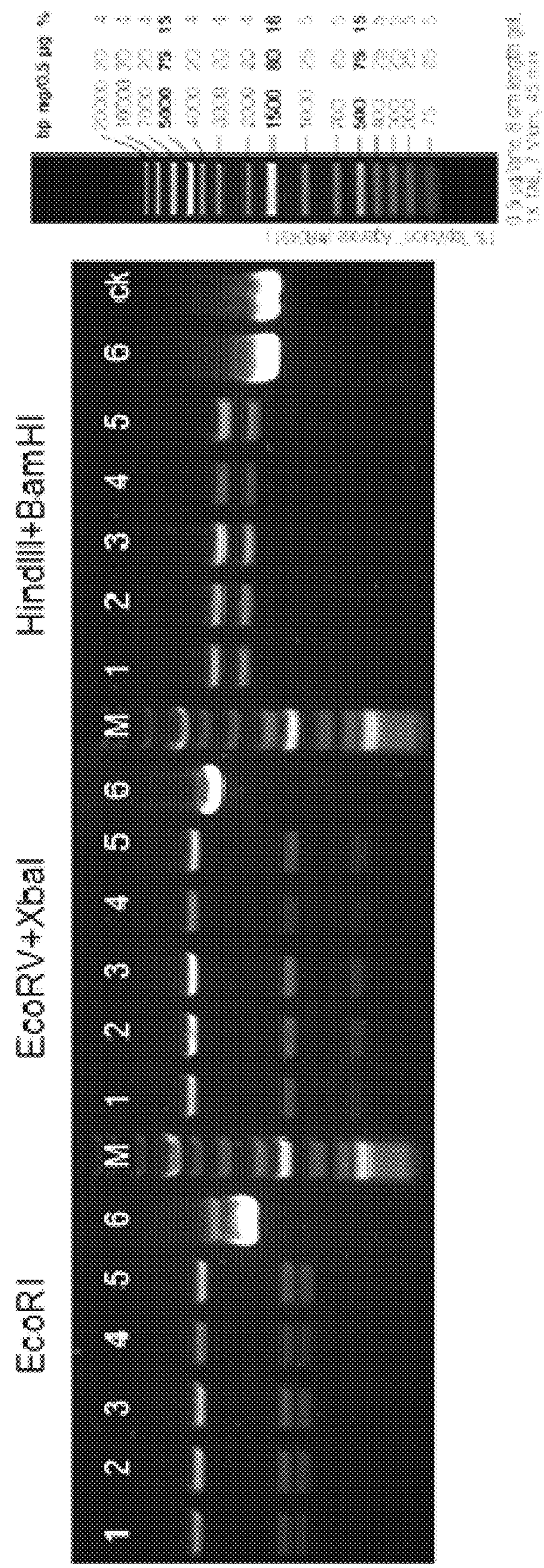
FIG. 3 shows the restriction enzymes digestion results of the targeting plasmid pClon-4G-CD47 by three sets of restriction enzymes

The results were in line with the expectations (FIG. 3). Plasmids 1, 2, 3, 4, 5 all showed expected results. The sequences of Plasmids 2 and 3 were further verified by sequencing.

Example 8: Microinjection and Embryo Transfer Using C57BL/6 Mice

The pre-mixed Cas9 mRNA, pClon-4G-CD47 plasmid and in vitro transcription products of pT7-CD47-6, pT7-CD47-9 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating and self-mating to establish stable mouse lines. The humanized mouse was named as B-hCD47(C57BL/6). Further binding experiments showed that human CD47 or humanized CD47 proteins have a relatively weak binding affinity with mouse SIRPα in B-hCD47(C57BL/6) mice.

Example 9: Microinjection and Embryo Transfer Using BALB/c Mice

The pre-mixed Cas9 mRNA, pClon-4G-CD47 plasmid and in vitro transcription products of pT7-CD47-6, pT7-CD47-9 plasmids were injected into the cytoplasm or nucleus of mouse fertilized eggs (BALB/c background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mice population was further expanded by cross-mating and self-mating to establish stable mouse lines. The humanized mouse was named as B-hCD47(BALB/c). Further binding experiments showed that human CD47 or humanized CD47 proteins can bind to mouse SIRPα in B-hCD47(BALB/c) mice, and the binding affinity is similar to the binding affinity between mouse SIRPα and mouse CD47 protein.

Example 10: Verification of Genetic Modification

1. Genotype Determination for F0 Generation Mice

PCR analysis was performed using mouse tail genomic DNA of F0 generation mice in both C57BL/6 background and BALB/c background. The primers are shown below with their relative locations.

```
5' end primers:
Upstream: L-GT-F (SEQ ID NO: 35), left side of
5' homologous arm:
5'- acccttagccagagagcacagagac - 3'

Downstream: L-GT-R (SEQ ID NO: 36), in exon 2:
5'- tggggacagtggacttgtttagagc -3'

3' end primers:
Upstream: R-GT-F (SEQ ID NO: 37), in exon 2:
5'- acactgtcgtcattccatgctttgt - 3'

Downstream: R-GT-R (SEQ ID NO: 38), right side of
3' homologous arm:
5'- acctggttctcaaagtgtcaccacc -3'
```

If the desired human sequence was inserted into the correct positions in the genome, PCR experiments using the above primers should generate only one band. The 5' end PCR experiment should produce a band at about 1,408 bp, and the 3' end PCR experiment should produce a band at about 1,612 bp.

TABLE 7

| The PCR reaction (20 μL) | |
|---|---|
| 10 × buffer | 2 μL |
| dNTP (2 mM) | 2 μL |
| $MgSO_4$ (25 mM) | 0.8 μL |
| Upstream primer (10 μM) | 0.6 μL |
| Downstream primer (10 μM) | 0.6 μL |
| Mouse tail genomic DNA | 200 ng |
| KOD-Plus-(1U/μL) | 0.6 μL |
| $ddH_2O$ | Add to 20 μL |

TABLE 8

The PCR reaction conditions

| Temperature | Time | Cycles |
|---|---|---|
| 94° C. | 5 min | 1 |
| 94° C. | 30 sec | 15 |
| 67° C. (−0.7° C./cycle) | 30 sec | |
| 68° C. | 1 kb/min | |
| 98° C. | 10 sec | 25 |
| 56° C. | 30 sec | |
| 68° C. | 1 kb/min | |
| 68° C. | 10 min | 1 |
| 4° C. | 10 min | 1 |

Figures 4A, 4B:
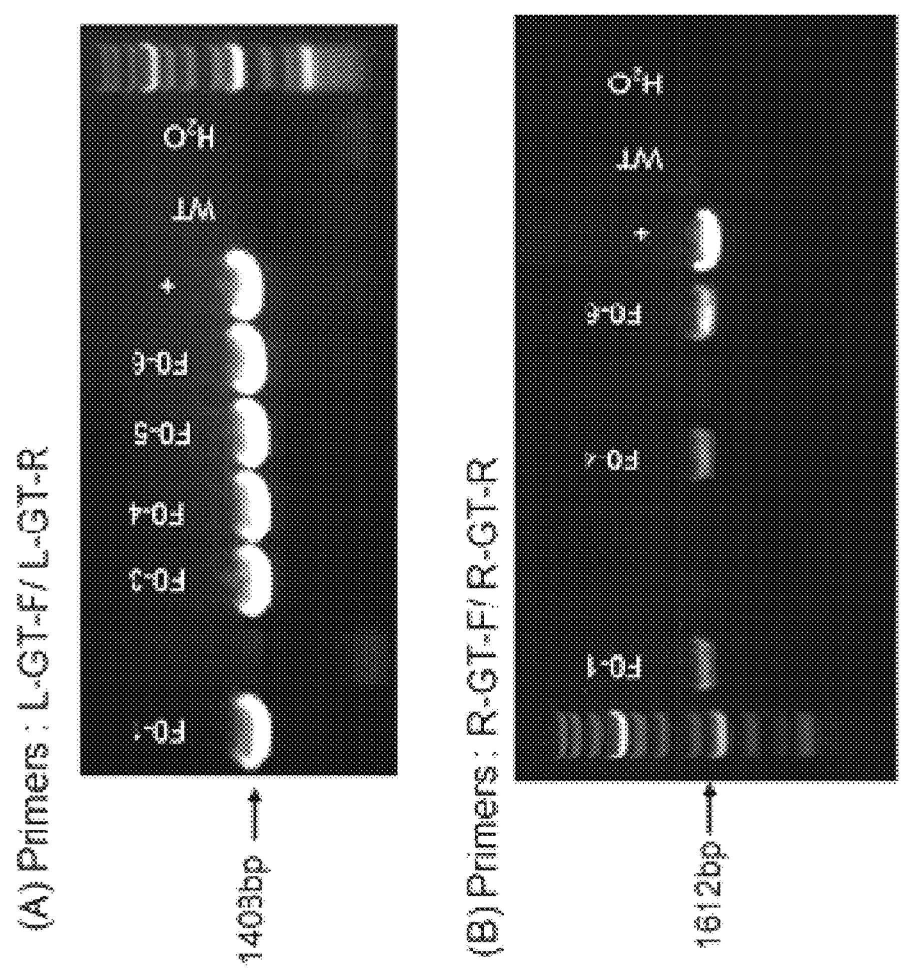
FIGS. 4A-4B show PCR identification results of samples collected from tails of F0 generation C57BL/6 mouse. WT is wildtype; + is positive control. Mice labeled with F0-1, F0-4, and F0-6 are positive.

Results for humanized mice with C57BL/6 background are shown in FIG. 4. F0-1, F0-4, and F0-6 had PCR products with correct size and thus had the correct sequences.

Figure 5A:
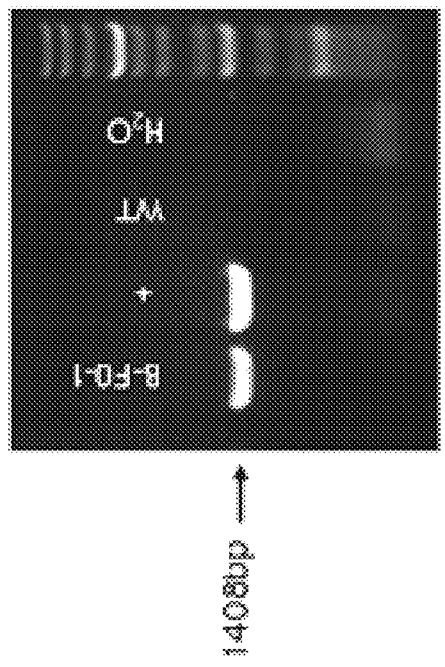
FIGS. 5A-5B shows PCR identification results of samples collected from tails of F0 generation BALB/c mouse. WT is wildtype; + is positive control. The mouse labeled with B-F0-1 is positive.
Figure 5B:
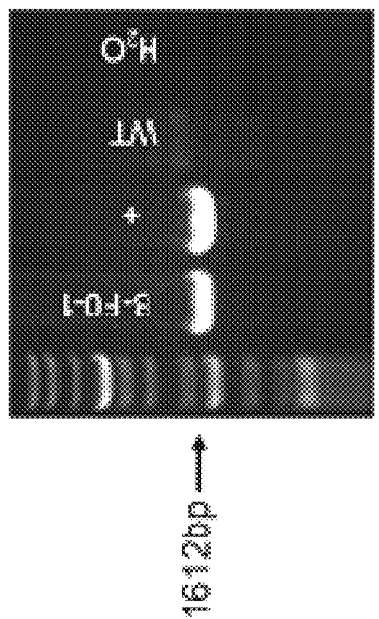

Results for humanized mice with BALB/c background are shown in FIG. 5. B-F0-1 had PCR products with correct size and thus had the correct sequences.

2. Genotype Determination for F1 Generation Mice

F1 generation mice were obtained by cross-mating F0 generation mice with wildtype mice in the same background. PCR experiments were performed using mouse tail genomic DNA from F1 generation mice. The PCR primers, setup, and conditions were the same as those used in the experiments above.

Figures 6A, 6B:
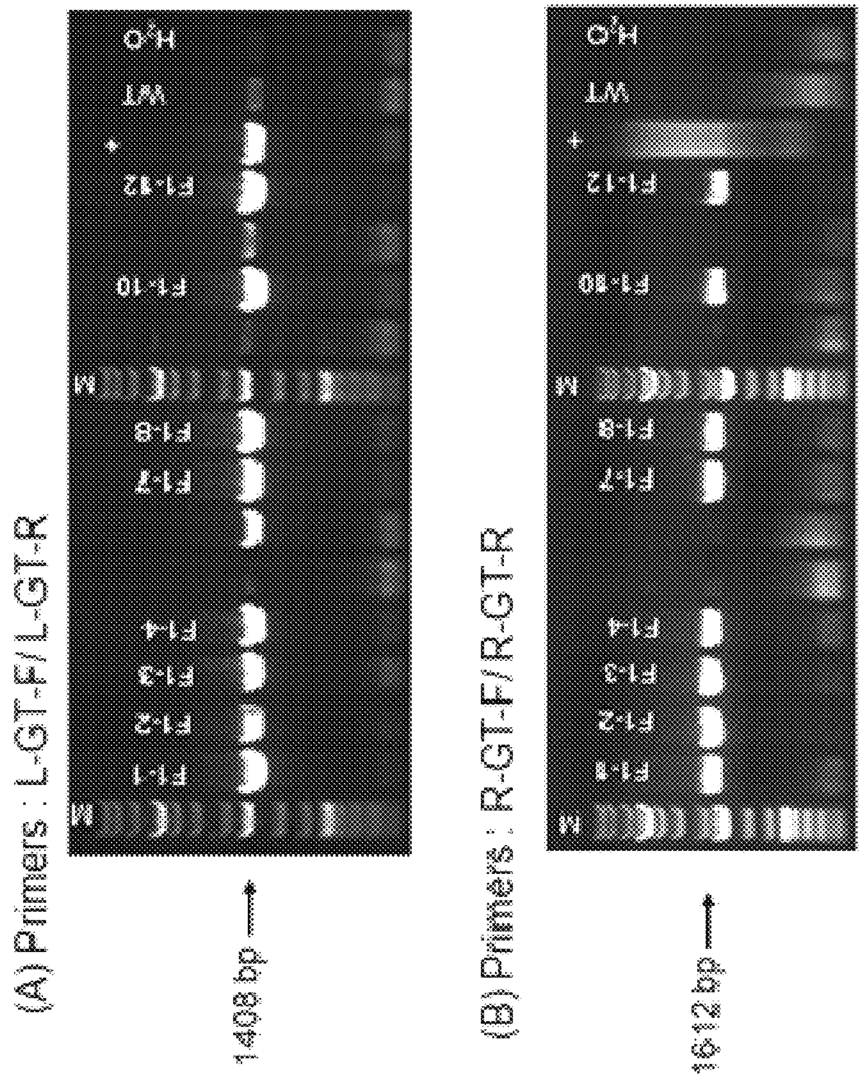
FIGS. 6A-6B show PCR identification results of samples collected from tails of F1 generation C57BL/6 mouse. WT is wildtype; + is positive control. Mice labeled with F1-1, F1-2, F1-3, F1-4, F1-7, F1-8, F1-10, F1-12 are positive.

Results for humanized mice in C57BL/6 background are shown in FIG. 6. F1-1, F1-2, F1-3, F1-4, F1-7, F1-8, F1-10, and F1-12 had the correct sized PCR products and thus were positive.

Figures 7A, 7B:
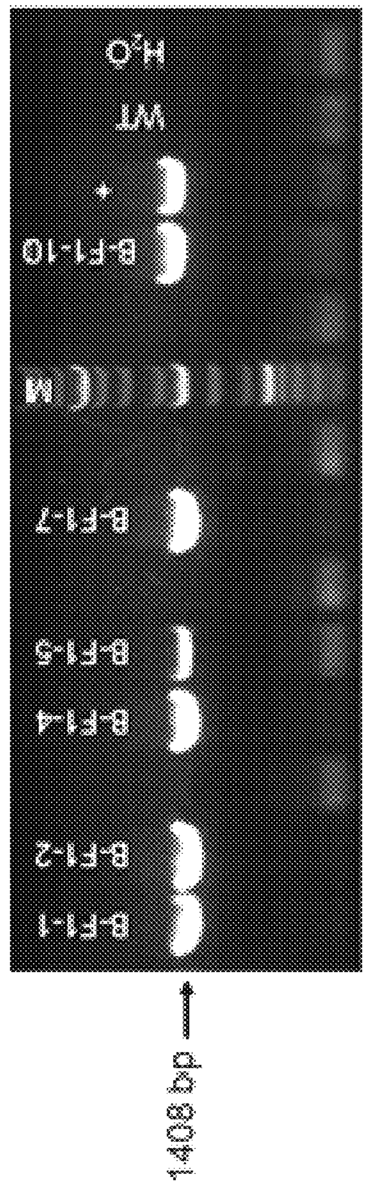
FIGS. 7A-7B show PCR identification results of samples collected from tails of F1 generation BALB/c mouse. WT is wildtype; + is positive control. Mice labeled with B-F1-1, B-F1-2, B-F1-4, B-F1-5, B-F1-7, and B-F1-10 are positive.

Results for humanized mice in BALB/c background are shown in FIG. 7. B-F1-1, B-F1-2, B-F1-4, B-F1-5, B-F1-7, and B-F1-10 had the correct sized PCR products and thus were positive.

These results show that the method described herein can be used to generate humanized CD47 mice with stable and inheritable genetic modifications.

3. Expression Level Analysis in Humanized Mice

A humanized heterozygous F1 generation mouse was selected. Two wildtype mice in the same background were used as controls.

7.5 μg of mouse anti-CD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS and RT-PCR.

Figure 8B:
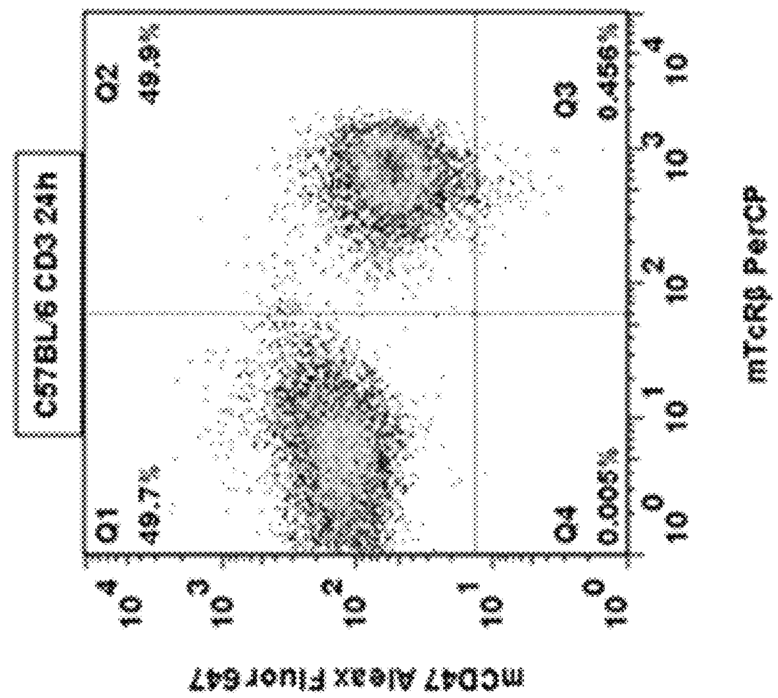
FIGS. 8A-8F are flow cytometry results of wildtype C57BL/6 mice (FIGS. 8A, 8B, 8D, and 8E) and humanized CD47 mice F1 generation in C57BL/6 background (FIGS. 8C, 8F). CD3 antibody was used to activate spleen cells in FIGS. 8B, 8C, 8E, 8F. Flow cytometry was performed with 1) antibody against mouse CD47 (mCD47 Alexa Fluor 647) and antibody against mouse TcRβ (mTcRβ PerCP) (FIGS. 8A-8C); and 2) antibody against human CD47 (hCD47 PE), and antibody against mouse TcRβ (mTcRβ PerCP) (FIGS. 8D-8F). In the control groups, no spleen cells stained with hCD47 PE were observed in C57BL/6 mice (FIGS. 8D and 8E); in humanized CD47 groups, spleen cells stained with hCD47 PE were observed in heterozygous humanized CD47 mice (FIG. 8F).
Figure 8A:
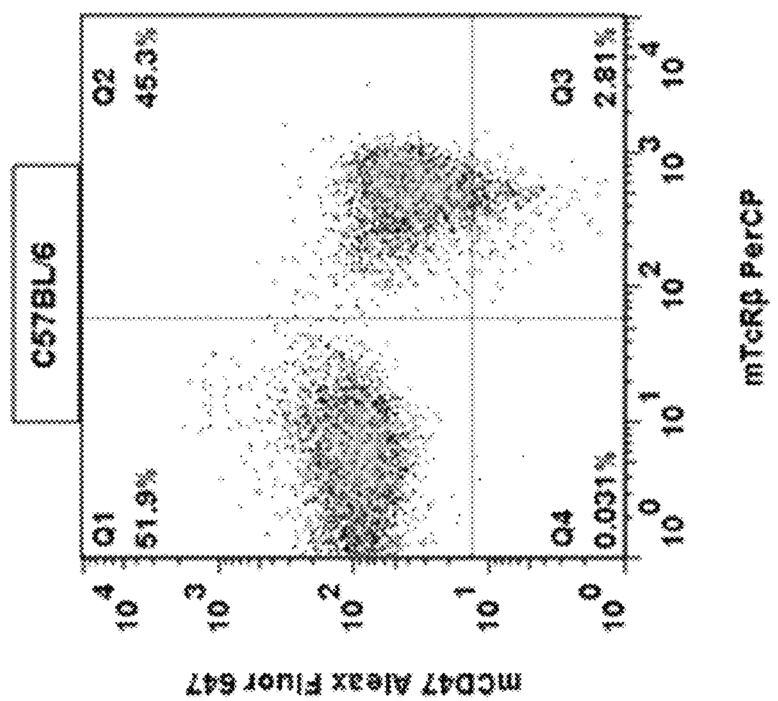
Figure 8D:
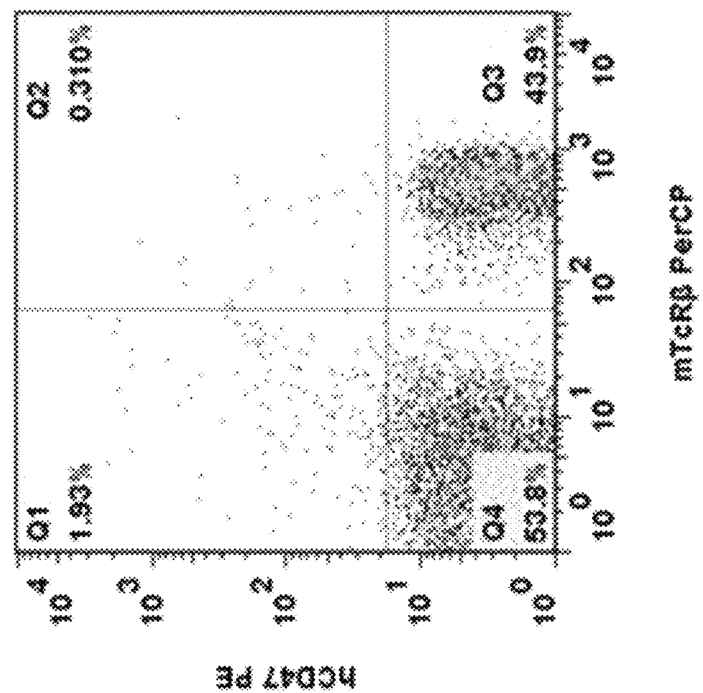
Figure 8C:
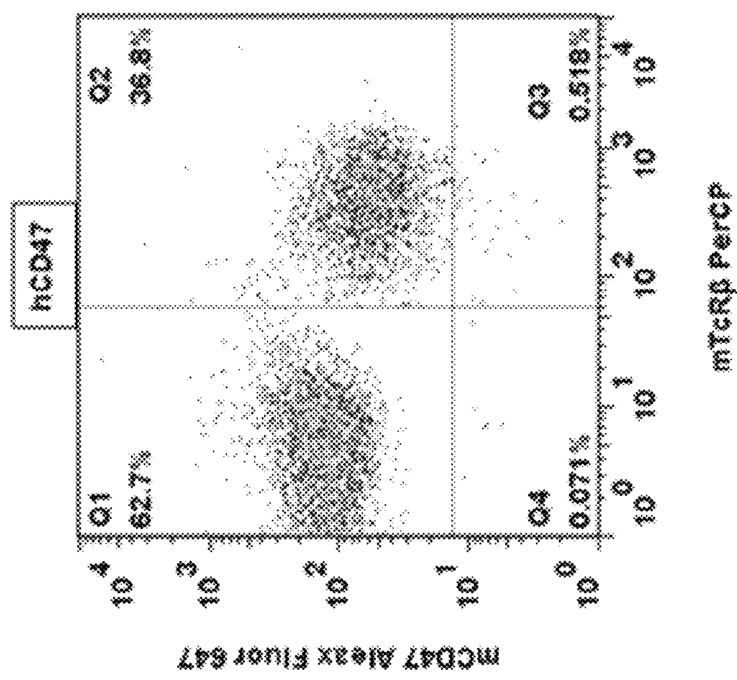
Figure 8F:
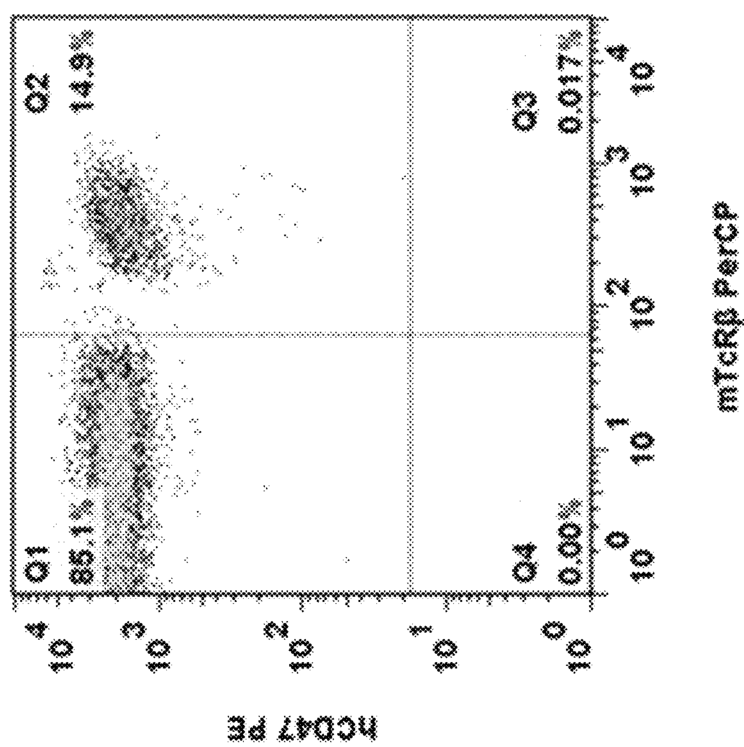
Figure 8E:
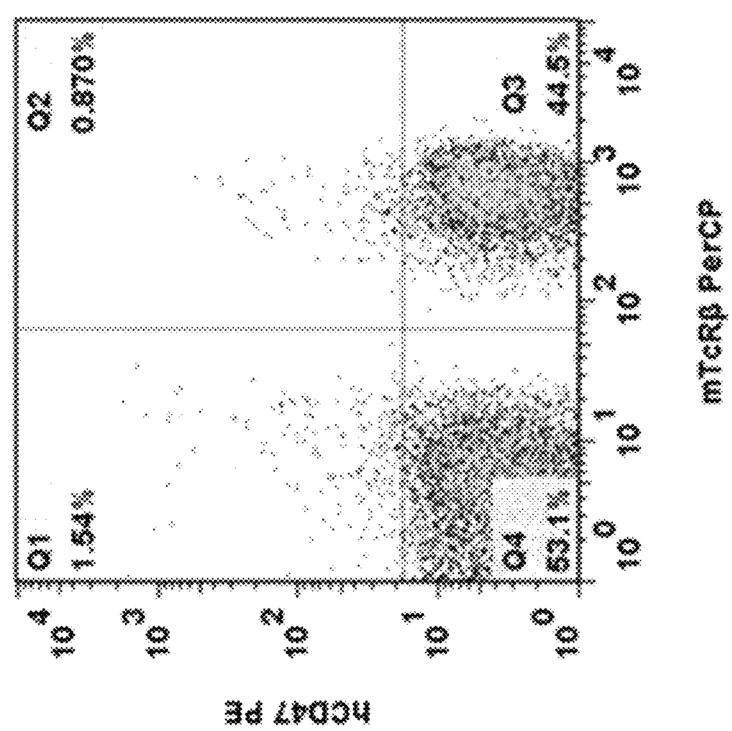

FACS: Flow cytometry was performed with wildtype C57BL/6 mice (FIGS. 8A, 8B, 8D, and 8E) and humanized CD47 mice F1 generation in C57BL/6 background (FIGS. 8C, 8F). CD3 antibody was used to activate spleen cells in FIGS. 8B, 8C, 8E, 8F. Flow cytometry was performed with 1) antibody against mouse CD47 (mCD47 Alexa Fluor 647) and antibody against mouse TcRβ (mTcRβ PerCP) (FIGS. 8A-8C); and 2) antibody against human CD47 (hCD47 PE), and antibody against mouse TcRβ (mTcRβ PerCP) (FIGS. 8D-8F). In the control groups, no spleen cells stained with hCD47 PE were observed in C57BL/6 mice (FIGS. 8D and 8E); in humanized CD47 groups, spleen cells stained with hCD47 PE were observed in heterozygous humanized CD47 mice (FIG. 8F).

Figure 9B:
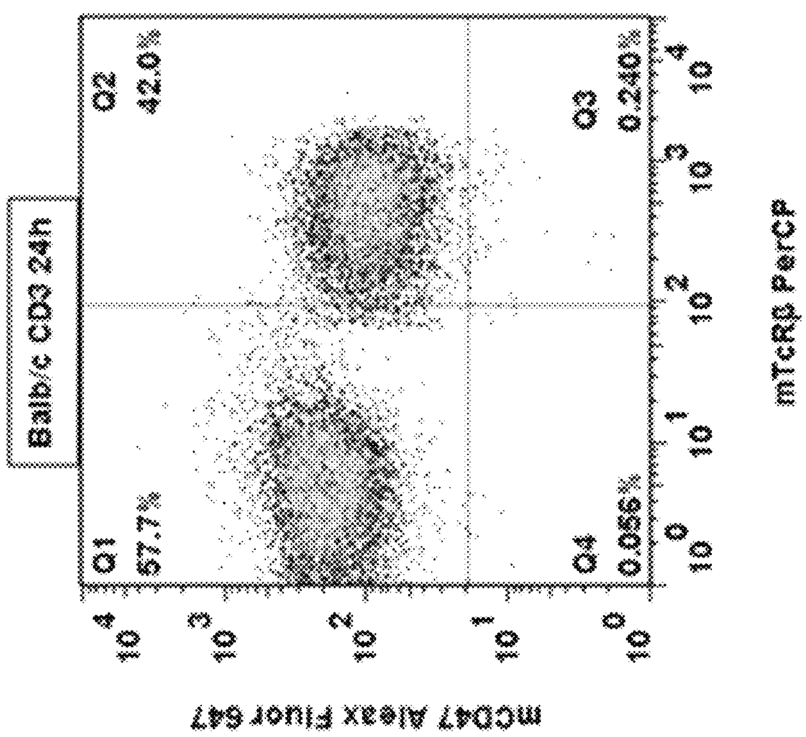
FIGS. 9A-9F are flow cytometry results of wildtype BALB/c mice (FIGS. 9A, 9B, 9D, and 9E) and humanized CD47 heterozygous mice (F1 generation) in BALB/c background (FIGS. 9C, 9F). CD3 antibody was used to activate spleen cells in FIGS. 9B, 9C, 9E and 9F. Flow cytometry was performed with 1) antibody against mouse CD47 (mCD47 Alexa Fluor 647) and antibody against mouse TcRβ (mTcRβ PerCP) (FIGS. 9A-9C); and 2) antibody against human CD47 (hCD47 PE), and antibody against mouse TcRβ (mTcRβ PerCP) (FIGS. 9D-9F). In the control groups, no spleen cells stained with hCD47 PE were observed in BALB/c mice (FIGS. 9D and 9E); in humanized CD47 groups, spleen cells stained with hCD47 PE were observed in the heterozygous humanized CD47 mice (FIG. 9F).
Figure 9A:
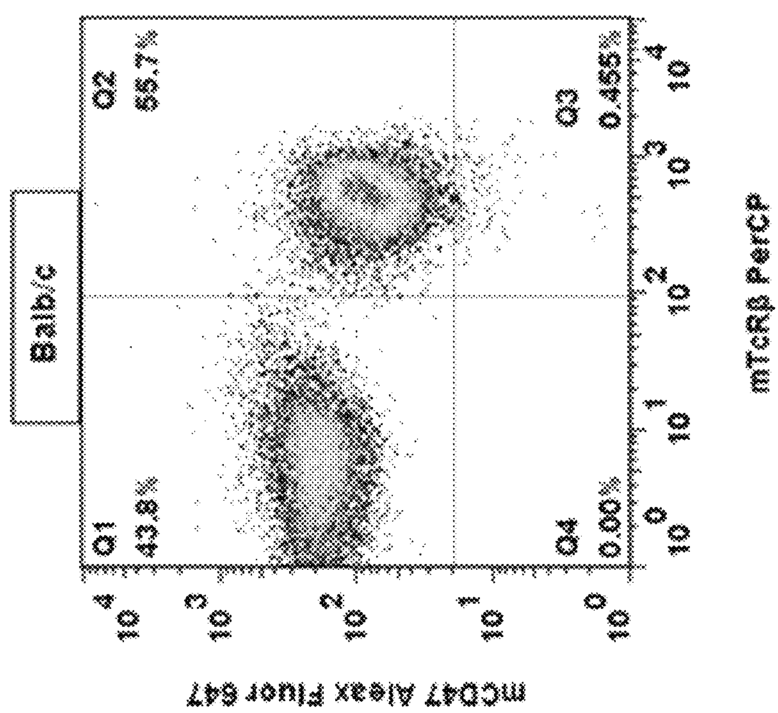
Figure 9D:
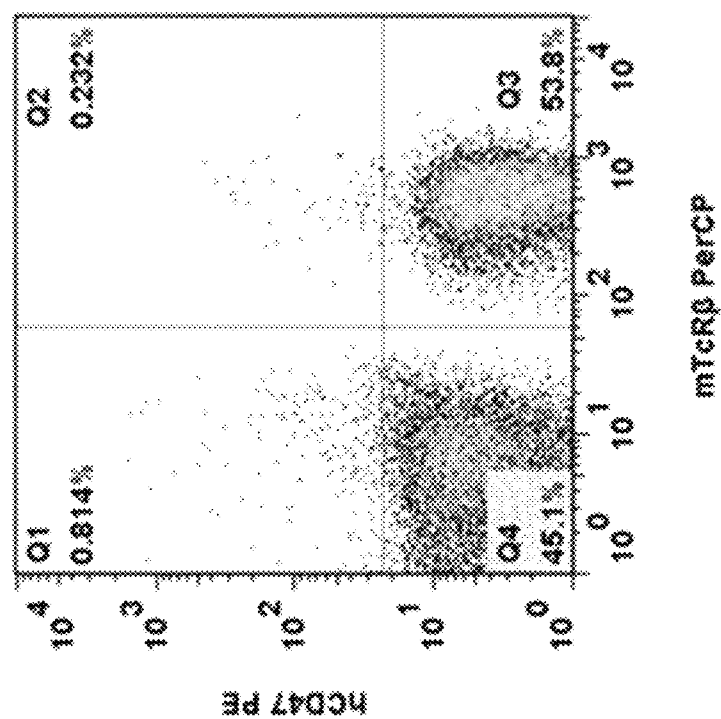
Figure 9C:
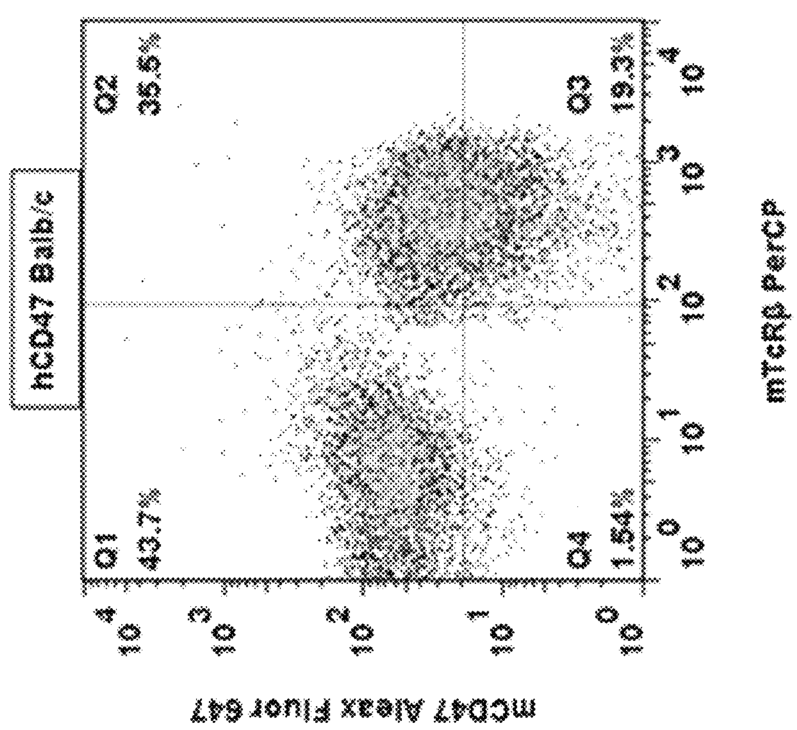
Figure 9F:
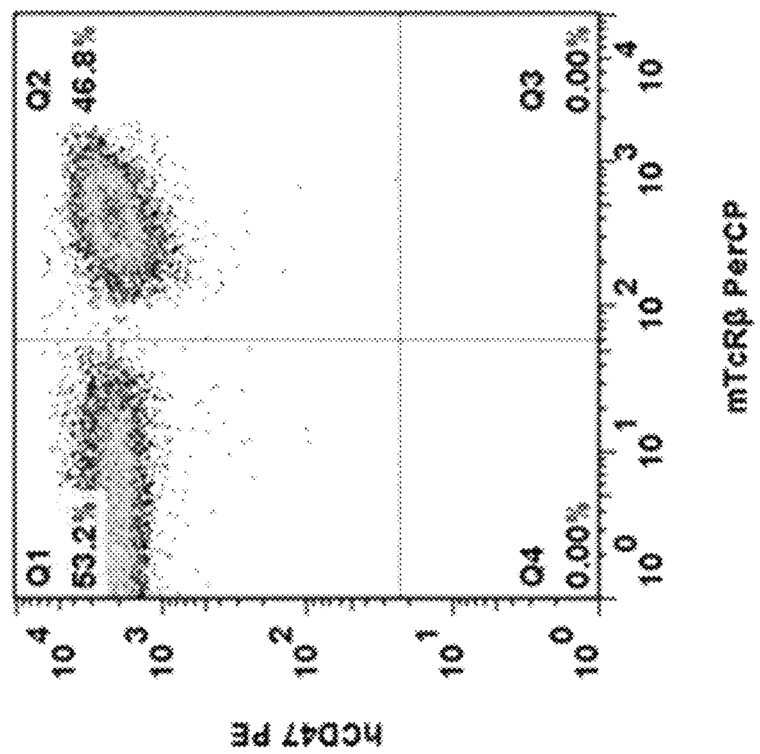
Figure 9E:
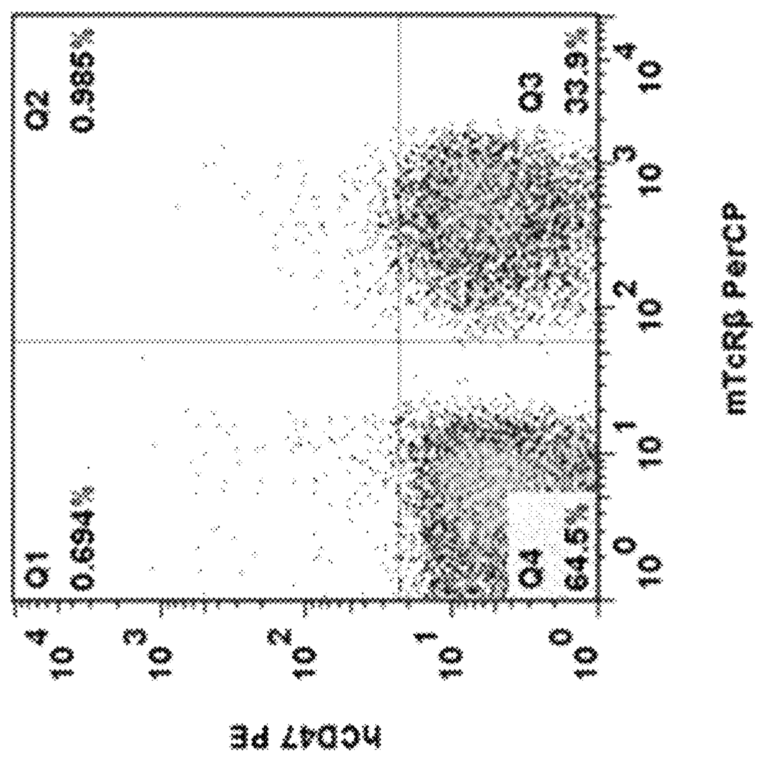

Flow cytometry was also performed with wildtype BALB/c mice (FIGS. 9A, 9B, 9D, and 9E) and humanized CD47 heterozygous mice (F1 generation) in BALB/c background (FIGS. 9C, 9F). CD3 antibody was used to activate spleen cells in FIGS. 9B, 9C, 9E and 9F. Flow cytometry was performed with 1) antibody against mouse CD47 (mCD47 Alexa Fluor 647) and antibody against mouse TcRβ (mTcRβ PerCP) (FIGS. 9A-9C); and 2) antibody against human CD47 (hCD47 PE), and antibody against mouse TcRβ (mTcRβ PerCP) (FIGS. 9D-9F). In the control groups, no spleen cells stained with hCD47 PE were observed in BALB/c mice (FIGS. 9D and 9E); in humanized CD47 groups, spleen cells stained with hCD47 PE were observed in the heterozygous humanized CD47 mice (FIG. 9F).

RT-PCR: RT-PCR experiments were performed to confirm the genetic makeup of humanized CD47 mice in C57BL/6 background (FIG. 10A), and BALB/c background (FIG. 10B). mRNA was extracted from spleens of F1 generation mice and reverse-transcribed into cDNA. The primers for the human CD47 (hCD47) mRNA sequence and the mouse CD47 (mCD47) mRNA sequence are as follows:

```
mCD47 RT-PCR F2:
                                   (SEQ ID NO: 39)
5' -GTCATCCCTTGCATCGTCCG-3'

mCD47 RT-PCR R2:
                                   (SEQ ID NO: 40)
5' - ACTTCGCAAGTGTAGTTTCCCA-3'
```

-continued

```
hCD47 RT-PCR F1:
                                    (SEQ ID NO: 41)
5' - ACACTGTCGTCATTCCATGCT-3'

hCD47 RT-PCR R1:
                                    (SEQ ID NO: 42)
5' -CCTGTGTGTGAGACAGCATCA-3'
```

The primers targeting mouse CD47 sequence should produce a PCR band of about 230 bp. The primers targeting human CD47 sequence should yield a PCR band of about 226 bp in humanized CD47 mice.

A 20 μL PCR system was used under the conditions of: 95° C., 5 mins; 35 cycles of the conditions 95° C., 30 sec, 60° C., 30 sec, 72° C., 30 sec; 72° C., 10 mins; storing at 4° C. GAPDH was used as an internal control.

Figures 10A, 10B:
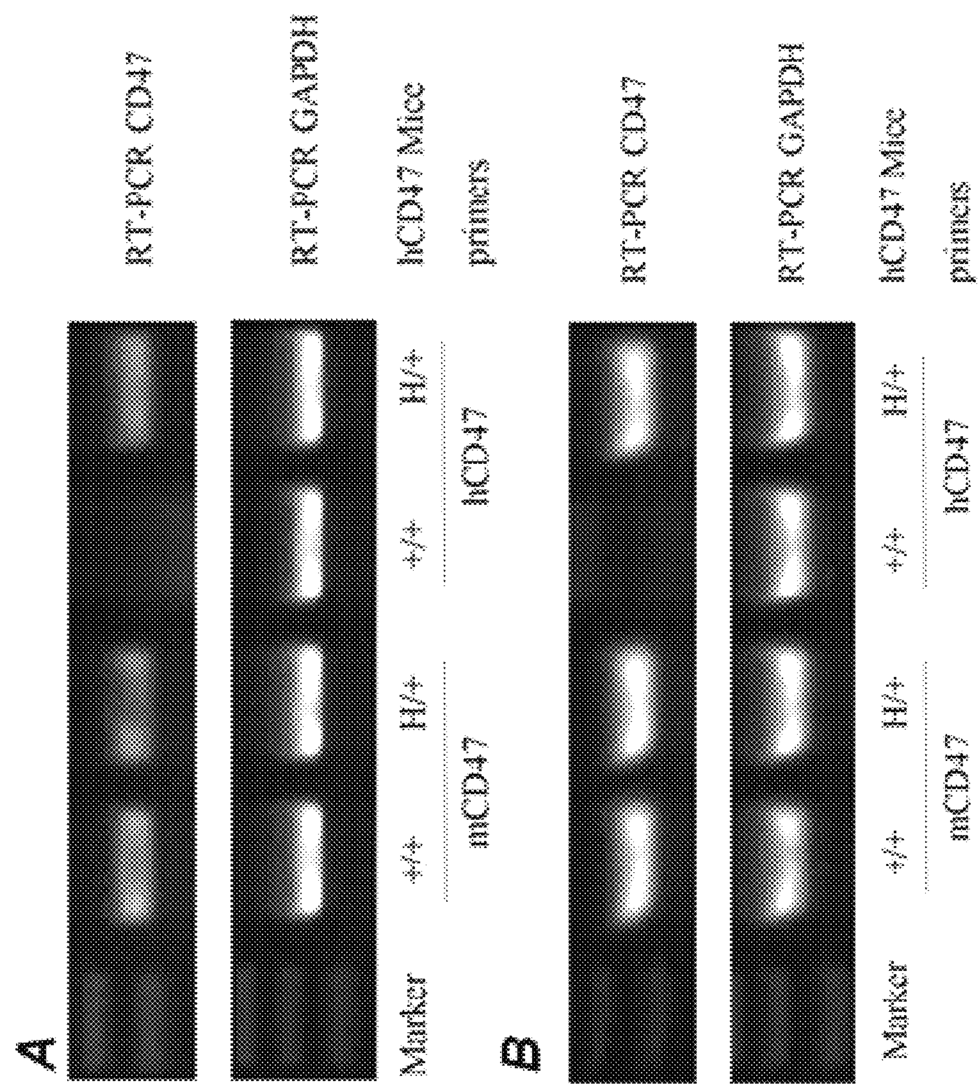
FIGS. 10A-10B show results from RT-PCR experiments using primers targeting human CD47 (hCD47) mRNA sequence and mouse CD47 (mCD47) mRNA sequence in heterozygous humanized CD47 mice (F1 generation) in C57BL/6 background (FIG. 10A), and in humanized CD47 mice (F1 generation) in BALB/c background (FIG. 10B). +/+ indicates wildtype mice; H/+ indicates the F1 generation mouse that is heterozygous for humanized CD47; and GAPDH was used as a control.
Figure 11B:
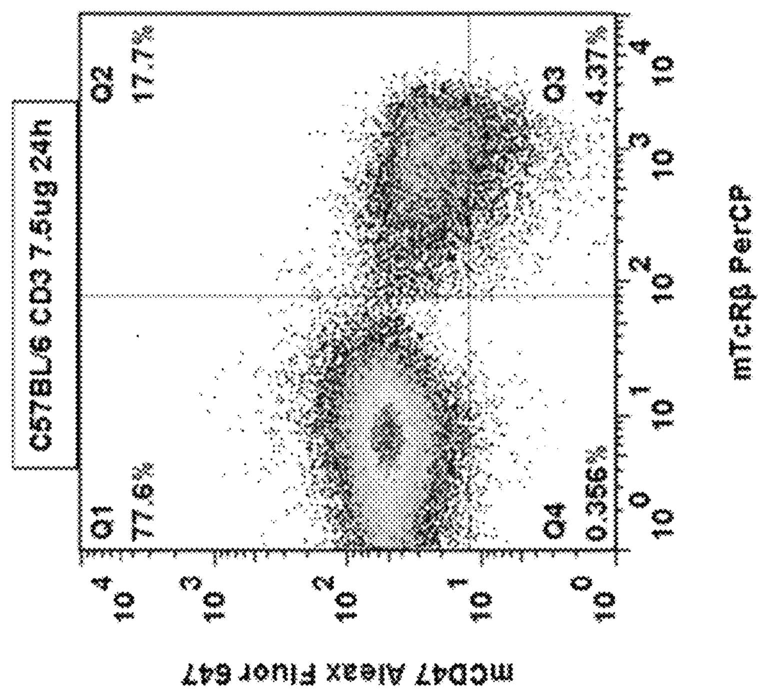
FIGS. 11A-11F are flow cytometry results of wildtype C57BL/6 mice (FIGS. 11A, 11B, 11D, and 11E) and humanized CD47 homozygous mice in C57BL/6 background (FIGS. 11C, 11F). CD3 antibody was used to activate spleen cells in FIGS. 11B, 11C, 11E and 11F. Flow cytometry was performed with 1) antibody against mouse CD47 (mCD47 Alexa Fluor 647) and antibody against mouse TcRβ (mTcRβ PerCP) (FIGS. 11A-11C); and 2) antibody against human CD47 (hCD47 PE), and antibody against mouse TcRβ (mTcRβ PerCP) (FIGS. 11D-11F). In the control groups, no spleen cells stained with hCD47 PE were observed in C57BL/6 mice (FIGS. 11D and 11E); in humanized CD47 groups, spleen cells stained with mCD47 Alexa Fluor 647 were not observed (FIG. 11C), while spleen cells stained with hCD47 PE were observed in the homozygous humanized CD47 mice (FIG. 11F).
Figure 11A:
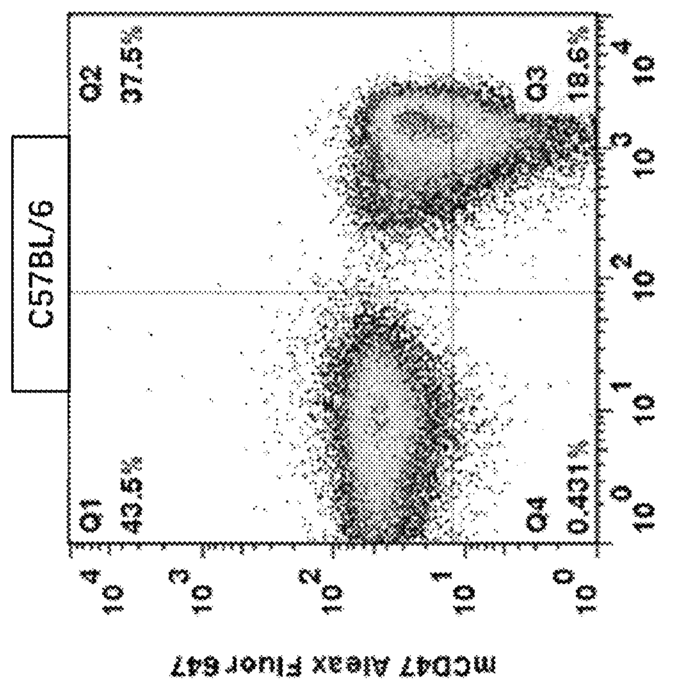
Figure 11D:
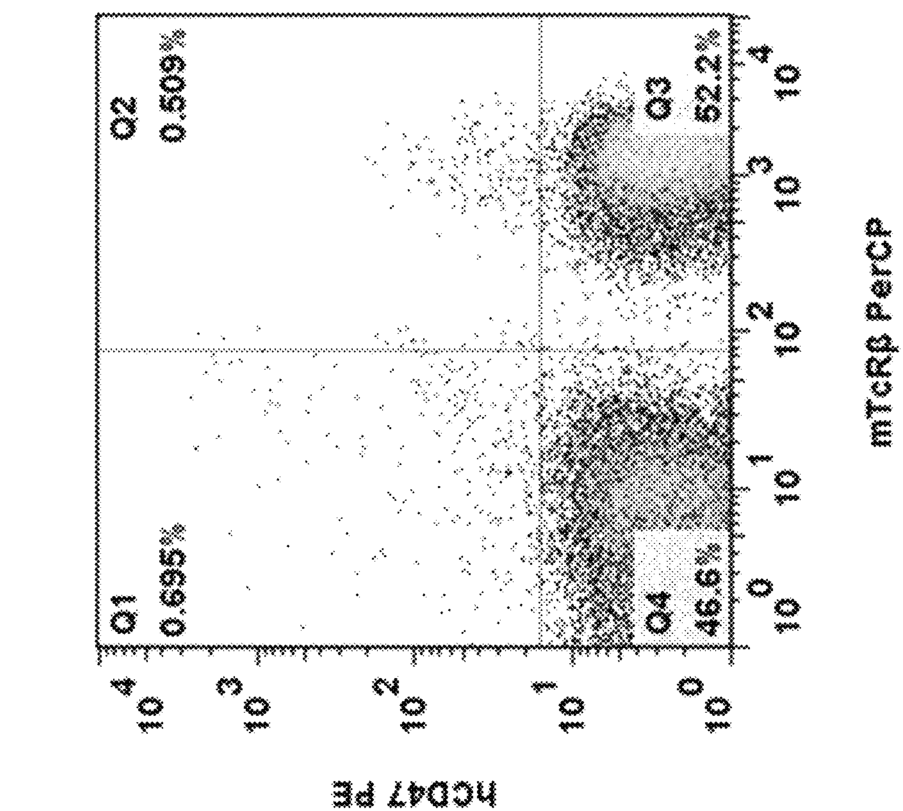
Figure 11C:
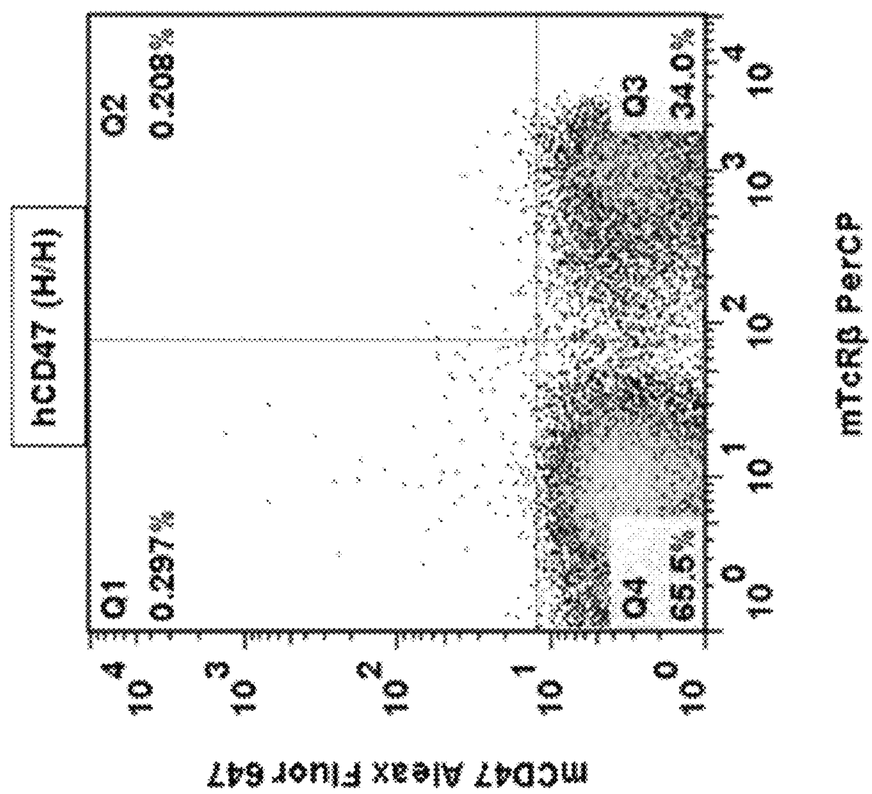
Figure 11F:
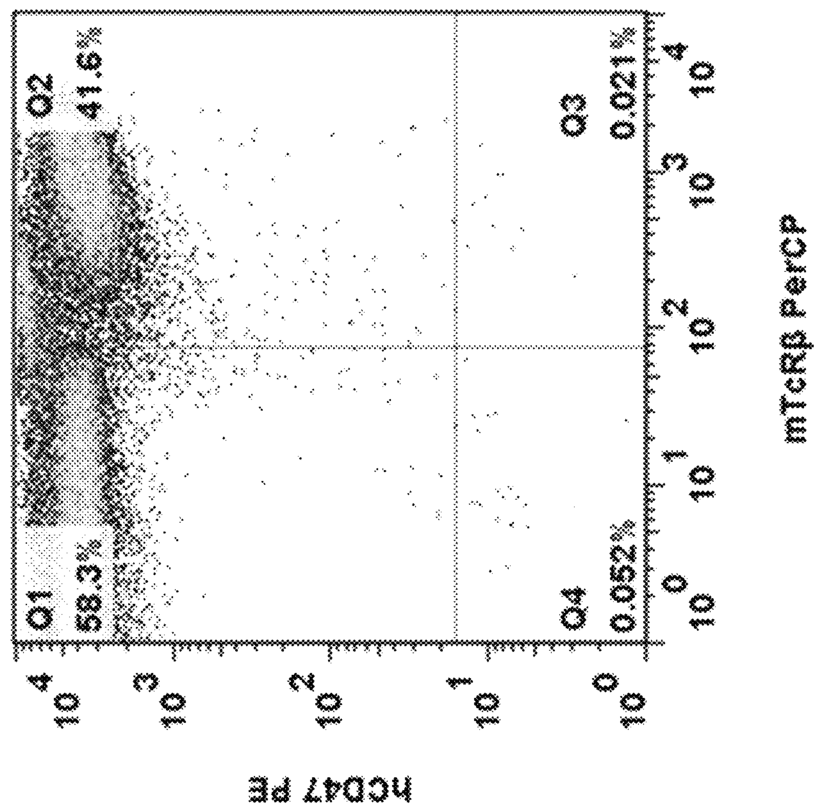
Figure 11E:
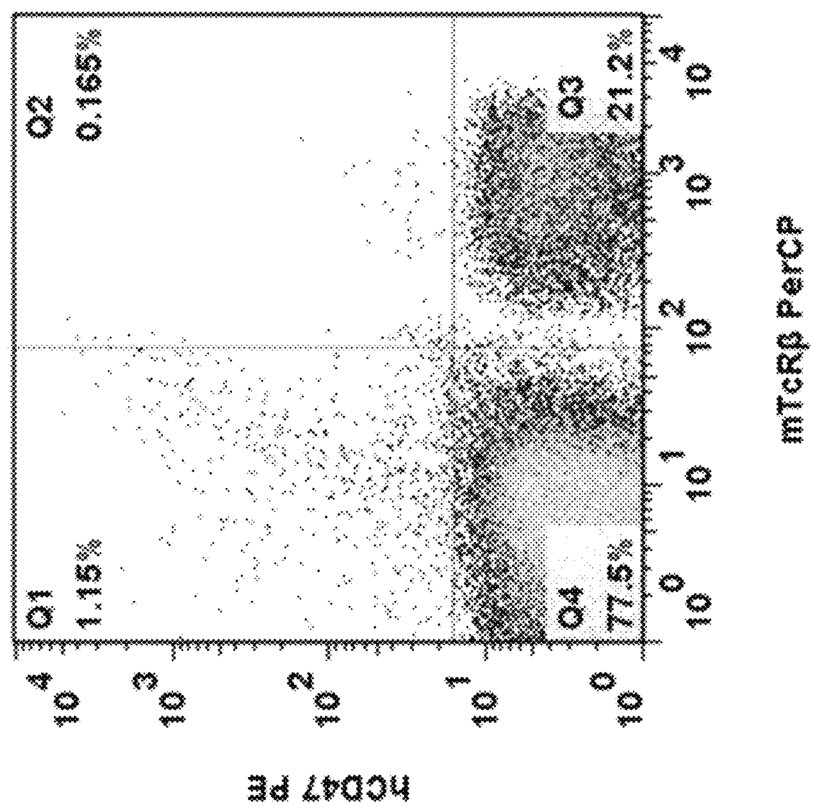
Figure 12:
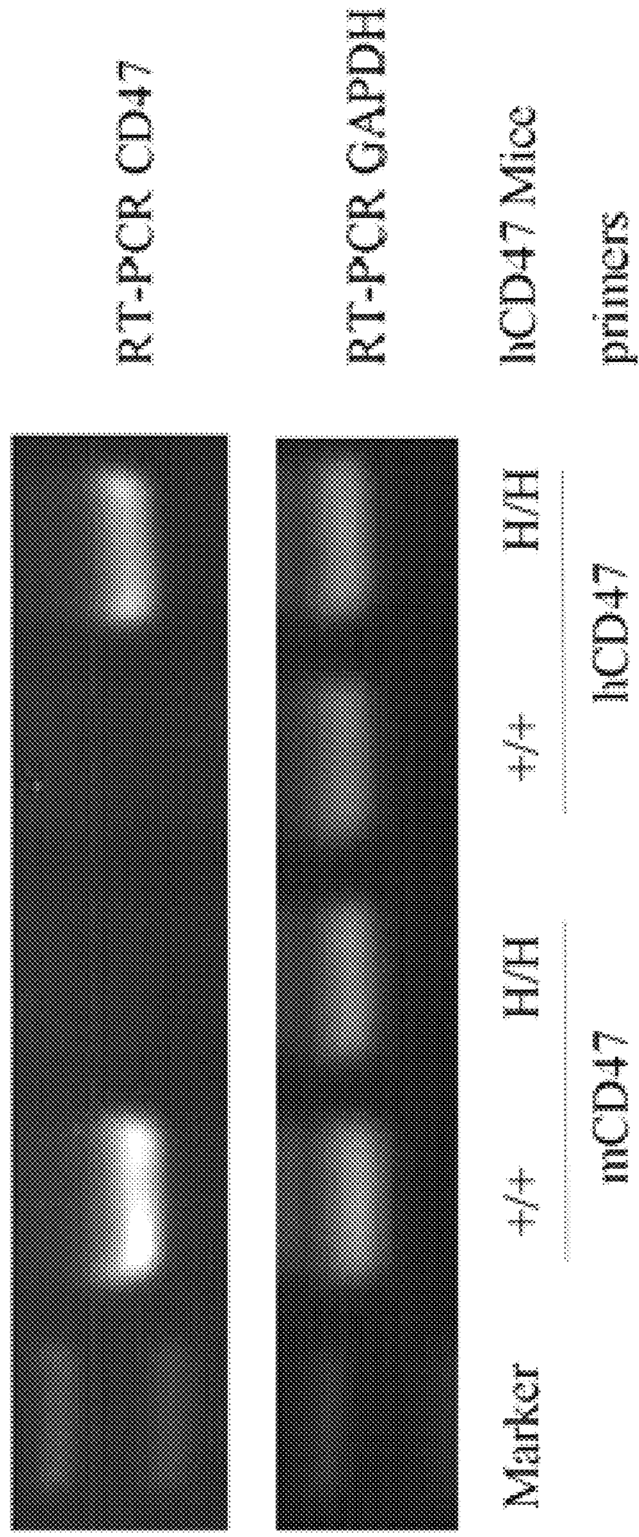
FIG. 12 shows results from RT-PCR experiments amplifying human CD47 (hCD47) and mouse CD47 (mCD47) mRNA in homozygous humanized CD47 mice (F1 generation) in C57BL/6 background. +/+ indicates wildtype mice; H/H indicates that the F1 generation mouse is homozygous for humanized CD47; and GAPDH was used as a control.
Figure 13B:
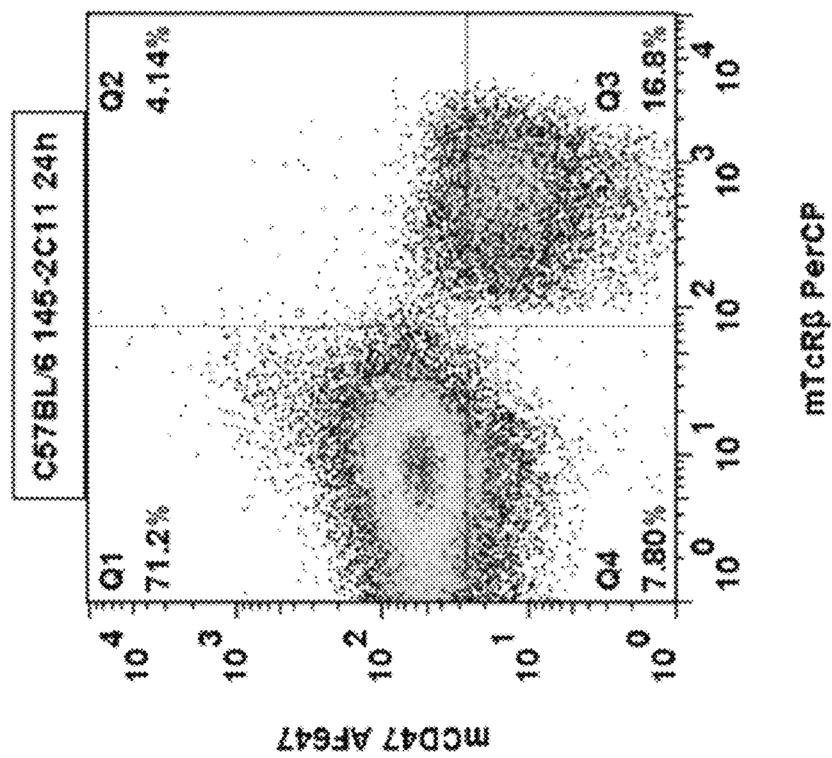
FIGS. 13A-13F are flow cytometry results of wildtype C57BL/6 mice (FIGS. 13A, 13B, 13D, and 13E) and humanized CD47 homozygous mice in BALB/c background (FIGS. 13C, 13F). CD3 antibody was used to activate spleen cells in FIGS. 13B, 13C, 13E and 13F. Flow cytometry was performed with 1) antibody against mouse CD47 (mCD47 Alexa Fluor 647) and antibody against mouse TcRβ (mTcRβ PerCP) (FIGS. 13A-13C); and 2) antibody against human CD47 (hCD47 PE), and antibody against mouse TcRβ (mTcRβ PerCP) (FIGS. 13D-13F). In the control groups, no spleen cells stained with hCD47 PE were observed in wildtype mice (FIGS. 13D and 13E); in humanized CD47 groups, spleen cells stained with mCD47 Alexa Fluor 647 were not observed (FIG. 13C), while spleen cells stained with hCD47 PE were observed in the homozygous humanized CD47 mice (FIG. 13F).
Figure 13A:
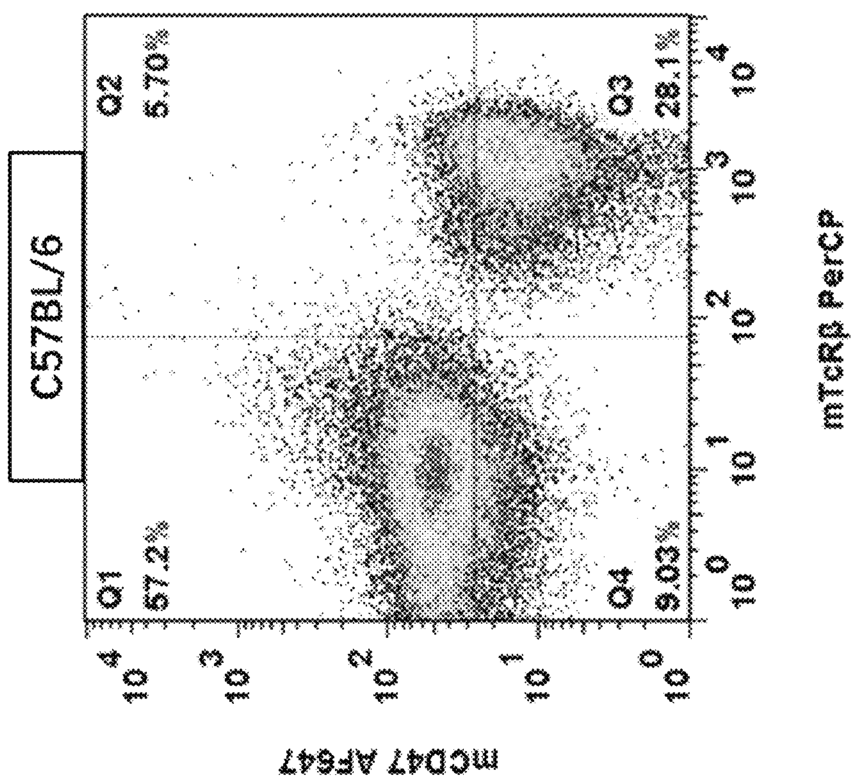
Figure 13D:
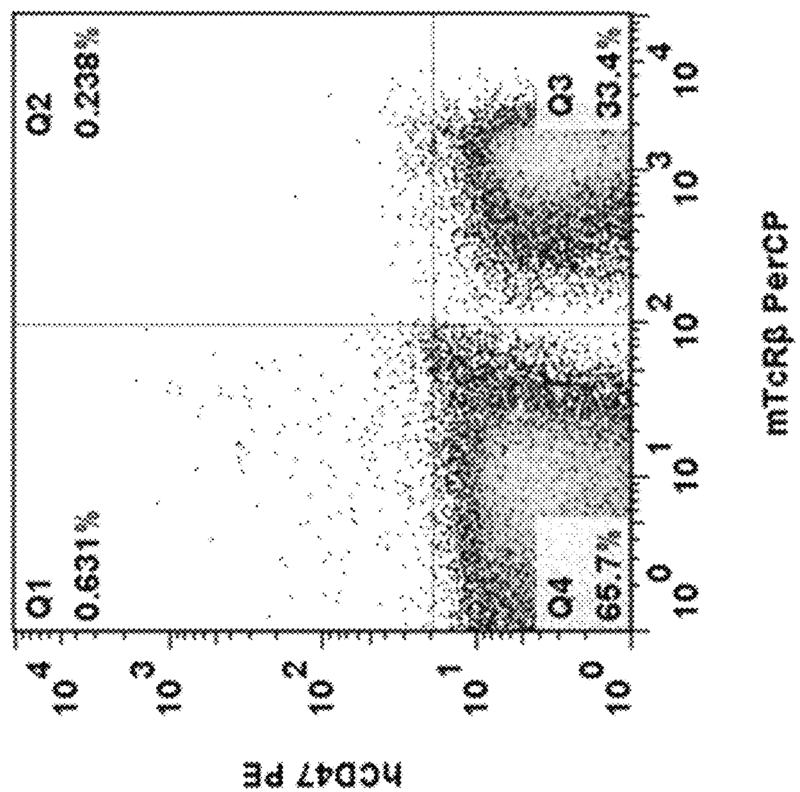
Figure 13C:
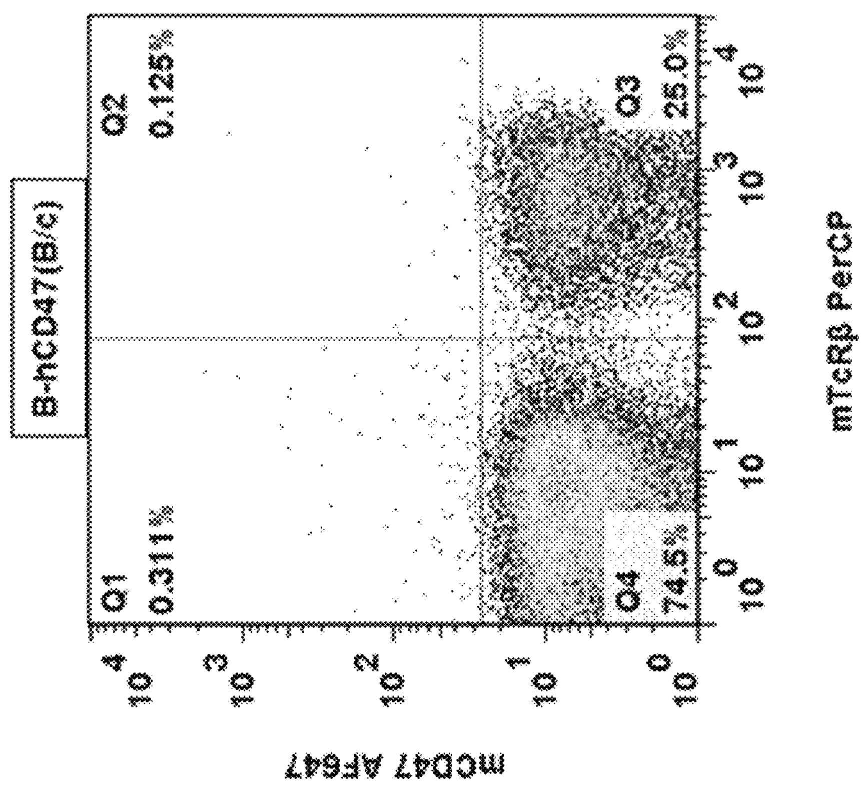
Figure 13F:
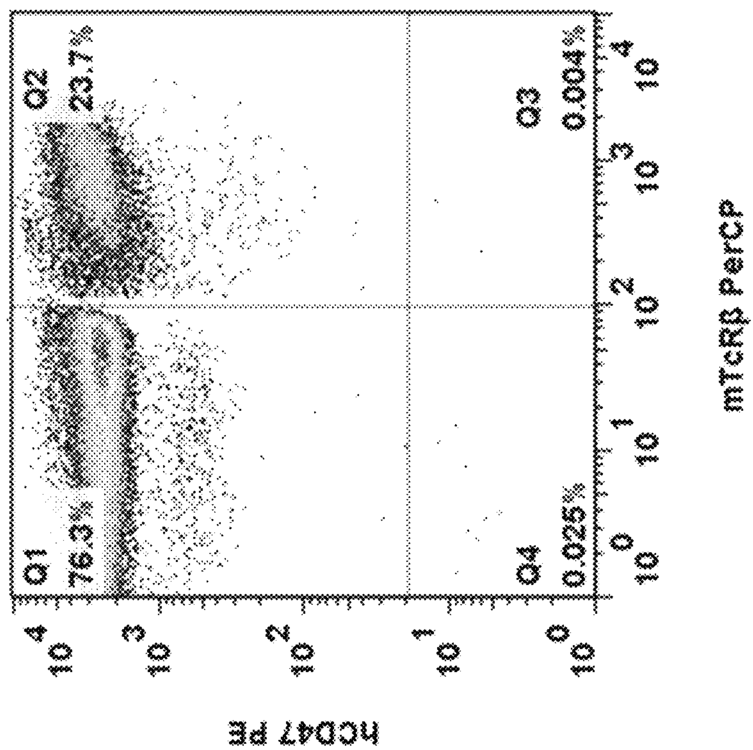
Figure 13E:
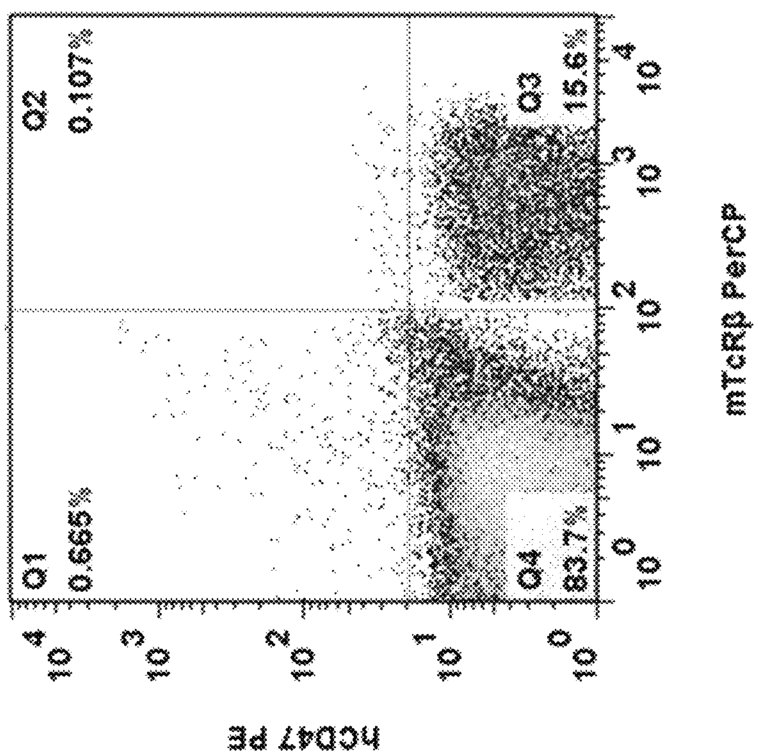
Figure 14:
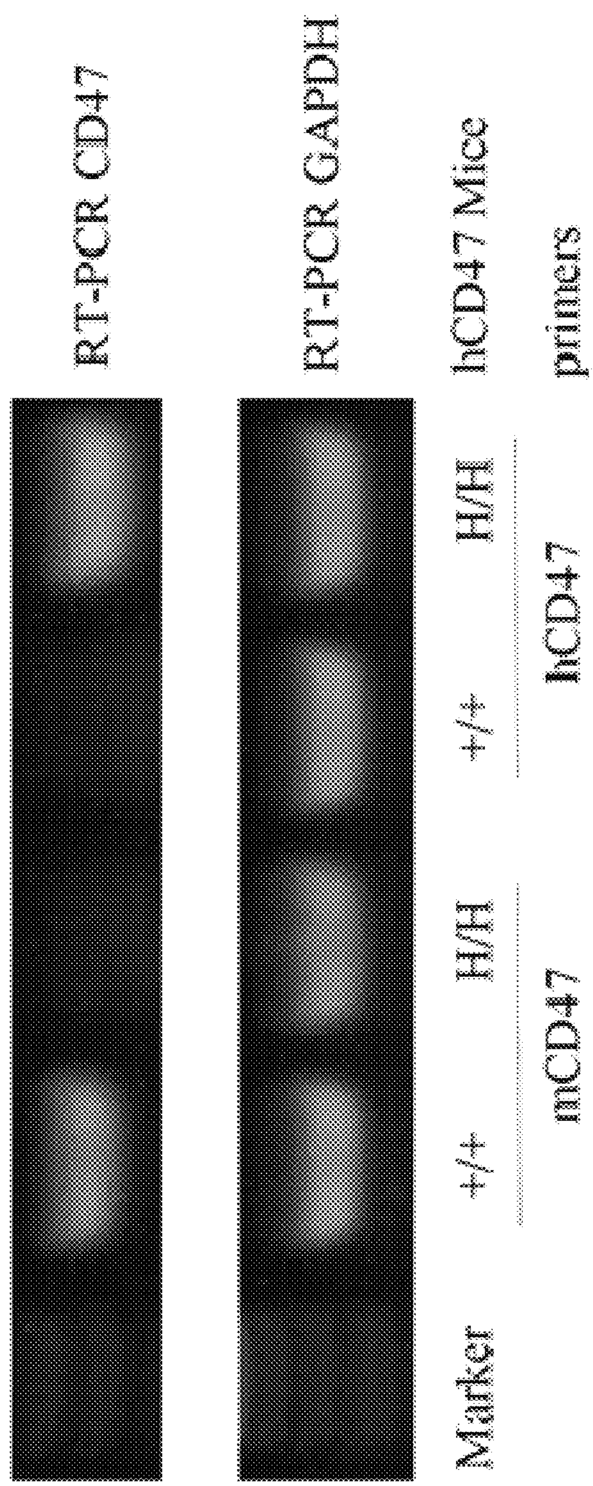
FIG. 14 shows results from RT-PCR experiments amplifying human CD47 (hCD47) and mouse CD47 (mCD47) mRNA in homozygous humanized CD47 mice (F1 generation) in BALB/c background. +/+ indicates wildtype mice; H/H indicates that the F1 generation mouse is homozygous for humanized CD47; and GAPDH was used as a control.

Results for humanized CD47 mice in C57BL/6 background are shown in FIG. 10A. Mouse CD47 mRNA was detected in activated spleen cells of both wildtype C57BL/6 mice and F1 generation humanized CD47 heterozygotes with C57BL/6 background. Human CD47 mRNA sequence was detected in F1 generation humanized CD47 heterozygotes in C57BL/6 background but not in wildtype mice.

Results for humanized CD47 mice in BALB/c background are shown in FIG. 10B. Mouse CD47 mRNA was detected in activated spleen cells of both wildtype BALB/c mice and F1 generation humanized CD47 heterozygotes with BALB/c background. Human CD47 mRNA sequence was detected in F1 generation humanized CD47 heterozygotes with BALB/c background but not in wildtype mice.

The F1 generation humanized CD47 heterozygotes with the same background were mated with each other to produce humanized CD47 homozygotes. The same experiments described above were performed on these humanized CD47 homozygous mice. The FACS and RT-PCR results for humanized CD47 homozygous C57BL/6 mice are shown in FIGS. 11A-11F and FIG. 12. The FACS and RT-PCR results for humanized CD47 homozygous BALB/c mice are shown in FIGS. 13A-13F and FIG. 14.

Example 11: CD47 Knockout Mice

Since the cleavage of Cas9 results in DNA double strands break, and the homologous recombination repair may result in insertion/deletion mutations, it is possible to obtain CD47 knockout mice by the methods described herein. A pair of primers was thus designed to target the left side of the 5' target site and the right side of the 3' target site:

```
F:
                                    (SEQ ID NO: 43)
5' - ggtaaatttatccccaagatgcatggta -3'

                                    (SEQ ID NO: 44)
R: 5' - gccttaattcctcctagtgacttctgc -3'
```

This pair of primers should yield one PCR band with about 698 bp for wildtype mice, one band with about 386 bp for homozygous CD47 knockout mice, and both bands (698 bp+386 bp) for the heterozygous mice.

The PCR reaction systems and conditions are shown in Table 9 and Table 10.

TABLE 9

| | |
|---|---|
| 2 × TSINGKE Master mix | 10 μL |
| Upstream primer (0.2 μM) | 0.5 μL |
| Downstream primer (0.2 μM) | 0.5 μL |
| Genomic DNA from mouse tail | 200 ng |
| $H_2O$ | Add to 20 μL |

TABLE 10

| Temperature | Duration | Cycles |
|---|---|---|
| 94° C. | 5 min | 1 |
| 94° C. | 30 sec | 35 |
| 62° C. | 30 sec | |
| 72° C. | 1 kb/min | |
| 72° C. | 35 sec | |
| 72° C. | 10 min | 1 |
| 4° C. | 10 min | 1 |

Figure 15:
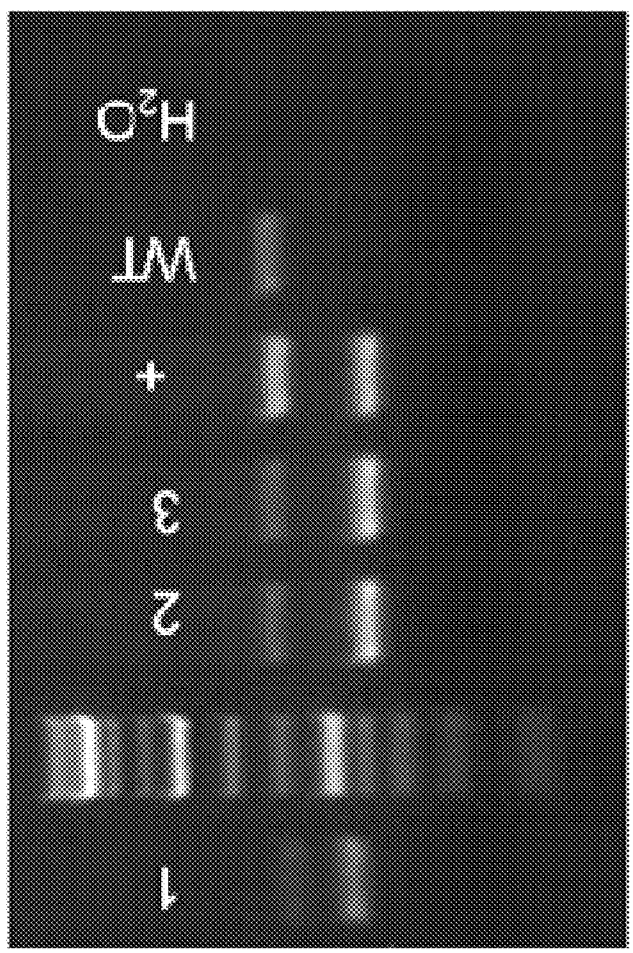
FIG. 15 shows PCR results from CD47 knockout mice in BALB/c background (No. 1 in FIG. 15), and in C57BL/6 background (Nos. 2 and 3 in FIG. 15). WT indicates wildtype. + is positive control.

FIG. 15 shows the PCR results. The mouse numbered 1 was in BALB/c background, and had a band at approximately 386 bp, and was thus a CD47 knockout heterozygous mouse. The mice numbered 2 and 3 were in C57BL/6 background, and had bands at approximately 386 bp, and thus were CD47 knockout heterozygous mice.

Example 12: Testing Toxicity Using Humanized CD47 Mouse Model

CD47 is expressed on the surface of nearly all kinds of cells, especially in large amount on erythrocytes. Because antibodies against human CD47 do not bind to mouse CD47, the mouse model that are generally used cannot be used to test toxicity of therapeutic agents targeting human CD47. The humanized CD47 mice described herein express humanized CD47 protein, and anti-hCD47 antibodies can bind to CD47 in the humanized mice and block the transduction of the protective signal. Because erythrocytes express a large amount of CD47 on their surface, the binding of anti-CD47 antibodies blocks the CD47/SIRPα signaling pathway, resulting in apoptosis of erythrocytes and in more serious cases resulting in death of the mice. The humanized CD47 mouse model as described herein can also be used to test the toxicity of the antibodies.

In BALB/c mice, the mouse SIRPα protein (mSIRPα) can bind to humanized CD47 protein. The humanized CD47 mice with BLAB/c background can thus be used to test the toxicity of anti-hCD47 antibodies, the blocking effects of the antibodies, and the effects on antibody-dependent cellular phagocytosis (ADCP).

Homozygous humanized CD47 mice in C57BL/6 background at the age of 7-9 weeks were intraperitoneally administered with either an antibody against human CD47 (treatment group, two mice in each treatment group), or physiological saline solution (control group, two mice in this group). There were seven treatment groups (n=2 in each group), and each group was injected with a randomly selected anti-hCD47 antibody (Ab1-Ab6) at 10 mg/kg. The injections were done in 24 hours after placing the mice into the treatment groups and the control group. The mice were then monitored and weighed daily. Any mouse with more than 20% weight loss was euthanized.

Figure 16:
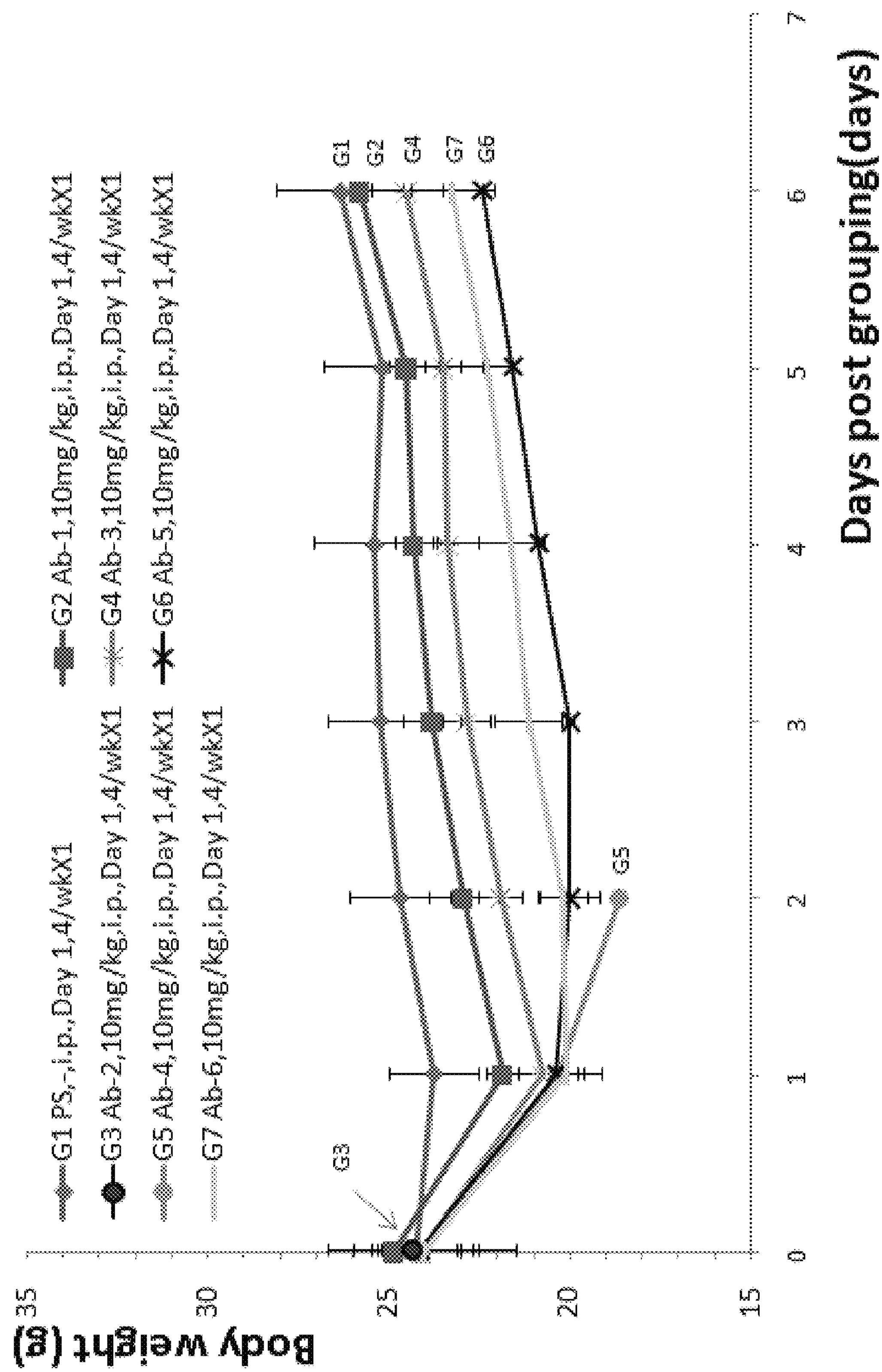
FIG. 16 shows toxicity testing results using homozygous CD47 mice. Six anti-human-CD47 (anti-hCD47) antibodies were injected into humanized CD47 homozygous mice.

The results are shown in FIG. 16, showing that mice in different groups had different weight change. The results demonstrated that different anti-hCD47 antibodies had different toxicities in mice. The Ab-2 and Ab-4 antibodies had the strongest toxicity and the mice in the two groups died within a few days after administration.

Example 13: Mice with Two or More Humanized Genes

Mice with the humanized CD47 gene (e.g., animal model with humanized CD47 prepared using the methods as described in the present disclosure) can also be used to prepare an animal model with double-humanized or multi-humanized genes. For example, in Example 8 or Example 9, the embryonic stem cell used in the microinjection and embryo transfer process can be selected from the embryos of other genetically modified mice, so as to obtain double- or multiple-gene modified mouse models. The fertilized eggs of B-hCD47 mice can also be further genetically engineered to produce mouse lines with one or more humanized or otherwise genetically modified mouse models. In addition, the humanized CD47 animal model homozygote or heterozygote can be mated with other genetically modified homozygous or heterozygous animal models (or through IVF), and the progeny can be screened. According to the Mendelian law, there is a chance to obtain the double-gene or multiple-gene modified heterozygous animals, and then the heterozygous animals can be mated with each other to finally obtain the double-gene or multiple-gene modified homozygotes.

In the case of generating double humanized CD47/SIRPα mice, since the mouse CD47 gene and SIRPα gene are located on different chromosomes, the double humanized CD47/SIRPα mouse model was obtained by crossing the CD47 humanized mice with SIRPα humanized mice.

Figures 17A, 17B, 17C, 17D:
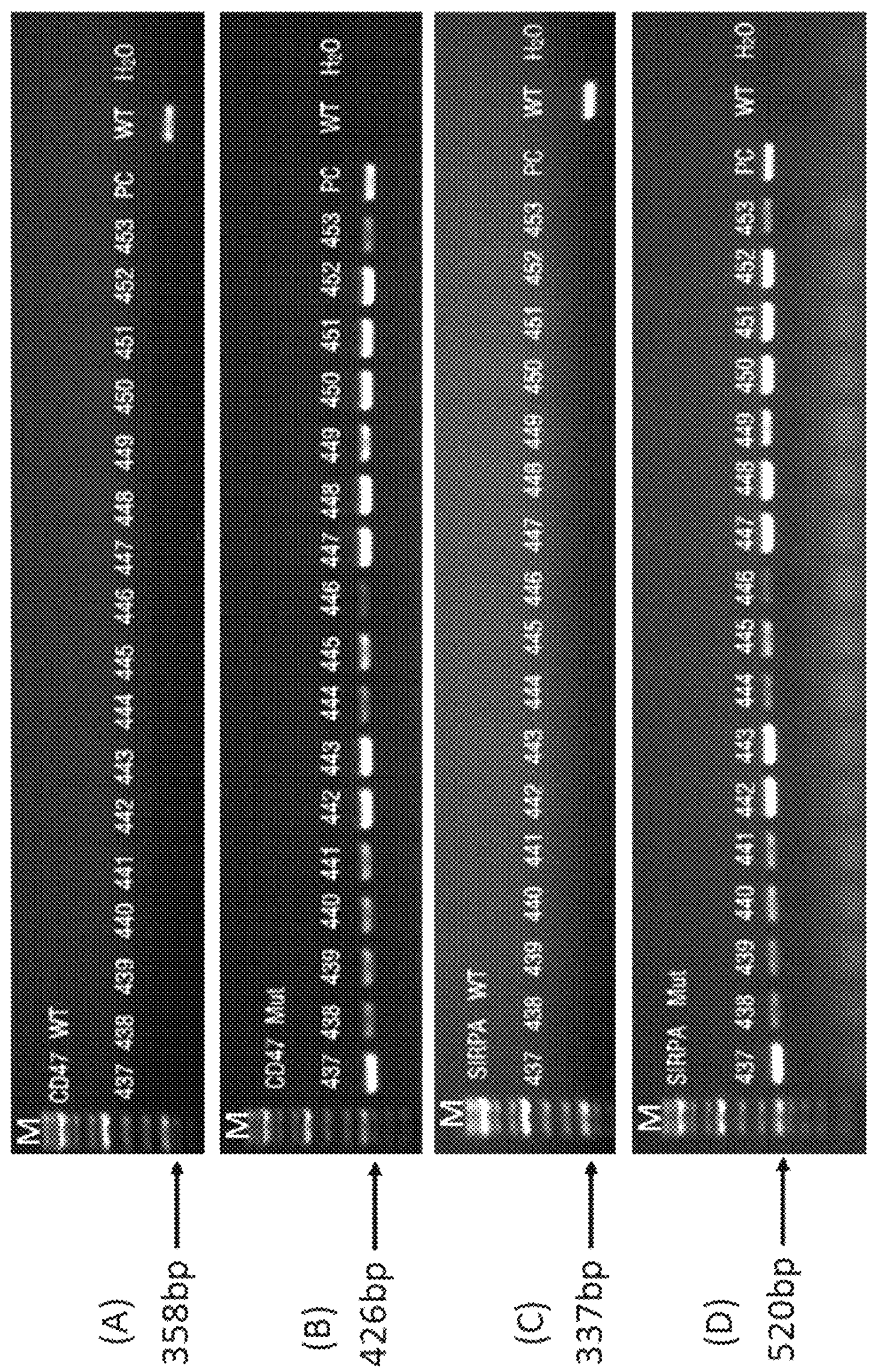
FIGS. 17A-17D show results from PCR confirming that humanized mice are homozygous for humanized CD47. WT indicates wildtype. PC is positive control.

PCR analysis was performed on the genomic DNA collected from mouse tails of double humanized CD47/SIRPα mice. Four pairs of primers were used. The specific sequences and product lengths are shown in the table below. The reaction system and reaction conditions are shown in Table 12 and Table 13. The results for a number of humanized CD47/SIRPα mice are shown in FIGS. 17A-17B, wherein FIGS. 17A and 17B show that the mice numbered 437-453 were homozygous for humanized CD47. FIGS. 17C and 17D show that the mice numbered 437-453 were homozygous for humanized SIRPα. The combined results show that the mice numbered 437-453 were homozygous for both humanized CD47 and humanized SIRPα.

TABLE 11

Primer sequences

| Primer | Sequence | Product length |
|---|---|---|
| CD47 WT | F: 5'- ggtaaatttatccccaagatgcatggta -3' (SEQ ID NO: 43)<br>R: 5'- acaaacatttcttcggtgctttgcg -3' (SEQ ID NO: 81) | WT: 358 bp |
| CD47 MUT | F: 5'- ggtaaatttatccccaagatgcatggta -3' (SEQ ID NO: 43)<br>R: 5'- tggggacagtggacttgtttagagc -3' (SEQ ID NO: 36) | Mut: 426 bp |
| SIRPα WT | F: 5'- gtcttgagttacaggctcatgtgggg -3' (SEQ ID NO: 82)<br>R: 5'- cgaggaacgtattctcctgcgaaac -3' (SEQ ID NO: 83) | WT: 337 bp |
| SIRPα MUT | F: 5'- agctatgtggcttagcactctgtgc -3' (SEQ ID NO: 84)<br>R: 5'- cttaaactccacgtcatcggggctc -3' (SEQ ID NO: 85) | Mut: 520 bp |

TABLE 12

PCR reaction system

| Composition | Volume |
|---|---|
| 2 × Master Mix | 10 μL |
| Upstream primer (10 μM) | 0.5 μL |
| Downstream primer (10 μM) | 0.5 μL |
| Mouse tail genomic DNA | 200 ng |
| KOD-Plus-(1U/μL) | 0.6 μL |
| $ddH_2O$ | Add to 20 μL |

TABLE 13

PCR amplification reaction condition

| Temperature | Time | Cycles |
|---|---|---|
| 95° C. | 5 min | 1 |
| 95° C. | 30 sec | 30 |
| 62° C. | 30 sec | |
| 72° C. | 30 sec | |
| 72° C. | 10 min | 1 |
| 4° C. | 10 min | 1 |

Protein expression in the double humanized CD47/SIRPα mice was further examined. A double humanized CD47/SIRPα homozygote (C57BL/6 background, 5-6 weeks old) was selected for the study. Two wildtype C57BL/6 mice were selected as controls.

7.5 μg of mouse anti-CD3 antibody was intraperitoneally administered to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS and RT-PCR.

Figure 18B:
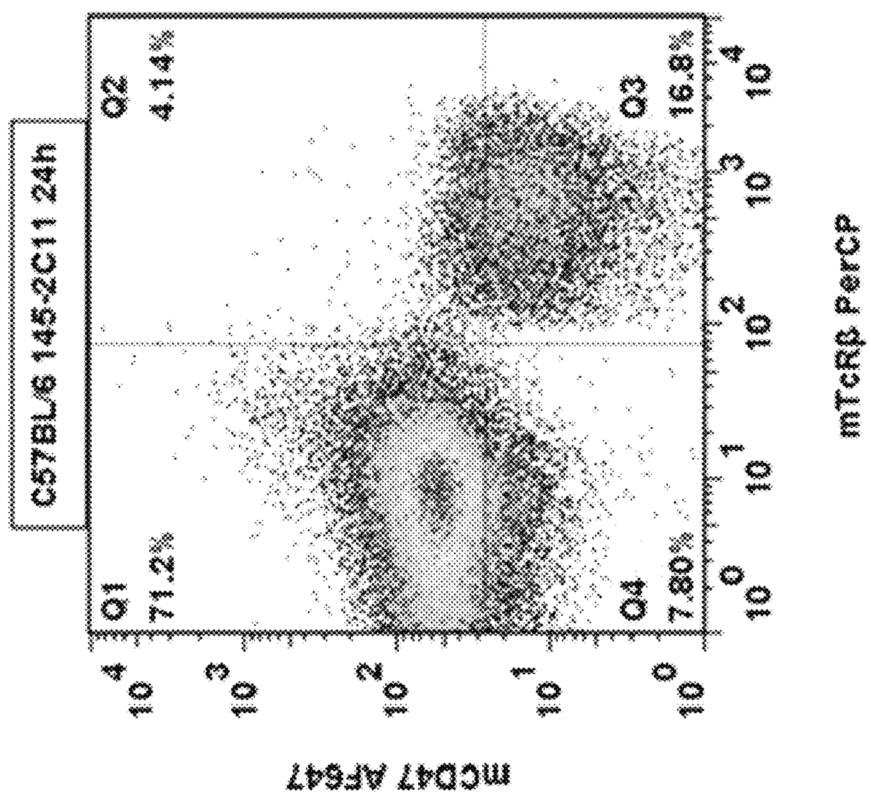
FIGS. 18A-18F are flow cytometry results of wildtype C57BL/6 mice (FIGS. 18A, 18B, 18D, and 18E) and double humanized homozygous $CD47^{H/H}$/$SIRP\alpha^{H/H}$ mice (FIGS. 18C, 18F). CD3 antibody was used to activate spleen cells in FIGS. 18B, 18C, 18E and 18F. Flow cytometry was performed with 1) antibody against mouse CD47 (mCD47 Alexa Fluor 647, AF647) and antibody against mouse TcRβ (mTcRβ PerCP) (FIGS. 18A-18C); and 2) antibody against human CD47 (hCD47 PE), and antibody against mouse TcRβ (mTcRβ PerCP) (FIGS. 18D-18F). In the control groups, no spleen cells stained with hCD47 PE were observed in wildtype mice (FIGS. 18D and 18E); in double humanized CD47/SIRPα groups, spleen cells stained with hCD47 PE were observed (FIG. 18F).
Figure 18A:
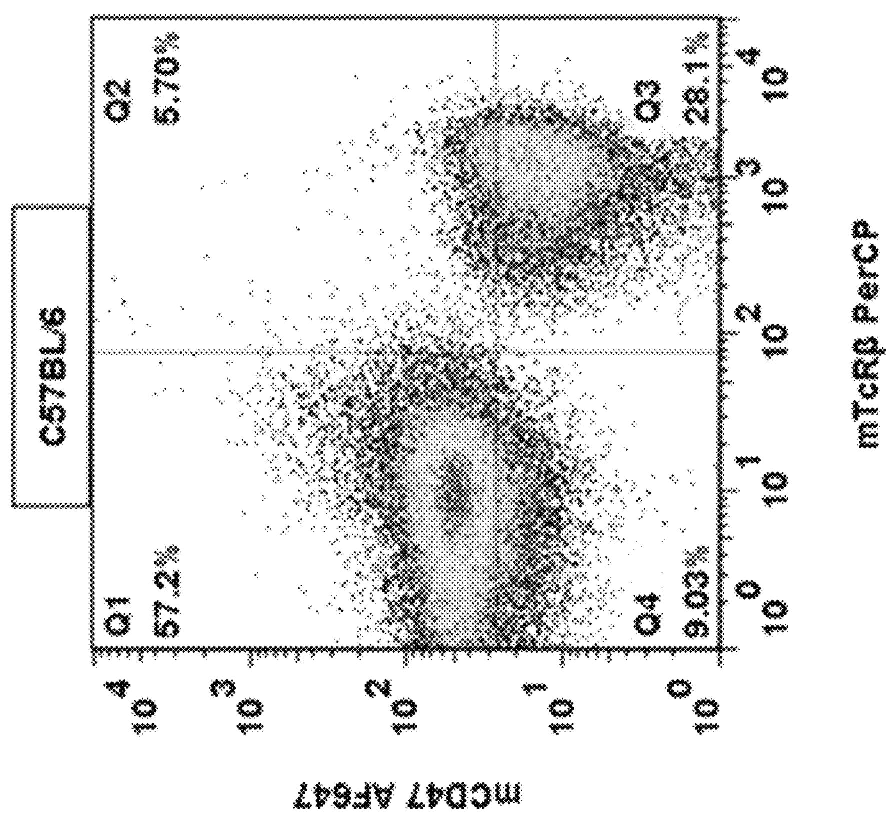
Figures 18C, 18D:
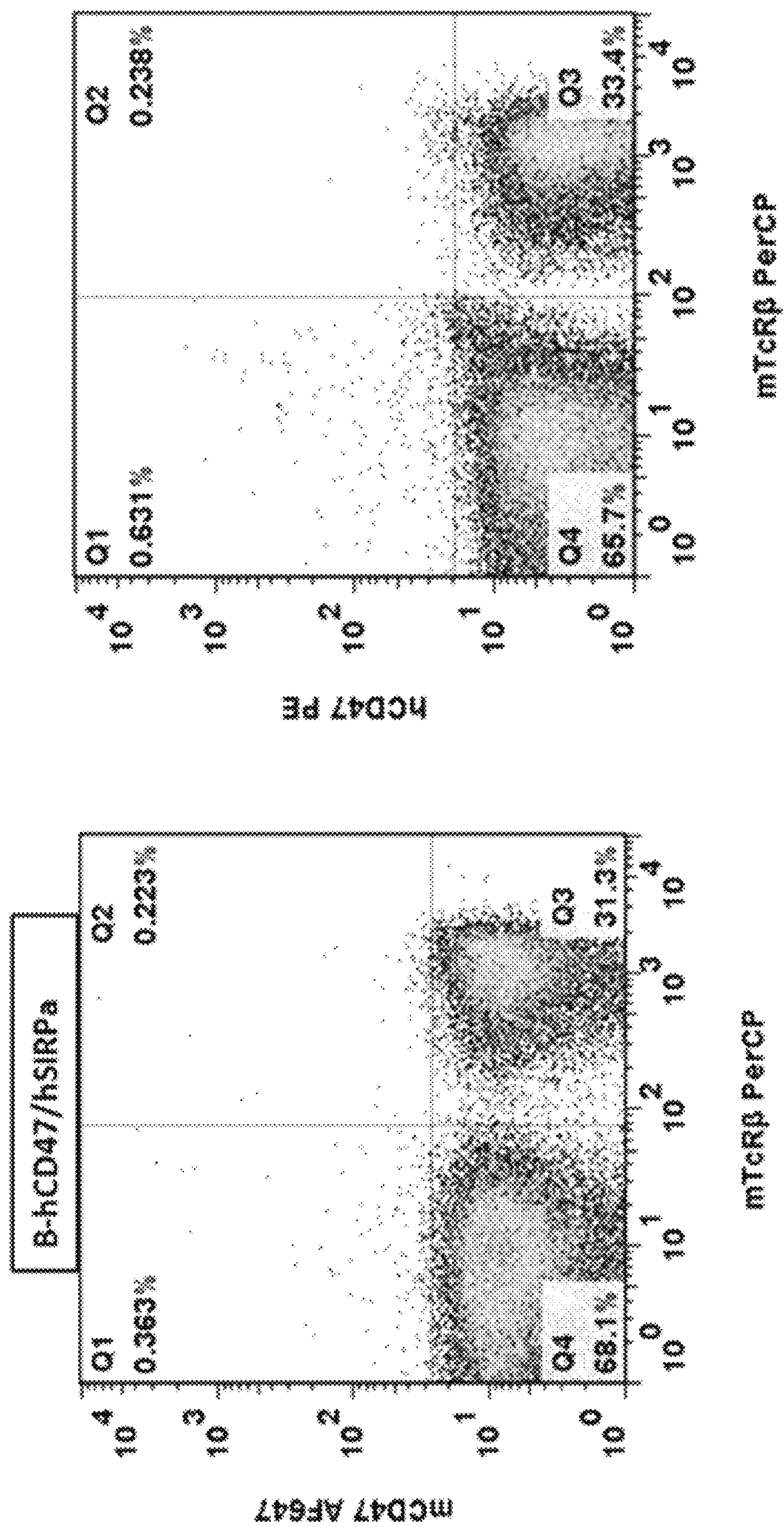
Figure 18F:
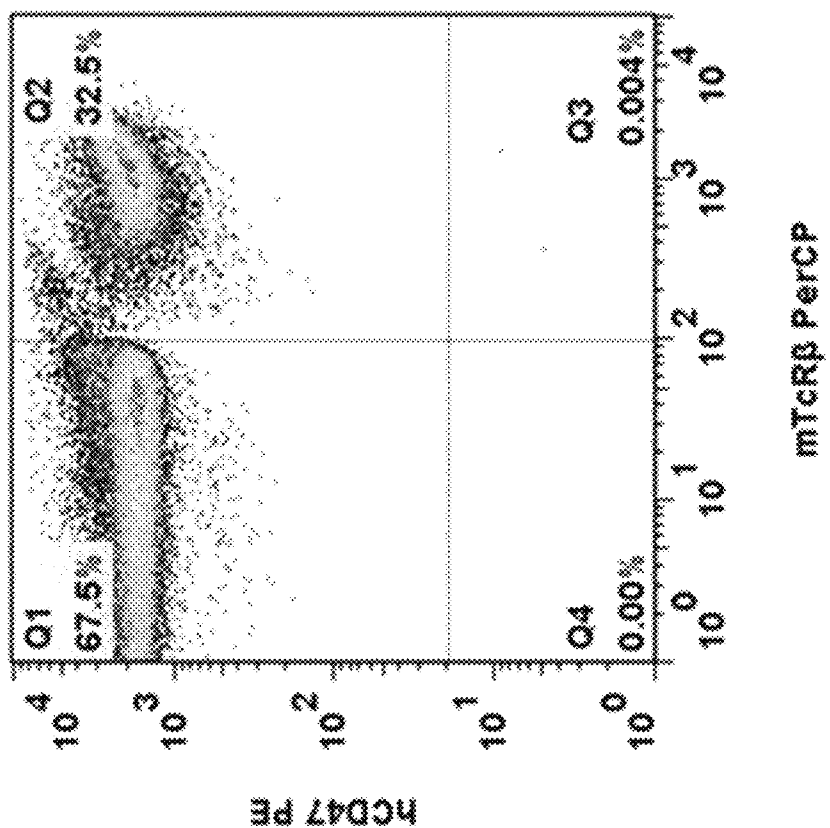
Figure 18E:
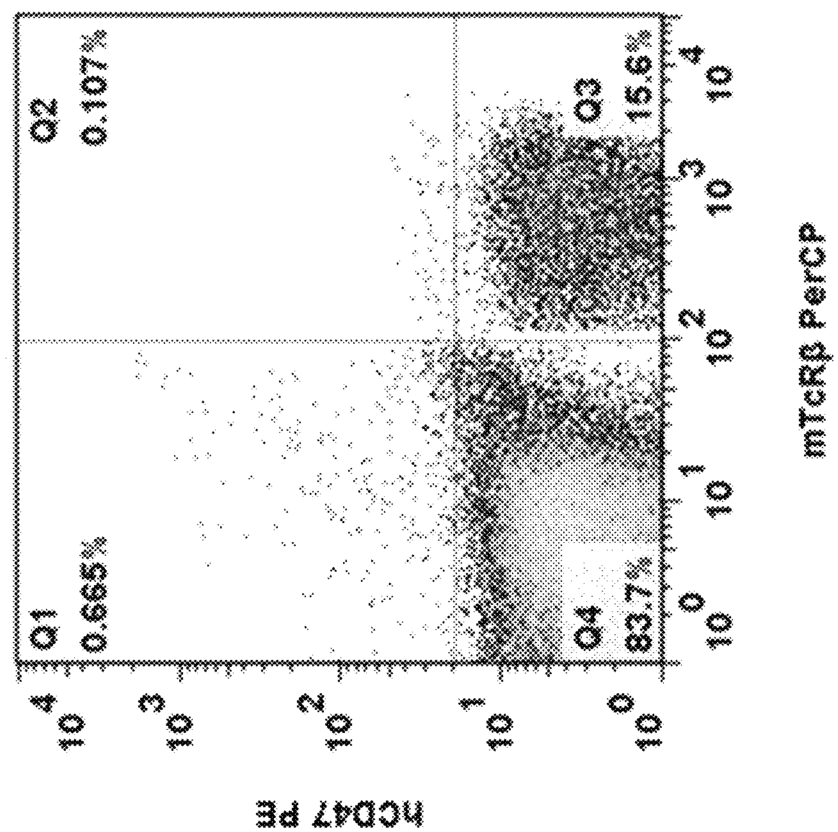
Figure 19B:
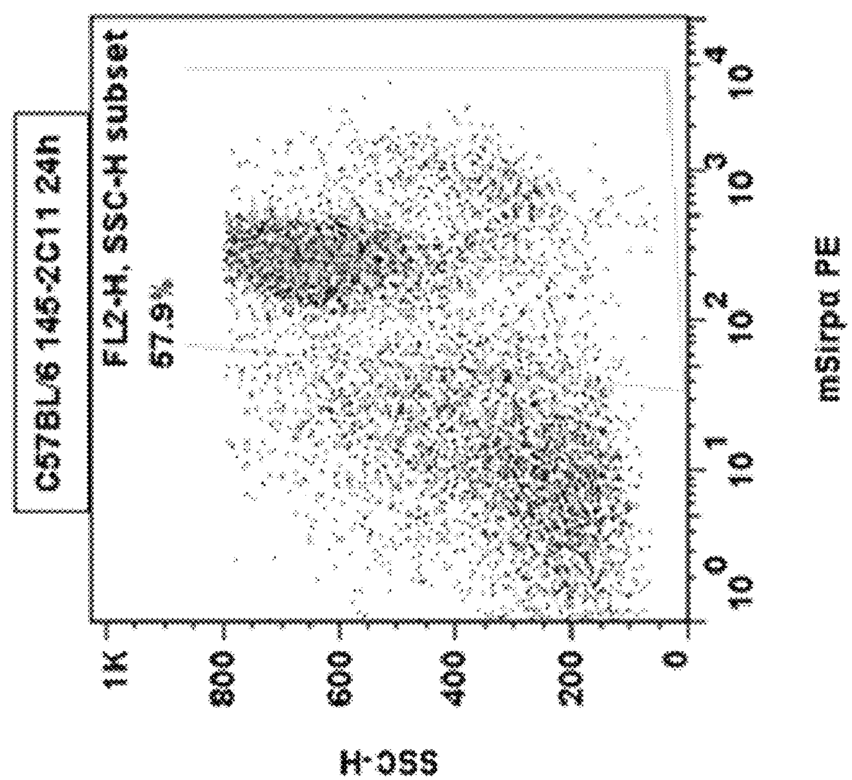
FIGS. 19A-19F are flow cytometry results of wildtype C57BL/6 mice (FIGS. 19A, 19B, 19D, and 19E) and double humanized homozygous $CD47^{H/H}$/$SIRP\alpha^{H/H}$ mice (FIGS. 19C, 19F). CD3 antibody was used to activate spleen cells in FIGS. 19B, 19C, 19E and 19F. Flow cytometry was performed with anti-mSIRPα antibody mSIRPα PE (FIGS. 19A-19C) or anti-hSIRPα antibody hSIRPα APC (FIGS. 19D-19F). Spleens cells labeled with hSIRPα APC were detected in double humanized mice, and were not detected in wildtype C57BL/6 mice.
Figure 19A:
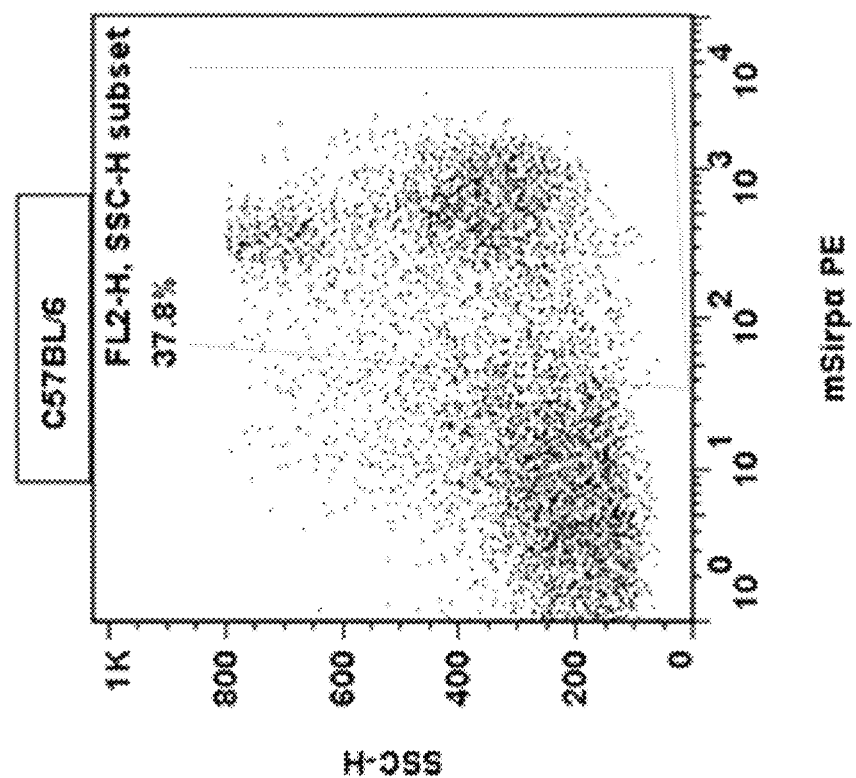
Figure 19D:
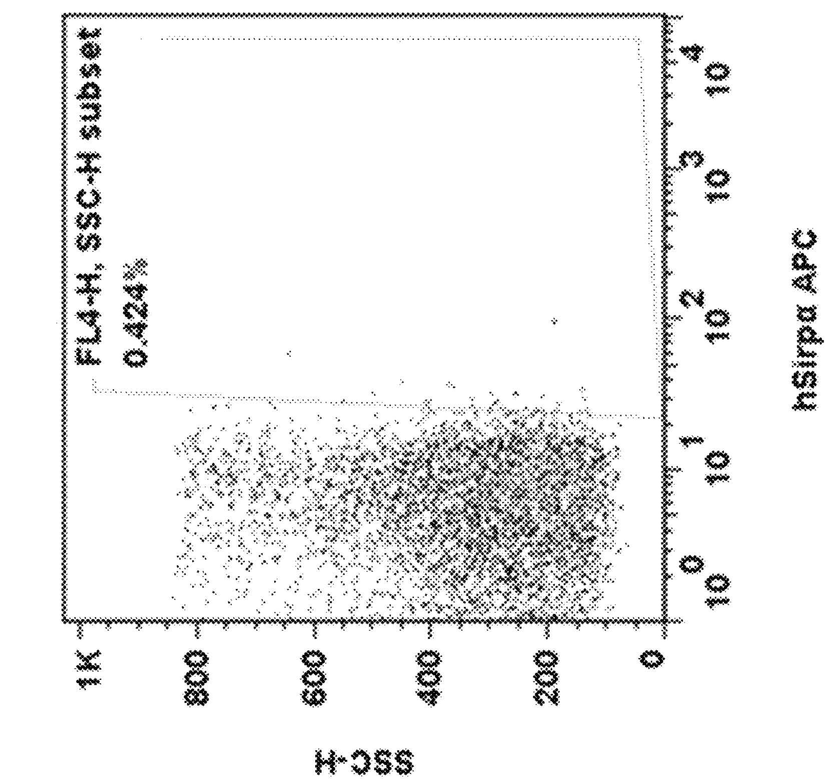
Figure 19C:
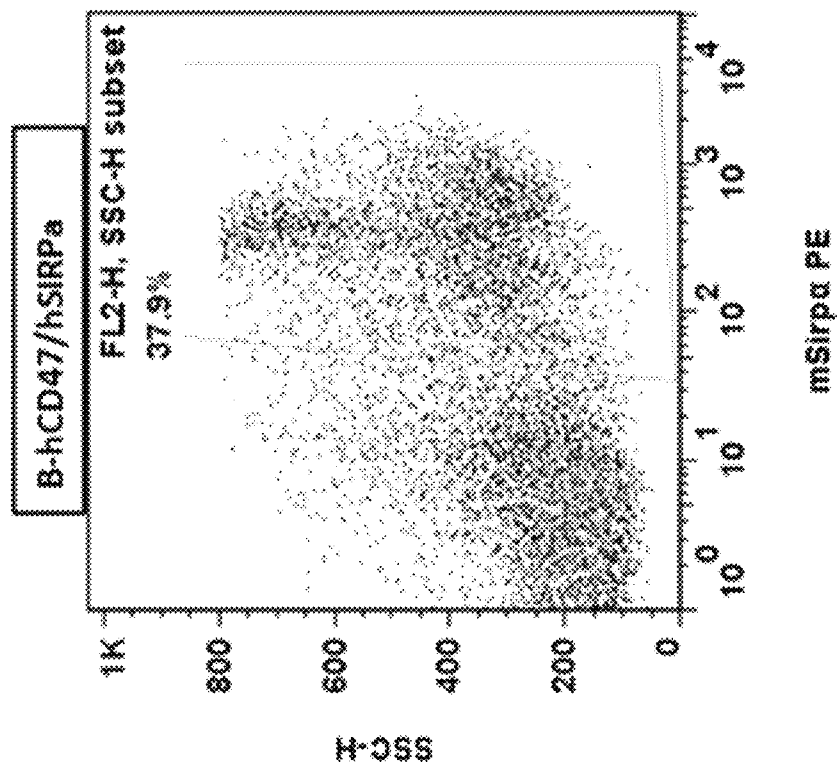
Figure 19F:
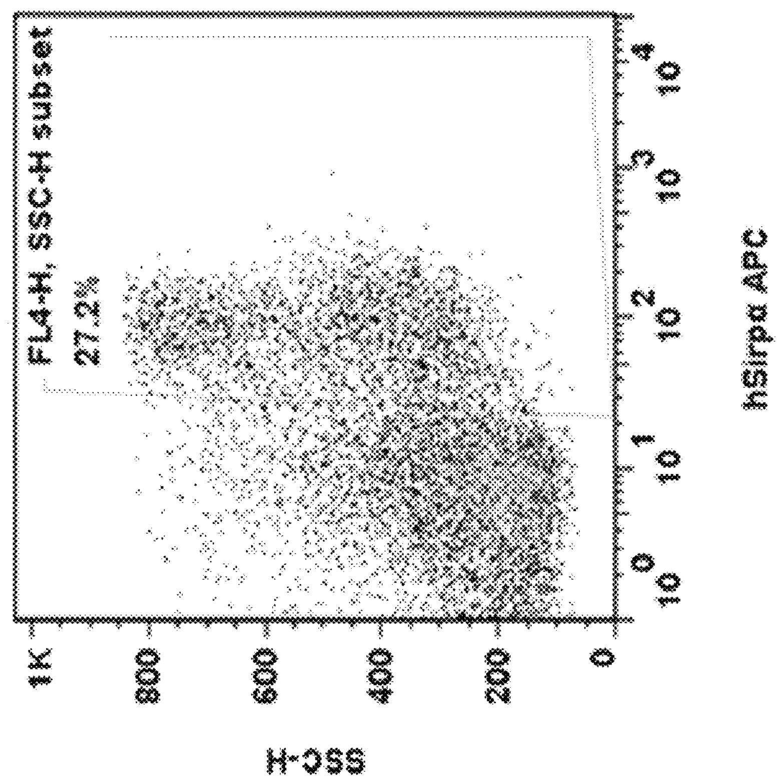
Figure 19E:
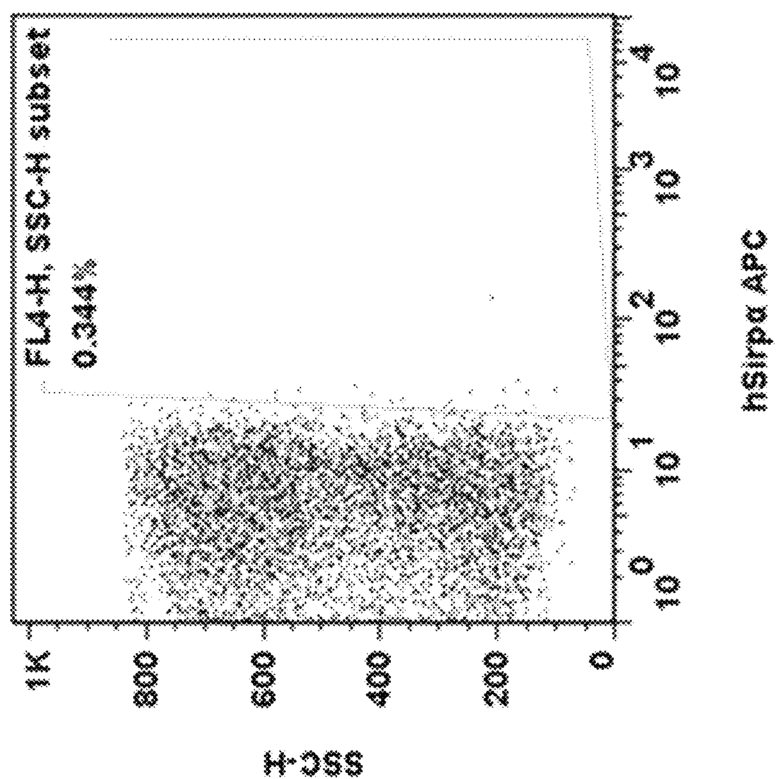

FACS: Flow cytometry was performed with 1) antibody against mouse CD47 (mCD47 Alexa Fluor 647) and antibody against mouse TcRβ (mTcRβ PerCP) (FIGS. 18A-18C); and 2) antibody against human CD47 (hCD47 PE), and antibody against mouse TcRβ (mTcRβ PerCP) (FIGS. 18D-18F); 3) antibody against mouse SIRPα (mSIRPα PE) (FIGS. 19A-19C); and 4) antibody against human SIRPα (hSIRPα APC) (FIGS. 19D-19F).

As shown in FIGS. 18A-18F and FIGS. 19A-19F, no spleen cells stained with hCD47 PE or hSIRPα APC were observed in wildtype C57BL/6 mice with or without CD3 antibody activation. Spleen cells stained with hCD47 PE or hSIRPα APC were observed in transgenic mice homozygous for both humanized CD47 and humanized SIRPα (homozygous $CD47^{H/H}/SIRPα^{H/H}$).

RT-PCR: RT-PCR experiments were performed to confirm the genetic makeup of $CD47^{H/H}/SIRPα^{H/H}$ mice. Total RNA were extracted from spleens and reverse-transcribed into cDNA.

The primer pair mCD47 RT-PCR F2 (SEQ ID NO:39) and mCD47 RT-PCR R2 (SEQ ID NO:40) was used to amplify a 230 bp sequence of mouse CD47. The primer pair hCD47 RT-PCR F1 (SEQ ID NO:41) and hCD47 RT-PCR R1 (SEQ ID NO:42) was used to amplify an approximately 226 bp sequence of human CD47.

```
The primer pair mSIRPα RT-PCR F2:
                                    (SEQ ID NO: 86)
5' -TTGCTGCTGGGGATTCGAC-3'
and

mSIRPα RT-PCR R2:
                                    (SEQ ID NO: 87)
5' -CTGCTGGGGTGACATTACTGAT-3'
```

was used to amplify an approximately 210 bp sequence of mouse SIRPα.

```
The primer pair hSIRPα RT-PCR F1:
                                    (SEQ ID NO: 88)
5' -CCTGACAAGTCCGTGTTGG-3'
and

hSIRPα RT-PCR R1:
                                    (SEQ ID NO: 89)
5' -CTCCTCTGAACCACTGGATGG -3'
```

was used to amplify an approximately 100 bp sequence of human SIRPα.

A 20 μL PCR system was used under the conditions of: 95° C., 5 mins; 35 cycles of the conditions 95° C., 30 sec, 60° C., 30 sec, 72° C., 30 sec; 72° C., 10 mins; storing at 4° C. GAPDH was used as an internal control.

Figure 20:
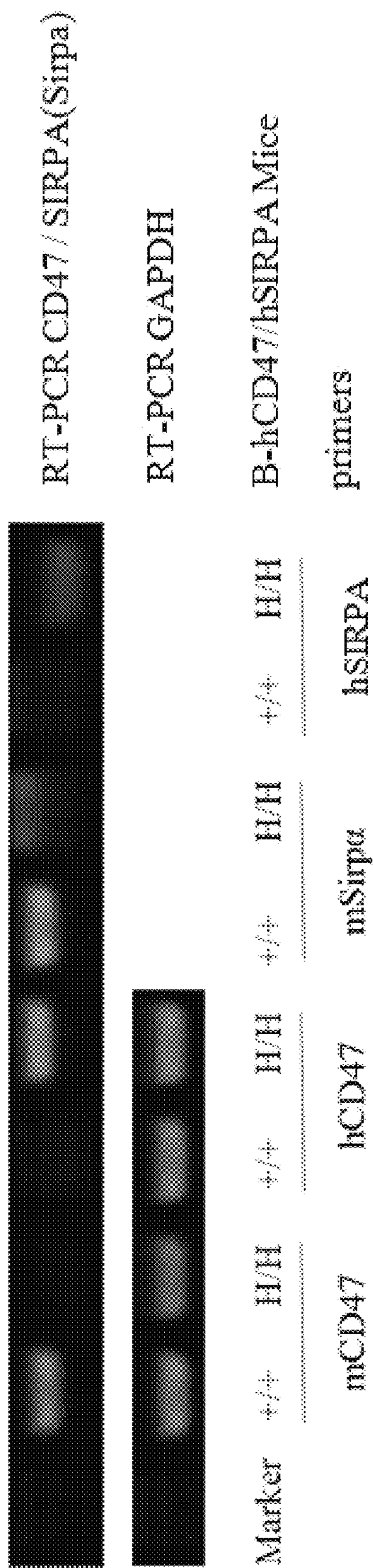
FIG. 20 shows results from RT-PCR experiments amplifying sequences from human CD47 mRNA, mouse CD47 mRNA, human SIRPα mRNA and mouse SIRPα mRNA in homozygous double humanized $CD47^{H/H}$/$SIRP\alpha^{H/H}$ mice. +/+ indicates wildtype mice in C57BL/6 background; H/H in the figure indicates that the mouse is homozygous for both the CD47 and SIRPα genes; and GAPDH was used as a control. Mouse CD47 mRNA and mouse SIRPα mRNA sequences were detected in wildtype C57BL/6 mice activated with anti-CD3 antibody. Human CD47 mRNA and human SIRPα mRNA sequences were detected in double humanized $CD47^{H/H}$/$SIRP\alpha^{H/H}$ mice.

RT-PCR results are shown in FIG. 20. Mouse CD47 mRNA and mouse SIRPα mRNA were detected in wildtype C57BL/6 mice after CD3 antibody activation. mRNA of human CD47 and human SIRPα were detected in $CD47^{H/H}/SIRPα^{H/H}$ mice.

The $CD47^{H/H}/SIRPα^{H/H}$ mice can be used to further prepare a triple transgenic mouse model that are homozygous for humanized CD47, humanized SIRPα, and humanized PD-1. CD47, SIRPα, and PD-1 are all on different chromosomes. Mating (or IVF) $CD47^{H/H}/SIRPα^{H/H}$ mice with humanized PD-1 mouse (e.g. B-hPD-1 mice), following by screening and further mating can be used to produced triple humanized CD47/SIRPα/PD-1 mice.

Example 14: Pharmacological Testing of Antibodies Using Double Humanized CD47/SIRPα Mouse Model Double humanized (CD47/SIRPα) mice CD47 (7-9 weeks) were subcutaneously injected with mouse colon cancer cell MC38. When the tumor volume grew to about 100 $mm^3$, the mice were randomly divided to a control group and treatment groups (n=5/group). Each of the treatment groups was treated with one antibody. The six treatment groups were treated with six antibodies as follows: anti-hCD47 antibody AB1, anti-hCD47 antibody AB2, anti-hCD47 antibody AB3, anti-hSIRPα antibody Ab-S1, anti-hSIRPα antibody Ab-S2, and anti-hSIRPα antibody Ab-S3. The control group was injected with physiological saline. The mice were measured for their tumor size and weighed twice a week, and euthanized when tumor size reached 3000 $mm^3$.

Figure 21:
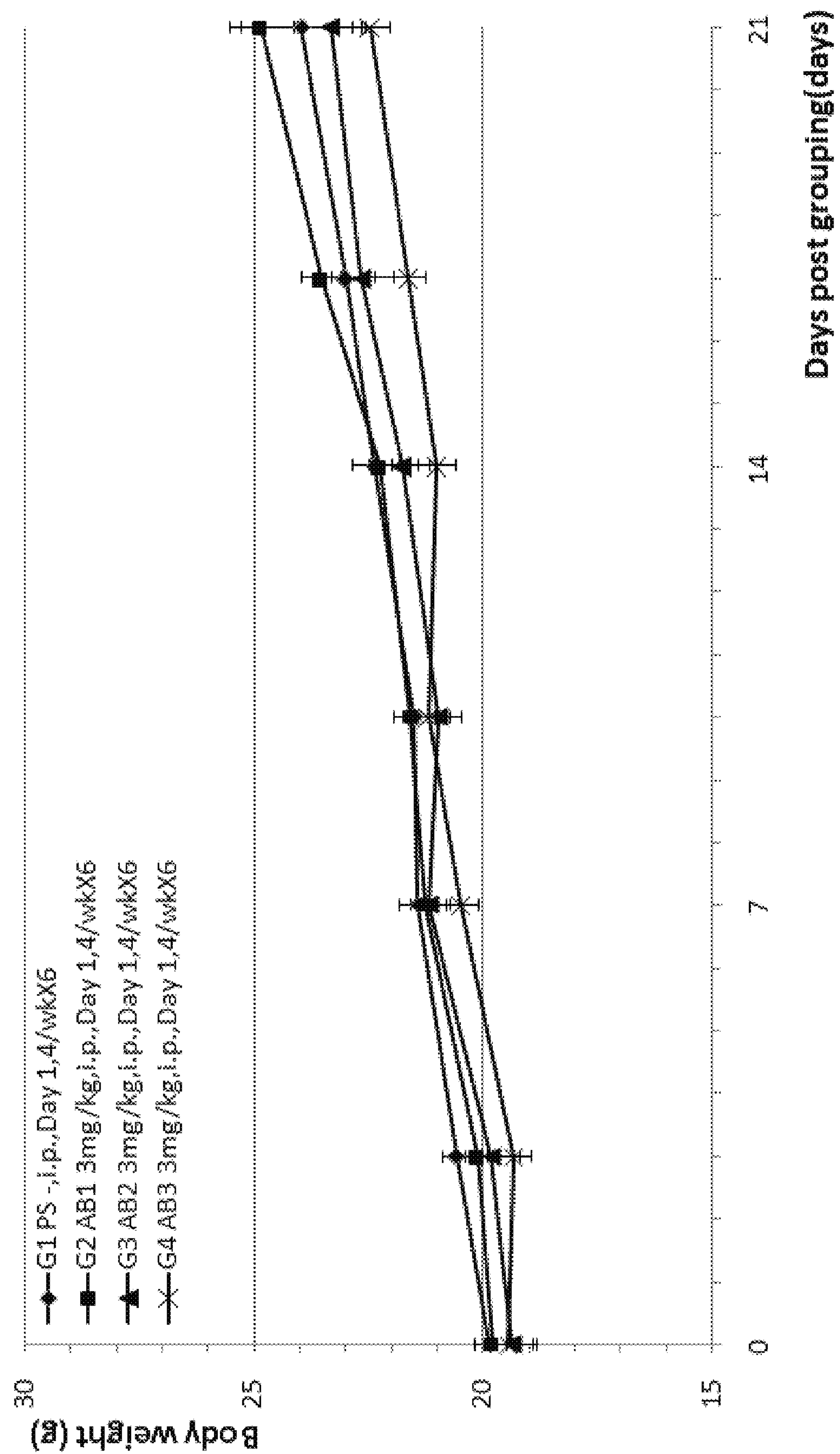
FIG. 21 Mouse colon cancer cells MC38 were injected into double humanized CD47/SIRPα mice. Antitumor efficacy studies were performed with anti-hCD47 antibodies. The average weights of the different groups are shown in the figure.
Figure 22:
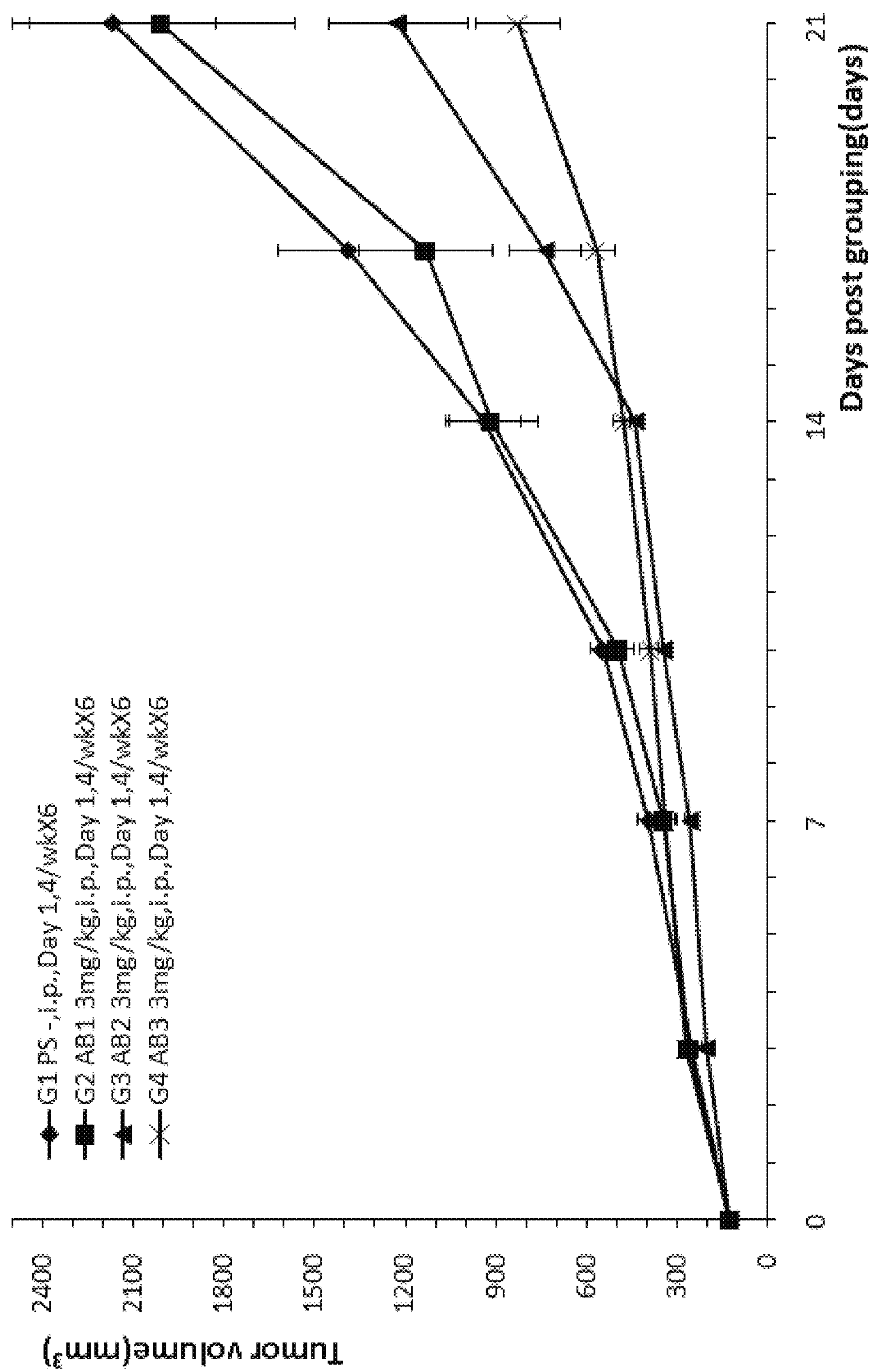
FIG. 22 Mouse colon cancer cells MC38 were injected into double humanized CD47/SIRPα mice. Antitumor efficacy studies were performed with anti-hCD47 antibodies. Tumor size in the different groups are shown in the figure.
Figure 23:
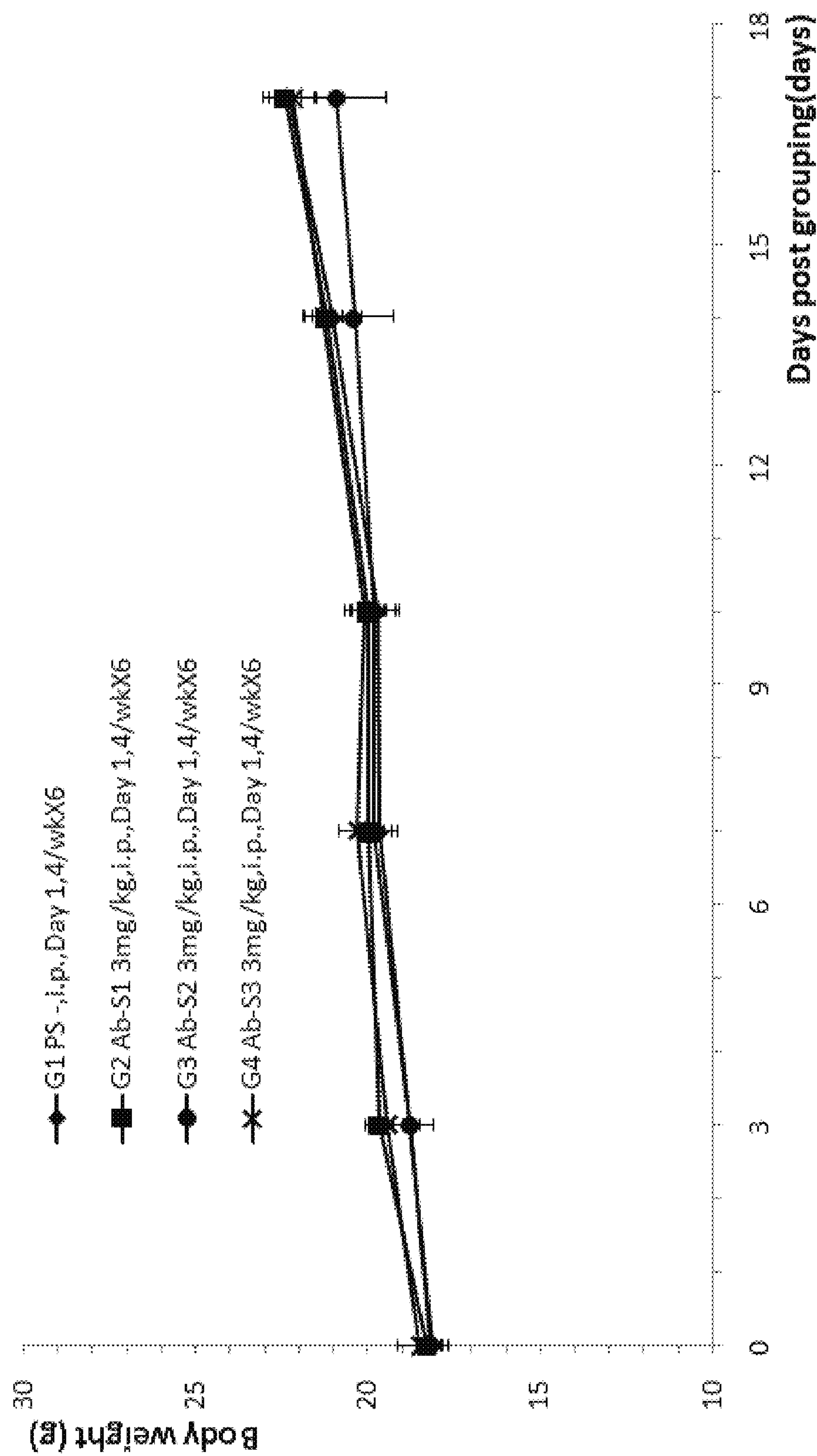
FIG. 23 Mouse colon cancer cells MC38 were injected into double humanized CD47/SIRPα mice. Antitumor efficacy studies were performed with anti-hSIRPα antibodies. The average weights of the different groups are shown in the figure.
Figure 24:
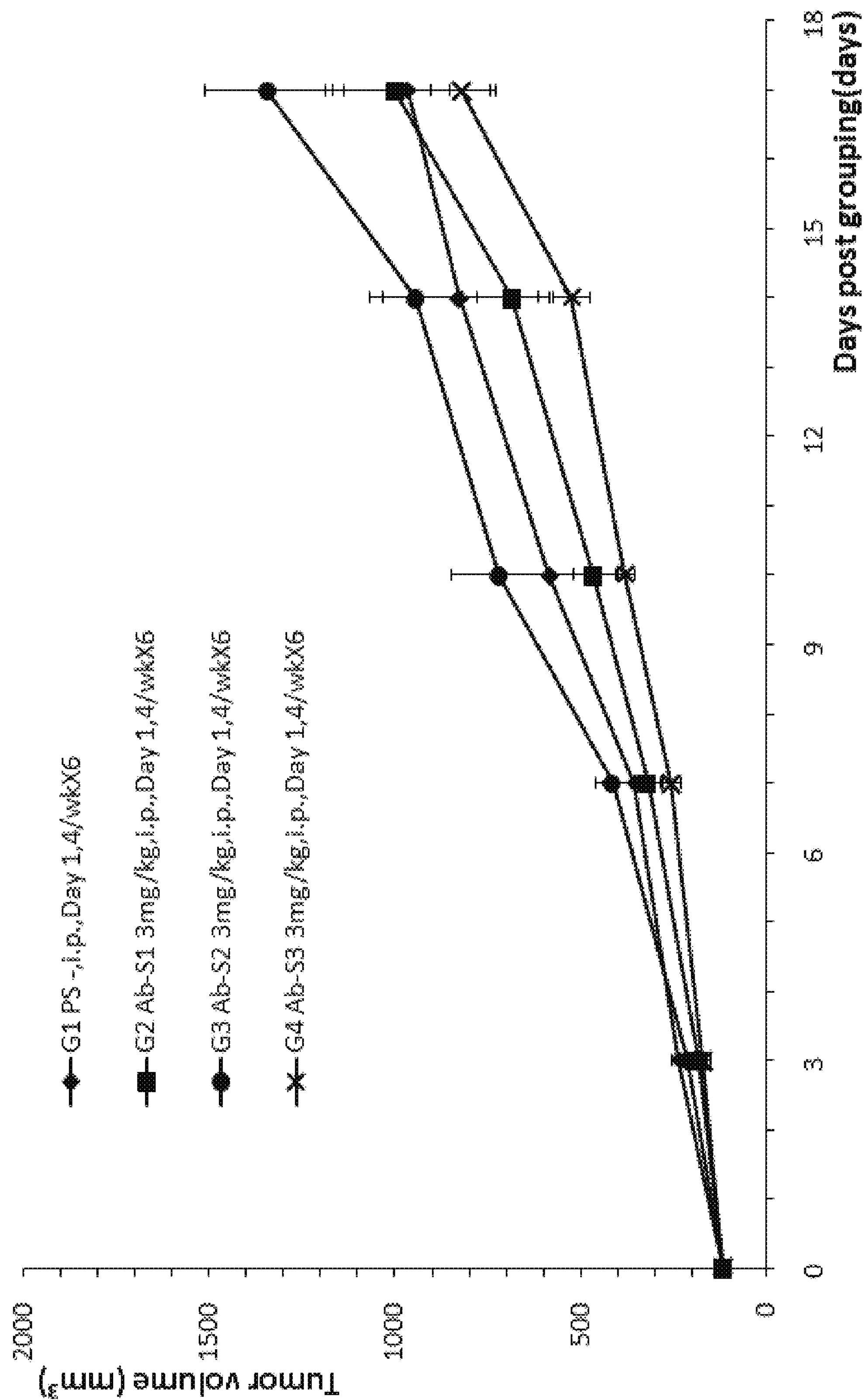
FIG. 24 Mouse colon cancer cells MC38 were injected into double humanized CD47/SIRPα mice. Antitumor efficacy studies were performed with anti-hSIRPα antibodies. Tumor size in the different groups are shown in the figure.

Overall, the animals in each group were healthy, and the body weights of all the treatment groups were not significantly different from the control group (FIG. 21 and FIG. 23), indicating that the three anti-hCD47 antibodies and the three anti-hSIRPα antibodies were well tolerated by the mice and did not cause obvious toxic effects.

Although the body weights did not show significant difference over the course of the entire experimental period (FIG. 21 and FIG. 23), the tumor sizes were different. Tumor size in the control group continued to grow, while the tumor size in the groups injected with anti-hCD47 antibodies decreased as compared to the control group, indicating that the three anti-hCD47 antibodies had different tumor inhibitory effects. Tumor growth in groups treated with anti-hSIRPα antibodies were also inhibited, indicating that the three anti-hSIRPα antibodies had lower tumor inhibitory effects. None of the six antibodies had obvious toxic effects to the animals.

Table 14 shows results for this experiment, including the tumor volumes at the day of grouping (day 0), 14 days after the grouping, and at the end of the experiment, the survival rate of the mice, and the Tumor Growth Inhibition value ($TGI_{TV}$%).

TABLE 14

| | | Tumor volume ($mm^3$) | | | | |
|---|---|---|---|---|---|---|
| Anti-hCD47 antibodies | | Day 0 | Day 14 | Day 21 | Survival | $TGI_{TV}$% |
| Control | G1 | 128 ± 12 | 939 ± 120 | 2166 ± 335 | 5/5 | N/A |
| Treatment | G2 | 128 ± 8 | 917 ± 154 | 2007 ± 438 | 5/5 | 7.8 |
| | G3 | 128 ± 9 | 440 ± 23 | 1227 ± 229 | 5/5 | 46.7 |
| | G4 | 128 ± 10 | 478 ± 37 | 828 ± 139 | 5/5 | 65.6 |

| | | Tumor volume ($mm^3$) | | | | |
|---|---|---|---|---|---|---|
| Anti-hSIRPα antibodies | | Day 0 | Day 14 | Day 17 | Survival | $TGI_{TV}$% |
| Control | G1 | 117 ± 4 | 827 ± 208 | 967 ± 221 | 5/5 | N/A |
| Treatment | G2 | 116 ± 4 | 685 ± 96 | 999 ± 320 | 5/5 | 0 |
| | G3 | 117 ± 10 | 944 ± 125 | 1342 ± 170 | 5/5 | 0 |
| | G4 | 116 ± 5 | 527 ± 49 | 820 ± 88 | 5/5 | 17.2 |

All mice survived to the end of the experiment. In groups treated with anti-hCD47 antibodies, the average tumor volume is 2166±335 $mm^3$ in the control group (G1), 2007±438 $mm^3$ in the AB1 treatment group (G2), 1227±229 $mm^3$ in the AB2 treatment group (G3), and 828±139 $mm^3$ in the AB3 treatment group (G4). The average tumor size in G2 group did not show significant difference from that in the G1 group, while the average tumor sizes in G3 and G4 groups each showed significant ($p<0.05$) difference from that in G1 group, with the $TGI_{TV}$ % being 46.7% and 65.6% respectively. The results indicate that the three anti-hCD47 antibodies showed different tumor inhibitory effects, while all were safe to use without obvious toxicity.

In groups treated with anti-hSIRPα antibodies, tumor inhibitory effects were not significant for the Ab-S1 (G2) and the Ab-S2 (G3) treatment groups compared to the control (G1) group. The Ab-S3 treatment group (G4) had an average tumor size of 820±88 $mm^3$, smaller than the control (G1) group. The results indicate that the three anti-hSIRPα antibodies had different tumor inhibitory effects, with the Ab-S3 antibody having better tumor inhibitory effects than Ab-S1 and Ab-S2.

This example demonstrates that the double humanized (CD47/SIRPα) mouse model is useful for screening and testing for therapeutic agents (e.g. antibodies) targeting human CD47 or human SIRPα. The mouse model is useful for testing efficacies of the therapeutic agents.

Example 15: Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Figure 26:
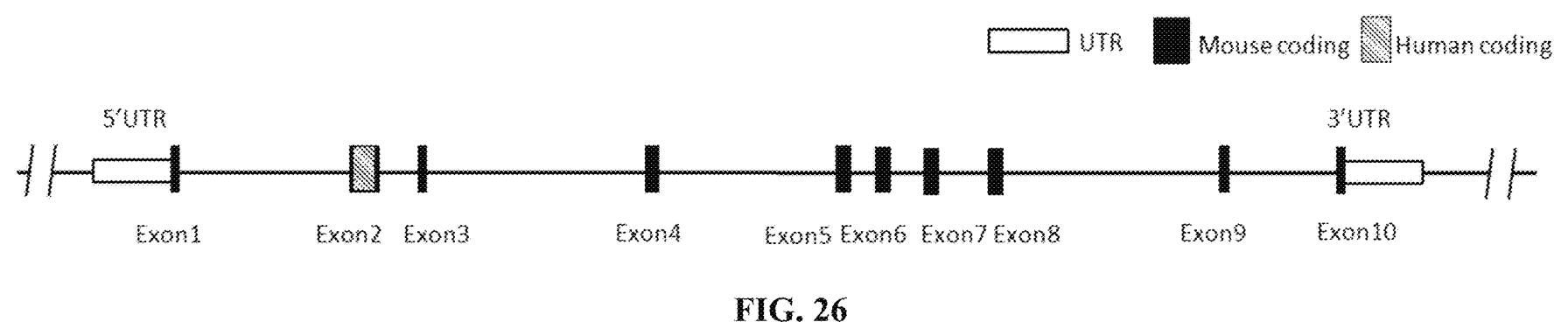

Based on the CD47 transcript NM_010581.3 and the corresponding protein sequence NP_034711.1, FIG. 25 and FIG. 26 show the targeting strategy for generating the humanized CD47 mouse model. FIG. 25 further shows the design of the recombinant vector. Since the objective is to replace exon 2 of the mouse CD47 gene in whole or in part with the corresponding sequence in human CD47 gene, a recombinant vector that contains a 5' homologous arm (4081 bp), a 3' homologous arm (3410 bp) and a sequence fragment from human CD47 (312 bp) is designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm.

Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the CD47 gene humanized homozygous mice can be obtained by mating these mice with each other. The methods of genotyping and using the F1 heterozygous mice or F2 homozygous mice are similar to the methods as described in the examples above.

Example 16: Quantification of Binding Between SIRPα and Mouse or Human CD47

Experiments were performed to test the binding affinity between CD47 and SIRPα in mice with different backgrounds. Wildtype mice in C57BL6 background, wildtype mice in BALB/c background, and humanized SIRPα mice (B-hSIRPα) in C57BL/6 background were tested. Peritoneal cavity cells of mice were collected and plated on 96-well plates. Mouse CD47 proteins or human CD47 proteins were added to the wells and incubated with these cells. The cells in the wells were further incubated with a primary human antibody against mouse CD47 or human CD47, and a secondary antibody anti-human IgG (AF647-Anti-hIgG), which recognizes the primary antibodies. Fluorescent labeled antibodies against mouse CD11b (Anti-mCD11b PE) or against mouse F4/80 (Anti-mF4/80 FITC) were used to label different populations of mouse immune cells.

Figures 29A, 29B:
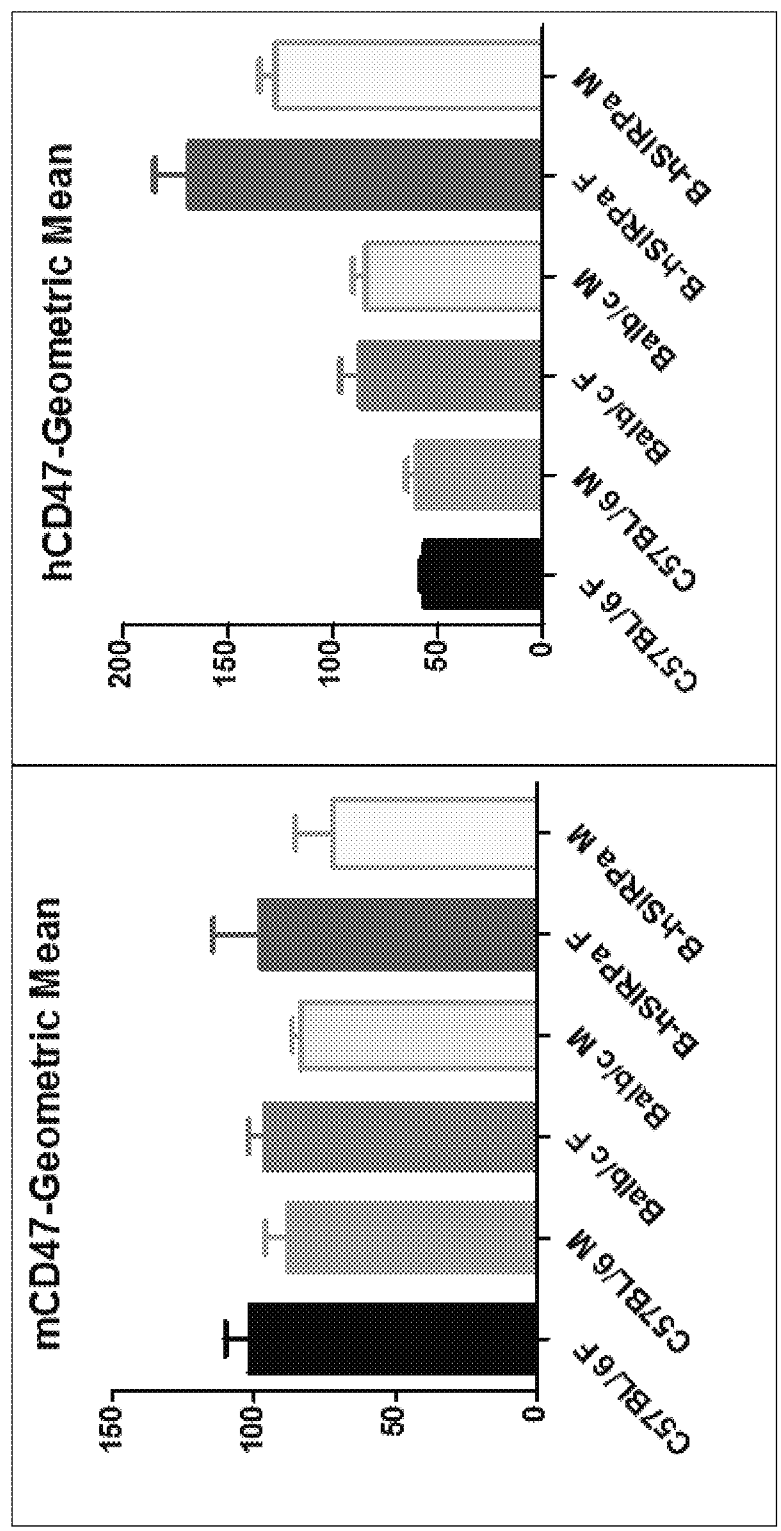
FIG. 29A shows the quantification results from flow cytometry analysis indicating the binding affinity between SIRPα and mouse CD47. The Y axis is the geometric mean of flow cytometry signal. "M" in X axis indicates male, and "F" in X axis indicates female.
FIG. 29B shows the quantification results from flow cytometry analysis indicating the binding affinity between SIRPα and human CD47. The Y axis is the geometric mean of flow cytometry signal. "M" in X axis indicates male, and "F" in X axis indicates female.

The cells were then subject to flow cytometry analysis. The results were quantified and plotted in FIGS. 29A-29B. The results show that the binding between mouse CD47 proteins and the endogenous SIRPα proteins in wildtype mice in both C57BL6 and BALB/c background had a geometric mean around 100 (FIG. 29A). Similar values were observed in humanized SIRPα mice (B-hSIRPα), indicating that the humanized SIRPα proteins in the B-hSIRPα mouse line can bind to mouse CD47 (FIG. 29A) (no significant difference were found between the B-hSIRPα mice and the wildtype mice).

The results also show that the binding between human CD47 and endogenous mouse SIRPα proteins in wildtype C57BL6 mice is weaker than in wildtype BALB/c mice (FIG. 29B). The difference is significant ($P<0.05$). The binding of human CD47 proteins to endogenous mouse SIRPα proteins in wildtype BALB/c mice was comparable to the binding of mouse CD47 proteins to endogenous mouse SIRPα proteins (no significant difference) (FIGS. 29A and 29B). In addition, human CD47 and humanized SIRPα proteins in the humanized B-hSIRPα mice had a much stronger binding affinity as compared to the binding between human CD47 and endogenous mouse SIRPα proteins (FIG. 29B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically modified mouse whose genome comprises a nucleic acid sequence encoding a chimeric CD47 comprising a humanized extracellular region and five endogenous transmembrane domains, wherein the nucleic acid sequence is operably linked to an endogenous CD47 promoter and the mouse functionally expresses the chimeric CD47.

2. The genetically modified mouse of claim 1, wherein the mouse does not express endogenous CD47.

3. The genetically modified mouse of claim 1, wherein the mouse is homozygous with respect to the nucleic acid sequence encoding the chimeric CD47.

4. The genetically modified mouse of claim 1, wherein the genome of the mouse further comprises a nucleic acid sequence encoding a humanized SIRPα.

5. A method of evaluating a drug for treating a tumor, the method comprising:

a) administering the drug to the genetically modified mouse of claim 1, wherein the mouse has a tumor comprising human cancer cells; and b) determining whether the drug inhibits the tumor.

6. The method of claim 5, wherein the drug is an anti-CD47 antibody.

7. A genetically modified mouse whose genome comprises a chimeric CD47 gene comprising a replacement of a nucleic acid sequence encoding an extracellular domain within exon 2 of an endogenous CD47 gene with a nucleic acid sequence encoding an extracellular domain within exon 2 of a human CD47 gene, and endogenous exons 3-7, wherein the mouse functionally expresses a chimeric CD47.

8. The genetically modified mouse of claim 7, wherein the mouse does not express endogenous CD47.

9. The genetically modified mouse of claim 7, wherein the mouse is homozygous with respect to the nucleic acid sequence encoding the chimeric CD47.

10. The genetically modified mouse of claim 7, wherein the genome of the mouse further comprises a nucleic acid sequence encoding a humanized SIRPα.

11. The genetically modified mouse of claim 7, wherein the nucleic acid sequence encoding an extracellular domain within exon 2 of a human CD47 gene is at least 300 nucleotides.

12. A method of preparing a genetically modified mouse, the method comprising:

1) providing a plasmid comprising a human CD47 gene fragment from exon 2 of the human CD47 gene, a 5' homology arm, and a 3' homology arm, wherein the 5' and 3' homology arms target exon 2 of a mouse CD47 gene;

2) providing a first single guide RNA (sgRNA) that targets a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;

3) providing a second sgRNA that targets a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16;

4) modifying the genome of a mouse embryo using the plasmid of step 1), the first sgRNA of step 2), the second sgRNA of step 3), and Cas9; and 5) transplanting the embryo obtained in step 4) into a recipient mouse such that a transgenic mouse is obtained whose genome comprises a nucleic acid sequence encoding a chimeric CD47 comprising a humanized extracellular region and five endogenous transmembrane domains, wherein the nucleic acid sequence is operably linked to an endogenous CD47 promoter and the mouse functionally expresses the chimeric CD47.

13. The genetically modified mouse of claim 12, wherein the first sgRNA targets the nucleic acid sequence of SEQ ID NO: 6 and the second sgRNA targets the nucleic acid sequence of SEQ ID NO: 9.

* * * * *

SEQUENCE LISTING

```
<160> NUMBER OF SEQ ID NOS: 89

<210> SEQ ID NO 1
<211> LENGTH: 23
<212> TYPE: DNA
<213> ORGANISM: Artificial
<220> FEATURE:
<223> OTHER INFORMATION: sgRNA target sequence

<400> SEQUENCE: 1

cccttgcatc gtccgtaatg tgg                                              23


<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2

tccacattac ggacgatgca agg                                              23


<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3

tgctttgcgc ctccacatta cgg                                              23


<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4

cacttcatgc aatgaaactg tgg                                              23


<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5

ccgaagaaat gtttgtgaag tgg                                              23


<210> SEQ ID NO 6
<211> LENGTH: 23
<212> TYPE: DNA
<213> ORGANISM: Artificial
```

<220> FEATURE:
<223> OTHER INFORMATION: sgRNA target sequence

<400> SEQUENCE: 6
attgcatgaa gtgaactcta tgg 23

<210> SEQ ID NO 7
<211> LENGTH: 23
<212> TYPE: DNA
<213> ORGANISM: Artificial
<220> FEATURE:
<223> OTHER INFORMATION: sgRNA target sequence

<400> SEQUENCE: 7
tcgtatattt tcatctatga tgg 23

<210> SEQ ID NO 8
<211> LENGTH: 23
<212> TYPE: DNA
<213> ORGANISM: Artificial
<220> FEATURE:
<223> OTHER INFORMATION: sgRNA target sequence

<400> SEQUENCE: 8
ccacttcaca aacatttctt cgg 23

<210> SEQ ID NO 9
<211> LENGTH: 23
<212> TYPE: DNA
<213> ORGANISM: Artificial
<220> FEATURE:
<223> OTHER INFORMATION: sgRNA target sequence

<400> SEQUENCE: 9
aatggataag cgcgatgcca tgg 23

<210> SEQ ID NO 10
<211> LENGTH: 23
<212> TYPE: DNA
<213> ORGANISM: Artificial
<220> FEATURE:
<223> OTHER INFORMATION: sgRNA target sequence

<400> SEQUENCE: 10
gataagcgcg atgccatggt ggg 23

<210> SEQ ID NO 11
<211> LENGTH: 23
<212> TYPE: DNA
<213> ORGANISM: Artificial
<220> FEATURE:
<223> OTHER INFORMATION: sgRNA target sequence

<400> SEQUENCE: 11
gcaagtgtag tttcccacca tgg 23

<210> SEQ ID NO 12
<211> LENGTH: 23
<212> TYPE: DNA
<213> ORGANISM: Artificial
<220> FEATURE:
<223> OTHER INFORMATION: sgRNA target sequence

<400> SEQUENCE: 12
tcagtctcag acttaatcaa tgg 23

<210> SEQ ID NO 13
<211> LENGTH: 23
<212> TYPE: DNA
<213> ORGANISM: Artificial
<220> FEATURE:
<223> OTHER INFORMATION: sgRNA target sequence

<400> SEQUENCE: 13
tgagactgag atttttgcac tgg 23

<210> SEQ ID NO 14
<211> LENGTH: 23
<212> TYPE: DNA
<213> ORGANISM: Artificial
<220> FEATURE:
<223> OTHER INFORMATION: sgRNA target sequence

<400> SEQUENCE: 14
gcgcttatcc attttcaaag agg 23

<210> SEQ ID NO 15
<211> LENGTH: 23
<212> TYPE: DNA
<213> ORGANISM: Artificial
<220> FEATURE:
<223> OTHER INFORMATION: sgRNA target sequence

<400> SEQUENCE: 15
tggcattgcc tctttgaaaa tgg 23

<210> SEQ ID NO 16
<211> LENGTH: 23
<212> TYPE: DNA
<213> ORGANISM: Artificial
<220> FEATURE:
<223> OTHER INFORMATION: sgRNA target sequence

<400> SEQUENCE: 16
gtgacagagt tatccagaga agg 23

<210> SEQ ID NO 17
<211> LENGTH: 23
<212> TYPE: DNA
<213> ORGANISM: Artificial
<220> FEATURE:
<223> OTHER INFORMATION: sgRNA target sequence

<400> SEQUENCE: 17
tataactgtt ttgccttctc tgg 23

<210> SEQ ID NO 18
<211> LENGTH: 20
<212> TYPE: DNA
<213> ORGANISM: Artificial
<220> FEATURE:
<223> OTHER INFORMATION: sgRNA sequence

<400> SEQUENCE: 18
taggcatgaa gtgaactcta 20

<210> SEQ ID NO 19
<211> LENGTH: 20
<212> TYPE: DNA
<213> ORGANISM: Artificial
<220> FEATURE:
<223> OTHER INFORMATION: sgRNA sequence

<400> SEQUENCE: 19
aaactagagt tcacttcatg 20

<210> SEQ ID NO 20
<211> LENGTH: 19
<212> TYPE: DNA
<213> ORGANISM: Artificial
<220> FEATURE:
<223> OTHER INFORMATION: sgRNA sequence

<400> SEQUENCE: 20
taggataagc gcgatgcca 19

<210> SEQ ID NO 21
<211> LENGTH: 19
<212> TYPE: DNA
<213> ORGANISM: Artificial
<220> FEATURE:
<223> OTHER INFORMATION: sgRNA sequence

<400> SEQUENCE: 21
aaactggcat cgcgcttat 19

<210> SEQ ID NO 22
<211> LENGTH: 132
<212> TYPE: DNA
<213> ORGANISM: Artificial
<220> FEATURE:
<223> OTHER INFORMATION: Synthesized sequence

<400> SEQUENCE: 22
gaattctaat acgactcact atagggggtc ttcgagaaga cctgttttag agctagaaat 60
agcaagttaa aataaggcta gtccgttatc aacttgaaaa agtggcaccg agtcggtgct 120
tttaaaggat cc 132

<210> SEQ ID NO 23
<211> LENGTH: 486
<212> TYPE: DNA
<213> ORGANISM: Artificial
<220> FEATURE:
<223> OTHER INFORMATION: Homo sapiens and Mus musculus

<400> SEQUENCE: 23
tatatgcaga ttgtaatgaa atatttttgt gtatgtattc caggttcagc tcaactactg 60
tttaataaaa caaaatctgt agaattcacg ttttgtaatg acactgtcgt cattccatgc 120
tttgttacta atatggaggc acaaaacact actgaagtat acgtaaagtg gaaatttaaa 180
ggaagagata tctacacctt tgatggagct ctaaacaagt ccactgtccc cactgacttt 240
agtagtgcaa aaattgaagt ctcacaatta ctaaaaggag atgcctcttt gaagatggat 300
aagagtgatg ctgtctcaca cacaggaaac tacacttgtg aagtaacaga attaaccaga 360
gaaggtgaaa cgatcataga gctgaaaaac cgcacgggta agtgacacag tttgcctgtt 420
ttgaaacgtg tgttgagata tggttgccac tgtgggagtg ctgtaaggtg gaaccttgca 480
gaagtc 486

<210> SEQ ID NO 24
<211> LENGTH: 1058
<212> TYPE: DNA
<213> ORGANISM: Mus musculus

<400> SEQUENCE: 24
tgtctggttt acatagaagg aggaactatt aatgattaat ggagttaatg ttttatattc 60
gttggtactt tgggttttga aggcaaagtc aacaagctac tcagataaga gctttggata 120
catggccatg ttagaaaata gagtggtagt tcctccacat ctttgccatt tgagtcaaat 180
ggtaagcagg gcactcaagg gtggtctatg ccagtgagaa gagccaatga gtattctcta 240
ctcatcagca gcatctgctc ttgctttcaa atttttcctt ggcttttagg gtagtttatg 300
gtttattgga ggaagaaata cctgtaatct acatttcaca attgttctgt agagtcagtg 360
aaatgtcggg gtaggaaaaa tgccattcaa ttgtgtggaa tcctttgtgt ggacttgcat 420
acaaagcgcc tatcgctctc tcttttgaag tgggaaatag ccacagagaa catttttttcc 480
ctcattagta ttccaagact tcccatcctc ttggaaagat aagatttgat tcattccagt 540
tgctttgtat attaaagtat aatagaactg gccacttctt ttgggttatg cagcctgagt 600
gaagagataa atttcatatc actttagcac attccatcta gaagacgtgt atggaagttg 660
agcctgaata gaatatttgg ttttctattc aggatgttcc catagtaagg agagtatttt 720
tctacatata tcagtaagca gacatgatta cttcagagct ttcaaagcta gatactgtac 780
cttgcatatt ccaacacaat tggtaaattt atccccaaga tgcatggtat gcatactttg 840
tattattaaa accaaaaaag aaaagttaca gtctactggc tggtgtgcaa ataatttgtt 900
gctatttttc accttgttcc tgtactacaa gcataaatga acagttgcag tagttttctt 960
tacgttaagg gtttgtaata cacctaagat aatcatatat gcagattgta atgaaatatt 1020
tttgtgtatg tattccaggt tcagctcaac tactgttt 1058

<210> SEQ ID NO 25
<211> LENGTH: 53
<212> TYPE: DNA
<213> ORGANISM: Artificial
<220> FEATURE:
<223> OTHER INFORMATION: PCR primer

<400> SEQUENCE: 25
tttaagaagg agatatacat gaattctgtc tggtttacat agaaggagga act 53

<210> SEQ ID NO 26
<211> LENGTH: 50
<212> TYPE: DNA
<213> ORGANISM: Artificial
<220> FEATURE:
<223> OTHER INFORMATION: PCR primer

<400> SEQUENCE: 26
gaattctaca gattttgttt tattaaacag tagttgagct gaacctggaa 50

<210> SEQ ID NO 27
<211> LENGTH: 312
<212> TYPE: DNA
<213> ORGANISM: Artificial
<220> FEATURE:
<223> OTHER INFORMATION: Homo sapiens sequence with mutation

<400> SEQUENCE: 27
aataaaacaa aatctgtaga attcacgttt tgtaatgaca ctgtcgtcat tccatgcttt 60
gttactaata tggaggcaca aaacactact gaagtatacg taaagtggaa atttaaagga 120
agagatatct acacctttga tggagctcta aacaagtcca ctgtccccac tgactttagt 180
agtgcaaaaa ttgaagtctc acaattacta aaaggagatg cctctttgaa gatggataag 240

```
agtgatgctg tctcacacac aggaaactac acttgtgaag taacagaatt aaccagagaa    300

ggtgaaacga tc                                                        312


<210> SEQ ID NO 28
<211> LENGTH: 47
<212> TYPE: DNA
<213> ORGANISM: Artificial
<220> FEATURE:
<223> OTHER INFORMATION: PCR primer

<400> SEQUENCE: 28

gttcagctca actactgttt aataaaacaa aatctgtaga attcacg                   47


<210> SEQ ID NO 29
<211> LENGTH: 49
<212> TYPE: DNA
<213> ORGANISM: Artificial
<220> FEATURE:
<223> OTHER INFORMATION: PCR primer

<400> SEQUENCE: 29

gtttagagct ccatcaaagg tgtagatatc tcttccttta aatttccac                 49


<210> SEQ ID NO 30
<211> LENGTH: 49
<212> TYPE: DNA
<213> ORGANISM: Artificial
<220> FEATURE:
<223> OTHER INFORMATION: PCR primer

<400> SEQUENCE: 30

gtggaaattt aaaggaagag atatctacac ctttgatgga gctctaaac                 49


<210> SEQ ID NO 31
<211> LENGTH: 47
<212> TYPE: DNA
<213> ORGANISM: Artificial
<220> FEATURE:
<223> OTHER INFORMATION: PCR primer

<400> SEQUENCE: 31

gtgcggtttt tcagctctat gatcgtttca ccttctctgg ttaattc                   47


<210> SEQ ID NO 32
<211> LENGTH: 1149
<212> TYPE: DNA
<213> ORGANISM: Mus musculus

<400> SEQUENCE: 32

atagagctga aaaaccgcac gggtaagtga cacagtttgc ctgttttgaa acgtgtgttg     60

agatatggtt gccactgtgg gagtgctgta aggtggaacc ttgcagaagt cactaggagg    120

aattaaggct cttcttgggc aagtgggcta gccatctgga tagaaagtga gtctggcact    180

cgtgtttctt tctcttttac acacacacaa acacatacac acacacacac acacacacac    240

acacacacac acacacacac acacactcac tcactcactc ttcatctagc acatctacag    300

cattgtgagg tagcacaatc ctcctcagaa gctgagcagg tgtcagcacc atgcagtgga    360

acttctaggc ccaagaacca gaaaccaagt taagctgctt atcagatacc tcctcctggt    420

cctgtgttac agcaggagaa aacagactga aagcaagcaa aagtaagacc gtaaaattcc    480

taaaggcctc ctgcatccta gtgatgctga ccctcttaga aagagcacag tagtagccag    540
```

```
acttgtctct catctatagc tctttccctc aggagcaagg cccagcctca gctatataac    600

atatttgagg ctagcctggg caacaggaaa cctcatgtta aaaacaaccc ttctgatgac    660

gtaatgggtg tttctgttcg ttgtcatcaa atgtaattta tctgagtatg gtggcccatg    720

actgatctta gcaccccgga ggctgagaca ggaggattgc tgcaaattgg aggcaaccct    780

ggactctgta agtgagttac agaagaacct cagggcaaga cctcacctta ccaagccaag    840

aaacttttgc aaacaaaatg tactttttat tattctatga atttgtaaag ttcctcctgg    900

ttatttcgtc tttttgtggt cttatagcct tcaacactga ccaaggatca gcctgttctt    960

acgaggagga gaaaggaggt tgcaaattag gtaatcatgc tgattcctgg aggcttctgt   1020

ggccagcttg ctacactggc cagcaactgg gaagcaggga ttcaacttaa ccgaattgaa   1080

ttcagtcttg atgctagcgt ccagactttt catgagtggg ttggtgagtt gcggacagca   1140

gtgttgtta                                                           1149
```

<210> SEQ ID NO 33
<211> LENGTH: 47
<212> TYPE: DNA
<213> ORGANISM: Artificial
<220> FEATURE:
<223> OTHER INFORMATION: PCR primer

<400> SEQUENCE: 33

```
ccagagaagg tgaaacgatc atagagctga aaaaccgcac gggtaag                   47
```

<210> SEQ ID NO 34
<211> LENGTH: 50
<212> TYPE: DNA
<213> ORGANISM: Artificial
<220> FEATURE:
<223> OTHER INFORMATION: PCR primer

<400> SEQUENCE: 34

```
ttgttagcag ccggatctca ggatcctaac aacactgctg tccgcaactc                50
```

<210> SEQ ID NO 35
<211> LENGTH: 25
<212> TYPE: DNA
<213> ORGANISM: Artificial
<220> FEATURE:
<223> OTHER INFORMATION: PCR primer

<400> SEQUENCE: 35

```
acccttagcc agagagcaca gagac                                           25
```

<210> SEQ ID NO 36
<211> LENGTH: 25
<212> TYPE: DNA
<213> ORGANISM: Artificial
<220> FEATURE:
<223> OTHER INFORMATION: PCR primer

<400> SEQUENCE: 36

```
tggggacagt ggacttgttt agagc                                           25
```

<210> SEQ ID NO 37
<211> LENGTH: 25
<212> TYPE: DNA
<213> ORGANISM: Artificial
<220> FEATURE:
<223> OTHER INFORMATION: PCR primer

<400> SEQUENCE: 37
acactgtcgt cattccatgc tttgt 25

<210> SEQ ID NO 38
<211> LENGTH: 25
<212> TYPE: DNA
<213> ORGANISM: Artificial
<220> FEATURE:
<223> OTHER INFORMATION: PCR primer

<400> SEQUENCE: 38
acctggttct caaagtgtca ccacc 25

<210> SEQ ID NO 39
<211> LENGTH: 20
<212> TYPE: DNA
<213> ORGANISM: Artificial
<220> FEATURE:
<223> OTHER INFORMATION: PCR primer

<400> SEQUENCE: 39
gtcatccctt gcatcgtccg 20

<210> SEQ ID NO 40
<211> LENGTH: 22
<212> TYPE: DNA
<213> ORGANISM: Artificial
<220> FEATURE:
<223> OTHER INFORMATION: PCR primer

<400> SEQUENCE: 40
acttcgcaag tgtagtttcc ca 22

<210> SEQ ID NO 41
<211> LENGTH: 21
<212> TYPE: DNA
<213> ORGANISM: Artificial
<220> FEATURE:
<223> OTHER INFORMATION: PCR primer

<400> SEQUENCE: 41
acactgtcgt cattccatgc t 21

<210> SEQ ID NO 42
<211> LENGTH: 21
<212> TYPE: DNA
<213> ORGANISM: Artificial
<220> FEATURE:
<223> OTHER INFORMATION: PCR primer

<400> SEQUENCE: 42
cctgtgtgtg agacagcatc a 21

<210> SEQ ID NO 43
<211> LENGTH: 28
<212> TYPE: DNA
<213> ORGANISM: Artificial
<220> FEATURE:
<223> OTHER INFORMATION: PCR primer

<400> SEQUENCE: 43
ggtaaattta tccccaagat gcatggta 28

<210> SEQ ID NO 44
<211> LENGTH: 27
<212> TYPE: DNA

<213> ORGANISM: Artificial
<220> FEATURE:
<223> OTHER INFORMATION: PCR primer

<400> SEQUENCE: 44
gccttaattc ctcctagtga cttctgc 27

<210> SEQ ID NO 45
<211> LENGTH: 1928
<212> TYPE: DNA
<213> ORGANISM: Mus musculus

<400> SEQUENCE: 45
cccgggcagc ctgggcggcc gctcctgcct gtcactgctg cggcgctgct ggtcggtcgt 60
ttcccttgaa ggcagcagcg gaggcggcgg ctgctccaga cacctgcggc ggcgaccccc 120
cggcggcgcg gagatgtggc ccttggcggc ggcgctgttg ctgggctcct gctgctgcgg 180
ttcagctcaa ctactgttta gtaacgtcaa ctccatagag ttcacttcat gcaatgaaac 240
tgtggtcatc ccttgcatcg tccgtaatgt ggaggcgcaa agcaccgaag aaatgtttgt 300
gaagtggaag ttgaacaaat cgtatatttt catctatgat ggaaataaaa atagcactac 360
tacagatcaa aactttacca gtgcaaaaat ctcagtctca gacttaatca atggcattgc 420
ctctttgaaa atggataagc gcgatgccat ggtgggaaac tacacttgcg aagtgacaga 480
gttatccaga gaaggcaaaa cagttataga gctgaaaaac cgcacggcct tcaacactga 540
ccaaggatca gcctgttctt acgaggagga gaaaggaggt tgcaaattag tttcgtggtt 600
ttctccaaat gaaaagatcc tcattgttat tttcccaatt ttggctatac tcctgttctg 660
gggaaagttt ggtattttaa cactcaaata taaatccagc catacgaata agagaatcat 720
tctgctgctc gttgccgggc tggtgctcac agtcatcgtg gttgttggag ccatccttct 780
catcccagga gaaaagcccg tgaagaatgc ttctggactt ggcctcattg taatctctac 840
ggggatatta atactacttc agtacaatgt gtttatgaca gcttttggaa tgacctcttt 900
caccattgcc atattgatca ctcaagtgct gggctacgtc cttgctttgg tcgggctgtg 960
tctctgcatc atggcatgtg agccagtgca cggccccctt ttgatttcag gtttggggat 1020
catagctcta gcagaactac ttggattagt ttatatgaag tttgtcgctt ccaaccagag 1080
gactatccaa cctcctagga ataggtgaag ggaagtgacg gactgtaact tggaagtcag 1140
aaatggaaga atacagttgt ctaagcacca ggtcttcacg actcacagct ggaaggaaca 1200
gacaacagta actgacttcc atccaggaaa acatgtcaca taaatgatta ctaagtttat 1260
attcaaagca gctgtacttt acataataaa aaaaatatga tgtgctgtgt aaccaattgg 1320
aatcccattt ttctattgtt tctactcaac taggggcaaa cgtttcaggg gcaacttcca 1380
agaatgatgc ttgttagatc ctagagtctc tgaacactga gtttaaattg attccgagtg 1440
agactcgcca agcactaacc tgagggttag ttacccagag atacctatga aaaacagtgg 1500
tatccagcaa gccttagtaa actcaggttg ccagcagctt tgccacttcc gctgctagct 1560
gaataacaag actgccactt ctgggtcata gtgatagaga ctgaagtaga aaaacgaatg 1620
tggttgggca aatcccgtgt ggcccctctg tgtgctatga tattgatggc actggtgtct 1680
tcattcttgg gggttgccat cattcacaca cacccctttg acatacagtg caccccagtt 1740
ttgaatacat ttttttgca ccctgtcccg ttctgctact ttgatttgcg ttatgatata 1800
tatatatata tataatacct tttctcctct ttaaacatgg tcctgtgaca caatagtcag 1860
ttgcagaaag gagccagact tattcgcaaa gcactgtgct caaactcttc agaaaaaaaa 1920
aaaaaaaa 1928

<210> SEQ ID NO 46
<211> LENGTH: 3101
<212> TYPE: DNA
<213> ORGANISM: Mus musculus

<400> SEQUENCE: 46
tggtgaaagc agaagcagcg cctacaccgg gagagcaggg aggaggagtt ggactgaggt 60
tgggcggctc cgaggtccag ggcgagcttg gccagaggga gtagagagca gcggggctgc 120
gcagggacgc gtgccgtgag ttccggtgag cgtgtgtgtc ccatgctccc gtctttcagg 180
ccggcccagg acacgaagcc ggaagagagc tggctggagg gacgggggcc gtgagcagag 240
agtgcaaccc gcgcagcccc ggggacaggc tgattcttgg cgctctccgc cggagcctgc 300
ccagggctgg gtgtgaggct ggcgtcacgt caacgagcag aggcggccag gcggggcgga 360
gtgcgcgtgc gcggggcggc gagcacgcgc gcgcgcgcac ccccgggcag cctgggcggc 420
cgctcctgcc tgtcactgct gcggcgctgc tggtcggtcg tttcccttga aggcagcagc 480
ggaggcggcg gctgctccag acacctgcgg cggcgacccc ccggcggcgc ggagatgtgg 540
cccttggcgg cggcgctgtt gctgggctcc tgctgctgcg gttcagctca actactgttt 600
agtaacgtca actccataga gttcacttca tgcaatgaaa ctgtggtcat cccttgcatc 660
gtccgtaatg tggaggcgca aagcaccgaa gaaatgtttg tgaagtggaa gttgaacaaa 720
tcgtatattt tcatctatga tggaaataaa aatagcacta ctacagatca aaactttacc 780
agtgcaaaaa tctcagtctc agacttaatc aatggcattg cctctttgaa aatggataag 840
cgcgatgcca tggtgggaaa ctacacttgc gaagtgacag agttatccag agaaggcaaa 900
acagttatag agctgaaaaa ccgcacggcc ttcaacactg accaaggatc agcctgttct 960
tacgaggagg agaaaggagg ttgcaaatta gtttcgtggt tttctccaaa tgaaaagatc 1020
ctcattgtta ttttcccaat tttggctata ctcctgttct ggggaaagtt tggtatttta 1080
acactcaaat ataaatccag ccatacgaat aagagaatca ttctgctgct cgttgccggg 1140
ctggtgctca cagtcatcgt ggttgttgga gccatccttc tcatcccagg agaaaagccc 1200
gtgaagaatg cttctggact tggcctcatt gtaatctcta cggggatatt aatactactt 1260
cagtacaatg tgtttatgac agcttttgga atgacctctt tcaccattgc catattgatc 1320
actcaagtgc tgggctacgt ccttgctttg gtcgggctgt gtctctgcat catggcatgt 1380
gagccagtgc acggcccccct tttgatttca ggtttgggga tcatagctct agcagaacta 1440
cttggattag tttatatgaa gtttgtcgag tggagagaga caccttcggt cagttgagag 1500
gcaagaagga aagcttccaa ccagaggact atccaacctc ctaggaatag gtgaagggaa 1560
gtgacggact gtaacttgga agtcagaaat ggaagaatac agttgtctaa gcaccaggtc 1620
ttcacgactc acagctggaa ggaacagaca acagtaactg acttccatcc aggaaaacat 1680
gtcacataaa tgattactaa gtttatattc aaagcagctg tactttacat aataaaaaaa 1740
atatgatgtg ctgtgtaacc aattggaatc ccatttttct attgtttcta ctcaactagg 1800
ggcaaacgtt tcaggggcaa cttccaagaa tgatgcttgt tagatcctag agtctctgaa 1860
cactgagttt aaattgattc cgagtgagac tcgccaagca ctaacctgag ggttagttac 1920
ccagagatac ctatgaaaaa cagtggtatc cagcaagcct tagtaaactc aggttgccag 1980
cagctttgcc acttccgctg ctagctgaat aacaagactg ccacttctgg gtcatagtga 2040

```
tagagactga agtagaaaaa cgaatgtggt tgggcaaatc ccgtgtggcc cctctgtgtg   2100
ctatgatatt gatggcactg gtgtcttcat tcttgggggt tgccatcatt cacacacacc   2160
cctttgacat acagtgcacc ccagttttga atacattttt tttgcaccct gtcccgttct   2220
gctactttga tttgcgttat gatatatata tatatatata atacctttc tcctctttaa   2280
acatggtcct gtgacacaat agtcagttgc agaaaggagc cagacttatt cgcaaagcac   2340
tgtgctcaaa ctcttcagaa aaaaaggaaa aaaaaaaaaa gctatagttg taacatatgt   2400
attccagacc tctggtttaa aggcaaaaga aaaaaaatct acagtgtttc ttctcatgtt   2460
ttctgatcgg aggcatgaca aagcaagact gaaatctgaa ctgtgtctcc tgcatggcaa   2520
cacgtgtctc cgtcaggccc tcgcaaggcc cggggagggg gttctacgcc tcttgtctct   2580
ttgttgcatg ctgaacactc atcgccttcc tactgtatcc tgcctcctgc agcctccctc   2640
ttcctcctcc tcttcctctt cctcctcttc ctcctcctcc tcctcttcct ccaagtttga   2700
aaggtcaaac aaaactacca cattccctac ccagttagaa gaaaaccacc gtcctgacag   2760
ttgtgatcgc atggagtact tttagattat tagcacctgt ttttacctcg tttgtgggcg   2820
tgtttgtatg tgcacatgta tgaagtcggc acatgcacct tctgtatggg cagaggcgtg   2880
gcatctacag aagagcagat gccaactttg tgcttttagt gaatacatta aaaaaaaaaa   2940
accaacggtc cttattgagt ggaattctat ttgatgcaaa tatttgagct ctttaagact   3000
ttaaaactag ataatgtgcc aagcttttag gactgctcac cagtgccctc tgaagaaaca   3060
ccagtacttt ttcctgtttg tgtaataaag gcatatttgt a                        3101
```

```
<210> SEQ ID NO 47
<211> LENGTH: 3114
<212> TYPE: DNA
<213> ORGANISM: Mus musculus

<400> SEQUENCE: 47

tggtgaaagc agaagcagcg cctacaccgg gagagcaggg aggaggagtt ggactgaggt     60
tgggcggctc cgaggtccag ggcgagcttg gccagaggga gtagagagca gcggggctgc    120
gcagggacgc gtgccgtgag ttccggtgag cgtgtgtgtc ccatgctccc gtctttcagg    180
ccggcccagg acacgaagcc ggaagagagc tggctggagg gacgggggcc gtgagcagag    240
agtgcaaccc gcgcagcccc ggggacaggc tgattcttgg cgctctccgc cggagcctgc    300
ccagggctgg gtgtgaggct ggcgtcacgt caacgagcag aggcggccag gcggggcgga    360
gtgcgcgtgc gcggggcggc gagcacgcgc gcgcgcgcac ccccgggcag cctgggcggc    420
cgctcctgcc tgtcactgct gcggcgctgc tggtcggtcg tttcccttga aggcagcagc    480
ggaggcggcg gctgctccag acacctgcgg cggcgacccc ccggcggcgc ggagatgtgg    540
cccttggcgg cggcgctgtt gctgggctcc tgctgctgcg gttcagctca actactgttt    600
agtaacgtca actccataga gttcacttca tgcaatgaaa ctgtggtcat cccttgcatc    660
gtccgtaatg tggaggcgca aagcaccgaa gaaatgtttg tgaagtggaa gttgaacaaa    720
tcgtatattt tcatctatga tggaaataaa aatagcacta ctacagatca aaactttacc    780
agtgcaaaaa tctcagtctc agacttaatc aatggcattg cctctttgaa aatggataag    840
cgcgatgcca tggtgggaaa ctacacttgc gaagtgacag agttatccag agaaggcaaa    900
acagttatag agctgaaaaa ccgcacggcc ttcaacactg accaaggatc agcctgttct    960
tacgaggagg agaaaggagg ttgcaaatta gtttcgtggt tttctccaaa tgaaaagatc   1020
ctcattgtta ttttcccaat tttggctata ctcctgttct ggggaaagtt tggtatttta   1080
```

```
acactcaaat ataaatccag ccatacgaat aagagaatca ttctgctgct cgttgccggg   1140

ctggtgctca cagtcatcgt ggttgttgga gccatccttc tcatcccagg agaaaagccc   1200

gtgaagaatg cttctggact tggcctcatt gtaatctcta cggggatatt aatactactt   1260

cagtacaatg tgtttatgac agcttttgga atgacctctt tcaccattgc catattgatc   1320

actcaagtgc tgggctacgt ccttgctttg gtcgggctgt gtctctgcat catggcatgt   1380

gagccagtgc acggccccct tttgatttca ggtttgggga tcatagctct agcagaacta   1440

cttggattag tttatatgaa gtttgtcgct tccaaccaga ggactatcca acctcctagg   1500

aaagctgtag aggaacccct taacgcattt aaagagtcaa aaggaatgat gaatgacgaa   1560

taggtgaagg gaagtgacgg actgtaactt ggaagtcaga aatggaagaa tacagttgtc   1620

taagcaccag gtcttcacga ctcacagctg gaaggaacag acaacagtaa ctgacttcca   1680

tccaggaaaa catgtcacat aaatgattac taagtttata ttcaaagcag ctgtacttta   1740

cataataaaa aaaatatgat gtgctgtgta accaattgga atcccatttt tctattgttt   1800

ctactcaact aggggcaaac gtttcagggg caacttccaa gaatgatgct tgttagatcc   1860

tagagtctct gaacactgag tttaaattga ttccgagtga gactcgccaa gcactaacct   1920

gagggttagt tacccagaga tacctatgaa aaacagtggt atccagcaag ccttagtaaa   1980

ctcaggttgc cagcagcttt gccacttccg ctgctagctg aataacaaga ctgccacttc   2040

tgggtcatag tgatagagac tgaagtagaa aaacgaatgt ggttgggcaa atcccgtgtg   2100

gcccctctgt gtgctatgat attgatggca ctggtgtctt cattcttggg ggttgccatc   2160

attcacacac accccttga catacagtgc accccagttt tgaatacatt ttttttgcac   2220

cctgtcccgt tctgctactt tgatttgcgt tatgatatat atatatatat ataatacctt   2280

ttctcctctt taaacatggt cctgtgacac aatagtcagt tgcagaaagg agccagactt   2340

attcgcaaag cactgtgctc aaactcttca gaaaaaaagg aaaaaaaaaa aaagctatag   2400

ttgtaacata tgtattccag acctctggtt taaaggcaaa agaaaaaaaa tctacagtgt   2460

ttcttctcat gttttctgat cggaggcatg acaaagcaag actgaaatct gaactgtgtc   2520

tcctgcatgg caacacgtgt ctccgtcagg ccctcgcaag gcccggggag ggggttctac   2580

gcctcttgtc tctttgttgc atgctgaaca ctcatcgcct tcctactgta tcctgcctcc   2640

tgcagcctcc ctcttcctcc tcctcttcct cttcctcctc ttcctcctcc tcctcctctt   2700

cctccaagtt tgaaaggtca aacaaaacta ccacattccc tacccagtta gaagaaaacc   2760

accgtcctga cagttgtgat cgcatggagt actttagat tattagcacc tgtttttacc   2820

tcgtttgtgg gcgtgtttgt atgtgcacat gtatgaagtc ggcacatgca ccttctgtat   2880

gggcagaggc gtggcatcta cagaagagca gatgccaact ttgtgctttt agtgaataca   2940

ttaaaaaaaa aaaaccaacg gtccttattg agtggaattc tatttgatgc aaatatttga   3000

gctctttaag actttaaaac tagataatgt gccaagcttt taggactgct caccagtgcc   3060

ctctgaagaa acaccagtac tttttcctgt ttgtgtaata aaggcatatt tgta         3114
```

<210> SEQ ID NO 48
<211> LENGTH: 3081
<212> TYPE: DNA
<213> ORGANISM: Mus musculus

<400> SEQUENCE: 48

```
tggtgaaagc agaagcagcg cctacaccgg gagagcaggg aggaggagtt ggactgaggt     60
```

-continued

```
tgggcggctc cgaggtccag ggcgagcttg gccagaggga gtagagagca gcggggctgc    120
gcagggacgc gtgccgtgag ttccggtgag cgtgtgtgtc ccatgctccc gtctttcagg    180
ccggcccagg acacgaagcc ggaagagagc tggctggagg gacgggggcc gtgagcagag    240
agtgcaaccc gcgcagcccc ggggacaggc tgattcttgg cgctctccgc cggagcctgc    300
ccagggctgg gtgtgaggct ggcgtcacgt caacgagcag aggcggccag gcggggcgga    360
gtgcgcgtgc gcggggcggc gagcacgcgc gcgcgcgcac ccccgggcag cctgggcggc    420
cgctcctgcc tgtcactgct gcggcgctgc tggtcggtcg tttcccttga aggcagcagc    480
ggaggcggcg gctgctccag acacctgcgg cggcgacccc ccggcggcgc ggagatgtgg    540
cccttggcgg cggcgctgtt gctgggctcc tgctgctgcg gttcagctca actactgttt    600
agtaacgtca actccataga gttcacttca tgcaatgaaa ctgtggtcat cccttgcatc    660
gtccgtaatg tggaggcgca aagcaccgaa gaaatgtttg tgaagtggaa gttgaacaaa    720
tcgtatattt tcatctatga tggaaataaa aatagcacta ctacagatca aaactttacc    780
agtgcaaaaa tctcagtctc agacttaatc aatggcattg cctctttgaa aatggataag    840
cgcgatgcca tggtgggaaa ctacacttgc gaagtgacag agttatccag agaaggcaaa    900
acagttatag agctgaaaaa ccgcacggcc ttcaacactg accaaggatc agcctgttct    960
tacgaggagg agaaaggagg ttgcaaatta gtttcgtggt tttctccaaa tgaaaagatc   1020
ctcattgtta ttttcccaat tttggctata ctcctgttct ggggaaagtt tggtatttta   1080
acactcaaat ataaatccag ccatacgaat aagagaatca ttctgctgct cgttgccggg   1140
ctggtgctca cagtcatcgt ggttgttgga gccatccttc tcatcccagg agaaaagccc   1200
gtgaagaatg cttctggact tggcctcatt gtaatctcta cggggatatt aatactactt   1260
cagtacaatg tgtttatgac agcttttgga atgacctctt tcaccattgc catattgatc   1320
actcaagtgc tgggctacgt ccttgctttg gtcgggctgt gtctctgcat catggcatgt   1380
gagccagtgc acggccccct tttgatttca ggtttgggga tcatagctct agcagaacta   1440
cttggattag tttatatgaa gtttgtcgct tccaaccaga ggactatcca acctcctagg   1500
aaagctgtag aggaacccct taacgaatag gtgaagggaa gtgacggact gtaacttgga   1560
agtcagaaat ggaagaatac agttgtctaa gcaccaggtc ttcacgactc acagctggaa   1620
ggaacagaca acagtaactg acttccatcc aggaaaacat gtcacataaa tgattactaa   1680
gtttatattc aaagcagctg tactttacat aataaaaaaa atatgatgtg ctgtgtaacc   1740
aattggaatc ccatttttct attgtttcta ctcaactagg ggcaaacgtt tcaggggcaa   1800
cttccaagaa tgatgcttgt tagatcctag agtctctgaa cactgagttt aaattgattc   1860
cgagtgagac tcgccaagca ctaacctgag ggttagttac ccagagatac ctatgaaaaa   1920
cagtggtatc cagcaagcct tagtaaactc aggttgccag cagctttgcc acttccgctg   1980
ctagctgaat aacaagactg ccacttctgg gtcatagtga tagagactga agtagaaaaa   2040
cgaatgtggt tgggcaaatc ccgtgtggcc cctctgtgtg ctatgatatt gatggcactg   2100
gtgtcttcat tcttgggggt tgccatcatt cacacacacc cctttgacat acagtgcacc   2160
ccagttttga atacattttt tttgcaccct gtcccgttct gctactttga tttgcgttat   2220
gatatatata tatatatata atacctttc tcctctttaa acatggtcct gtgacacaat   2280
agtcagttgc agaaaggagc cagacttatt cgcaaagcac tgtgctcaaa ctcttcagaa   2340
aaaaaggaaa aaaaaaaaaa gctatagttg taacatatgt attccagacc tctggtttaa   2400
aggcaaaaga aaaaaaatct acagtgtttc ttctcatgtt ttctgatcgg aggcatgaca   2460
```

aagcaagact gaaatctgaa ctgtgtctcc tgcatggcaa cacgtgtctc cgtcaggccc 2520
tcgcaaggcc cggggagggg gttctacgcc tcttgtctct ttgttgcatg ctgaacactc 2580
atcgccttcc tactgtatcc tgcctcctgc agcctccctc ttcctcctcc tcttcctctt 2640
cctcctcttc ctcctcctcc tcctcttcct ccaagtttga aaggtcaaac aaaactacca 2700
cattccctac ccagttagaa gaaaaccacc gtcctgacag ttgtgatcgc atggagtact 2760
tttagattat tagcacctgt ttttacctcg tttgtgggcg tgtttgtatg tgcacatgta 2820
tgaagtcggc acatgcacct tctgtatggg cagaggcgtg gcatctacag aagagcagat 2880
gccaactttg tgcttttagt gaatacatta aaaaaaaaaa accaacggtc cttattgagt 2940
ggaattctat ttgatgcaaa tatttgagct ctttaagact ttaaaactag ataatgtgcc 3000
aagcttttag gactgctcac cagtgccctc tgaagaaaca ccagtacttt ttcctgtttg 3060
tgtaataaag gcatatttgt a 3081

<210> SEQ ID NO 49
<211> LENGTH: 3024
<212> TYPE: DNA
<213> ORGANISM: Mus musculus

<400> SEQUENCE: 49
tggtgaaagc agaagcagcg cctacaccgg gagagcaggg aggaggagtt ggactgaggt 60
tgggcggctc cgaggtccag ggcgagcttg gccagaggga gtagagagca gcggggctgc 120
gcagggacgc gtgccgtgag ttccggtgag cgtgtgtgtc ccatgctccc gtctttcagg 180
ccggcccagg acacgaagcc ggaagagagc tggctggagg gacgggggcc gtgagcagag 240
agtgcaaccc gcgcagcccc ggggacaggc tgattcttgg cgctctccgc cggagcctgc 300
ccagggctgg gtgtgaggct ggcgtcacgt caacgagcag aggcggccag gcggggcgga 360
gtgcgcgtgc gcggggcggc gagcacgcgc gcgcgcgcac ccccgggcag cctgggcggc 420
cgctcctgcc tgtcactgct gcggcgctgc tggtcggtcg tttcccttga aggcagcagc 480
ggaggcggcg gctgctccag acacctgcgg cggcgacccc ccggcggcgc ggagatgtgg 540
cccttggcgg cggcgctgtt gctgggctcc tgctgctgcg gttcagctca actactgttt 600
agtaacgtca actccataga gttcacttca tgcaatgaaa ctgtggtcat cccttgcatc 660
gtccgtaatg tggaggcgca aagcaccgaa gaaatgtttg tgaagtggaa gttgaacaaa 720
tcgtatattt tcatctatga tggaaataaa aatagcacta ctacagatca aaactttacc 780
agtgcaaaaa tctcagtctc agacttaatc aatggcattg cctctttgaa aatggataag 840
cgcgatgcca tggtgggaaa ctacacttgc gaagtgacag agttatccag agaaggcaaa 900
acagttatag agctgaaaaa ccgcacggcc ttcaacactg accaaggatc agcctgttct 960
tacgaggagg agaaaggagg ttgcaaatta gtttcgtggt tttctccaaa tgaaaagatc 1020
ctcattgtta ttttcccaat tttggctata ctcctgttct ggggaaagtt tggtatttta 1080
acactcaaat ataaatccag ccatacgaat aagagaatca ttctgctgct cgttgccggg 1140
ctggtgctca cagtcatcgt ggttgttgga gccatccttc tcatcccagg agaaaagccc 1200
gtgaagaatg cttctggact tggcctcatt gtaatctcta cggggatatt aatactactt 1260
cagtacaatg tgtttatgac agcttttgga atgacctctt tcaccattgc catattgatc 1320
actcaagtgc tgggctacgt ccttgctttg gtcgggctgt gtctctgcat catggcatgt 1380
gagccagtgc acggccccct tttgatttca ggtttgggga tcatagctct agcagaacta 1440

```
cttggattag tttatatgaa gtttgtcgaa taggtgaagg gaagtgacgg actgtaactt   1500
ggaagtcaga aatggaagaa tacagttgtc taagcaccag gtcttcacga ctcacagctg   1560
gaaggaacag acaacagtaa ctgacttcca tccaggaaaa catgtcacat aaatgattac   1620
taagtttata ttcaaagcag ctgtacttta cataataaaa aaaatatgat gtgctgtgta   1680
accaattgga atcccatttt tctattgttt ctactcaact aggggcaaac gtttcagggg   1740
caacttccaa gaatgatgct tgttagatcc tagagtctct gaacactgag tttaaattga   1800
ttccgagtga gactcgccaa gcactaacct gagggttagt tacccagaga tacctatgaa   1860
aaacagtggt atccagcaag ccttagtaaa ctcaggttgc cagcagcttt gccacttccg   1920
ctgctagctg aataacaaga ctgccacttc tgggtcatag tgatagagac tgaagtagaa   1980
aaacgaatgt ggttgggcaa atcccgtgtg gcccctctgt gtgctatgat attgatggca   2040
ctggtgtctt cattcttggg ggttgccatc attcacacac accccttga catacagtgc   2100
accccagttt tgaatacatt tttttgcac cctgtcccgt tctgctactt tgatttgcgt   2160
tatgatatat atatatatat ataataccttt ttctcctctt taaacatggt cctgtgacac   2220
aatagtcagt tgcagaaagg agccagactt attcgcaaag cactgtgctc aaactcttca   2280
gaaaaaaagg aaaaaaaaaa aaagctatag ttgtaacata tgtattccag acctctggtt   2340
taaaggcaaa agaaaaaaaa tctacagtgt ttcttctcat gttttctgat cggaggcatg   2400
acaaagcaag actgaaatct gaactgtgtc tcctgcatgg caacacgtgt ctccgtcagg   2460
ccctcgcaag gcccggggag gggttctac gcctcttgtc tctttgttgc atgctgaaca   2520
ctcatcgcct tcctactgta tcctgcctcc tgcagcctcc ctcttcctcc tcctcttcct   2580
cttcctcctc ttcctcctcc tcctcctctt cctccaagtt tgaaaggtca aacaaaacta   2640
ccacattccc tacccagtta gaagaaaacc accgtcctga cagttgtgat cgcatggagt   2700
acttttagat tattagcacc tgtttttacc tcgtttgtgg gcgtgtttgt atgtgcacat   2760
gtatgaagtc ggcacatgca ccttctgtat gggcagaggc gtggcatcta cagaagagca   2820
gatgccaact ttgtgctttt agtgaataca ttaaaaaaaa aaaaccaacg gtccttattg   2880
agtggaattc tatttgatgc aaatatttga gctctttaag actttaaaac tagataatgt   2940
gccaagcttt taggactgct caccagtgcc ctctgaagaa acaccagtac tttttcctgt   3000
ttgtgtaata aaggcatatt tgta                                          3024
```

<210> SEQ ID NO 50
<211> LENGTH: 3051
<212> TYPE: DNA
<213> ORGANISM: Mus musculus

<400> SEQUENCE: 50

```
tggtgaaagc agaagcagcg cctacaccgg gagagcaggg aggaggagtt ggactgaggt     60
tgggcggctc cgaggtccag ggcgagcttg gccagaggga gtagagagca gcggggctgc    120
gcagggacgc gtgccgtgag ttccggtgag cgtgtgtgtc ccatgctccc gtctttcagg    180
ccggcccagg acacgaagcc ggaagagagc tggctggagg gacgggggcc gtgagcagag    240
agtgcaaccc gcgcagcccc ggggacaggc tgattcttgg cgctctccgc cggagcctgc    300
ccagggctgg gtgtgaggct ggcgtcacgt caacgagcag aggcggccag gcggggcgga    360
gtgcgcgtgc gcggggcggc gagcacgcgc gcgcgcgcac ccccgggcag cctgggcggc    420
cgctcctgcc tgtcactgct gcggcgctgc tggtcggtcg tttcccttga aggcagcagc    480
ggaggcggcg gctgctccag acacctgcgg cggcgacccc ccggcggcgc ggagatgtgg    540
```

```
cccttggcgg cggcgctgtt gctgggctcc tgctgctgcg gttcagctca actactgttt    600
agtaacgtca actccataga gttcacttca tgcaatgaaa ctgtggtcat cccttgcatc    660
gtccgtaatg tggaggcgca aagcaccgaa gaaatgtttg tgaagtggaa gttgaacaaa    720
tcgtatattt tcatctatga tggaaataaa aatagcacta ctacagatca aaactttacc    780
agtgcaaaaa tctcagtctc agacttaatc aatggcattg cctctttgaa aatggataag    840
cgcgatgcca tggtgggaaa ctacacttgc gaagtgacag agttatccag agaaggcaaa    900
acagttatag agctgaaaaa ccgcacggtt tcgtggtttt ctccaaatga aaagatcctc    960
attgttattt tcccaatttt ggctatactc ctgttctggg gaaagtttgg tattttaaca   1020
ctcaaatata aatccagcca tacgaataag agaatcattc tgctgctcgt tgccgggctg   1080
gtgctcacag tcatcgtggt tgttggagcc atccttctca tcccaggaga aaagcccgtg   1140
aagaatgctt ctggacttgg cctcattgta atctctacgg ggatattaat actacttcag   1200
tacaatgtgt ttatgacagc ttttggaatg acctctttca ccattgccat attgatcact   1260
caagtgctgg gctacgtcct tgctttggtc gggctgtgtc tctgcatcat ggcatgtgag   1320
ccagtgcacg gcccccttt gatttcaggt ttggggatca tagctctagc agaactactt   1380
ggattagttt atatgaagtt tgtcgcttcc aaccagagga ctatccaacc tcctaggaaa   1440
gctgtagagg aacccttaa cgcatttaaa gagtcaaaag gaatgatgaa tgacgaatag   1500
gtgaagggaa gtgacggact gtaacttgga agtcagaaat ggaagaatac agttgtctaa   1560
gcaccaggtc ttcacgactc acagctggaa ggaacagaca acagtaactg acttccatcc   1620
aggaaaacat gtcacataaa tgattactaa gtttatattc aaagcagctg tactttacat   1680
aataaaaaaa atatgatgtg ctgtgtaacc aattggaatc ccatttttct attgtttcta   1740
ctcaactagg ggcaaacgtt tcaggggcaa cttccaagaa tgatgcttgt tagatcctag   1800
agtctctgaa cactgagttt aaattgattc cgagtgagac tcgccaagca ctaacctgag   1860
ggttagttac ccagagatac ctatgaaaaa cagtggtatc cagcaagcct tagtaaactc   1920
aggttgccag cagctttgcc acttccgctg ctagctgaat aacaagactg ccacttctgg   1980
gtcatagtga tagagactga agtagaaaaa cgaatgtggt tgggcaaatc ccgtgtggcc   2040
cctctgtgtg ctatgatatt gatggcactg gtgtcttcat tcttgggggt tgccatcatt   2100
cacacacacc cctttgacat acagtgcacc ccagttttga atacattttt tttgcaccct   2160
gtcccgttct gctactttga tttgcgttat gatatatata tatatatata atacctttc   2220
tcctctttaa acatggtcct gtgacacaat agtcagttgc agaaaggagc cagacttatt   2280
cgcaaagcac tgtgctcaaa ctcttcagaa aaaaaggaaa aaaaaaaaaa gctatagttg   2340
taacatatgt attccagacc tctggtttaa aggcaaaaga aaaaaaatct acagtgtttc   2400
ttctcatgtt ttctgatcgg aggcatgaca aagcaagact gaaatctgaa ctgtgtctcc   2460
tgcatggcaa cacgtgtctc cgtcaggccc tcgcaaggcc cggggagggg gttctacgcc   2520
tcttgtctct ttgttgcatg ctgaacactc atcgccttcc tactgtatcc tgcctcctgc   2580
agcctccctc ttcctcctcc tcttcctctt cctcctcttc ctcctcctcc tcctcttcct   2640
ccaagtttga aaggtcaaac aaaactacca cattccctac ccagttagaa gaaaaccacc   2700
gtcctgacag ttgtgatcgc atggagtact tttagattat tagcacctgt ttttacctcg   2760
tttgtgggcg tgtttgtatg tgcacatgta tgaagtcggc acatgcacct tctgtatggg   2820
cagaggcgtg gcatctacag aagagcagat gccaactttg tgcttttagt gaatacatta   2880
```

```
aaaaaaaaaa accaacggtc cttattgagt ggaattctat ttgatgcaaa tatttgagct   2940

ctttaagact ttaaaactag ataatgtgcc aagcttttag gactgctcac cagtgccctc   3000

tgaagaaaca ccagtacttt ttcctgtttg tgtaataaag gcatatttgt a            3051
```

<210> SEQ ID NO 51
<211> LENGTH: 2993
<212> TYPE: DNA
<213> ORGANISM: Mus musculus

<400> SEQUENCE: 51

```
tggtgaaagc agaagcagcg cctacaccgg gagagcaggg aggaggagtt ggactgaggt     60

tgggcggctc cgaggtccag ggcgagcttg gccagaggga gtagagagca gcggggctgc    120

gcagggacgc gtgccgtgag ttccggtgag cgtgtgtgtc ccatgctccc gtctttcagg    180

ccggcccagg acacgaagcc ggaagagagc tggctggagg gacgggggcc gtgagcagag    240

agtgcaaccc gcgcagcccc ggggacaggc tgattcttgg cgctctccgc cggagcctgc    300

ccagggctgg gtgtgaggct ggcgtcacgt caacgagcag aggcggccag gcggggcgga    360

gtgcgcgtgc gcggggcggc gagcacgcgc gcgcgcgcac ccccgggcag cctgggcggc    420

cgctcctgcc tgtcactgct gcggcgctgc tggtcggtcg tttcccttga aggcagcagc    480

ggaggcggcg gctgctccag acacctgcgg cggcgacccc ccggcggcgc ggagatgtgg    540

cccttggcgg cggcgctgtt gctgggctcc tgctgctgcg gttcagctca actactgttt    600

agtaacgtca actccataga gttcacttca tgcaatgaaa ctgtggtcat cccttgcatc    660

gtccgtaatg tggaggcgca aagcaccgaa gaaatgtttg tgaagtggaa gttgaacaaa    720

tcgtatattt tcatctatga tggaaataaa aatagcacta ctacagatca aaactttacc    780

agtgcaaaaa tctcagtctc agacttaatc aatggcattg cctctttgaa aatggataag    840

cgcgatgcca tggtgggaaa ctacacttgc gaagtgacag agttatccag agaaggcaaa    900

acagttatag agctgaaaaa ccgcacggtt tcgtggtttt ctccaaatga aaagatcctc    960

attgttattt tcccaatttt ggctatactc ctgttctggg gaaagtttgg tattttaaca   1020

ctcaaatata aatccagcca tacgaataag agaatcattc tgctgctcgt tgccgggctg   1080

gtgctcacag tcatcgtggt tgttggagcc atccttctca tcccaggaga aaagcccgtg   1140

aagaatgctt ctggacttgg cctcattgta atctctacgg ggatattaat actacttcag   1200

tacaatgtgt ttatgacagc ttttggaatg acctctttca ccattgccat attgatcact   1260

caagtgctgg gctacgtcct tgctttggtc gggctgtgtc tctgcatcat ggcatgtgag   1320

ccagtgcacg gcccccttt gatttcaggt ttggggatca tagctctagc agaactactt   1380

ggattagttt atatgaagtt tgtcgcttcc aaccagagga ctatccaacc tcctaggaat   1440

aggtgaaggg aagtgacgga ctgtaacttg gaagtcagaa atggaagaat acagttgtct   1500

aagcaccagg tcttcacgac tcacagctgg aaggaacaga caacagtaac tgacttccat   1560

ccaggaaaac atgtcacata aatgattact aagtttatat tcaaagcagc tgtactttac   1620

ataataaaaa aaatatgatg tgctgtgtaa ccaattggaa tcccattttt ctattgtttc   1680

tactcaacta ggggcaaacg tttcaggggc aacttccaag aatgatgctt gttagatcct   1740

agagtctctg aacactgagt ttaaattgat tccgagtgag actcgccaag cactaacctg   1800

agggttagtt acccagagat acctatgaaa aacagtggta tccagcaagc cttagtaaac   1860

tcaggttgcc agcagctttg ccacttccgc tgctagctga ataacaagac tgccacttct   1920

gggtcatagt gatagagact gaagtagaaa aacgaatgtg gttgggcaaa tcccgtgtgg   1980
```

```
cccctctgtg tgctatgata ttgatggcac tggtgtcttc attcttgggg gttgccatca   2040

ttcacacaca cccctttgac atacagtgca ccccagtttt gaatacattt tttttgcacc   2100

ctgtcccgtt ctgctacttt gatttgcgtt atgatatata tatatatata taataccttt   2160

tctcctcttt aaacatggtc ctgtgacaca atagtcagtt gcagaaagga gccagactta   2220

ttcgcaaagc actgtgctca aactcttcag aaaaaaagga aaaaaaaaaa aagctatagt   2280

tgtaacatat gtattccaga cctctggttt aaaggcaaaa gaaaaaaaat ctacagtgtt   2340

tcttctcatg ttttctgatc ggaggcatga caaagcaaga ctgaaatctg aactgtgtct   2400

cctgcatggc aacacgtgtc tccgtcaggc cctcgcaagg cccggggagg gggttctacg   2460

cctcttgtct ctttgttgca tgctgaacac tcatcgcctt cctactgtat cctgcctcct   2520

gcagcctccc tcttcctcct cctcttcctc ttcctcctct tcctcctcct cctcctcttc   2580

ctccaagttt gaaaggtcaa acaaaactac cacattccct acccagttag aagaaaacca   2640

ccgtcctgac agttgtgatc gcatggagta cttttagatt attagcacct gtttttacct   2700

cgtttgtggg cgtgtttgta tgtgcacatg tatgaagtcg gcacatgcac cttctgtatg   2760

ggcagaggcg tggcatctac agaagagcag atgccaactt tgtgctttta gtgaatacat   2820

taaaaaaaaa aaaccaacgg tccttattga gtggaattct atttgatgca aatatttgag   2880

ctctttaaga ctttaaaact agataatgtg ccaagctttt aggactgctc accagtgccc   2940

tctgaagaaa caccagtact ttttcctgtt tgtgtaataa aggcatattt gta          2993
```

<210> SEQ ID NO 52
<211> LENGTH: 324
<212> TYPE: PRT
<213> ORGANISM: Mus musculus

<400> SEQUENCE: 52

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190
```

```
Lys Arg Ile Ile Leu Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Ala Ser Asn Gln Arg Thr Ile Gln Pro
305                 310                 315                 320

Pro Arg Asn Arg


<210> SEQ ID NO 53
<211> LENGTH: 320
<212> TYPE: PRT
<213> ORGANISM: Mus musculus

<400> SEQUENCE: 53

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240
```

```
Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Glu Trp Arg Glu Thr Pro Ser Val Ser
305                 310                 315                 320


<210> SEQ ID NO 54
<211> LENGTH: 342
<212> TYPE: PRT
<213> ORGANISM: Mus musculus

<400> SEQUENCE: 54

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300
```

```
Leu Val Tyr Met Lys Phe Val Ala Ser Asn Gln Arg Thr Ile Gln Pro
305                 310                 315                 320

Pro Arg Lys Ala Val Glu Glu Pro Leu Asn Ala Phe Lys Glu Ser Lys
                325                 330                 335

Gly Met Met Asn Asp Glu
            340


<210> SEQ ID NO 55
<211> LENGTH: 331
<212> TYPE: PRT
<213> ORGANISM: Mus musculus

<400> SEQUENCE: 55

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Ala Ser Asn Gln Arg Thr Ile Gln Pro
305                 310                 315                 320

Pro Arg Lys Ala Val Glu Glu Pro Leu Asn Glu
```

325 330

<210> SEQ ID NO 56
<211> LENGTH: 312
<212> TYPE: PRT
<213> ORGANISM: Mus musculus

<400> SEQUENCE: 56

Met Trp Pro Leu Ala Ala Ala Leu Leu Leu Gly Ser Cys Cys Cys Gly
1 5 10 15

Ser Ala Gln Leu Leu Phe Ser Asn Val Asn Ser Ile Glu Phe Thr Ser
20 25 30

Cys Asn Glu Thr Val Val Ile Pro Cys Ile Val Arg Asn Val Glu Ala
35 40 45

Gln Ser Thr Glu Glu Met Phe Val Lys Trp Lys Leu Asn Lys Ser Tyr
50 55 60

Ile Phe Ile Tyr Asp Gly Asn Lys Asn Ser Thr Thr Thr Asp Gln Asn
65 70 75 80

Phe Thr Ser Ala Lys Ile Ser Val Ser Asp Leu Ile Asn Gly Ile Ala
85 90 95

Ser Leu Lys Met Asp Lys Arg Asp Ala Met Val Gly Asn Tyr Thr Cys
100 105 110

Glu Val Thr Glu Leu Ser Arg Glu Gly Lys Thr Val Ile Glu Leu Lys
115 120 125

Asn Arg Thr Ala Phe Asn Thr Asp Gln Gly Ser Ala Cys Ser Tyr Glu
130 135 140

Glu Glu Lys Gly Gly Cys Lys Leu Val Ser Trp Phe Ser Pro Asn Glu
145 150 155 160

Lys Ile Leu Ile Val Ile Phe Pro Ile Leu Ala Ile Leu Leu Phe Trp
165 170 175

Gly Lys Phe Gly Ile Leu Thr Leu Lys Tyr Lys Ser Ser His Thr Asn
180 185 190

Lys Arg Ile Ile Leu Leu Leu Val Ala Gly Leu Val Leu Thr Val Ile
195 200 205

Val Val Val Gly Ala Ile Leu Leu Ile Pro Gly Glu Lys Pro Val Lys
210 215 220

Asn Ala Ser Gly Leu Gly Leu Ile Val Ile Ser Thr Gly Ile Leu Ile
225 230 235 240

Leu Leu Gln Tyr Asn Val Phe Met Thr Ala Phe Gly Met Thr Ser Phe
245 250 255

Thr Ile Ala Ile Leu Ile Thr Gln Val Leu Gly Tyr Val Leu Ala Leu
260 265 270

Val Gly Leu Cys Leu Cys Ile Met Ala Cys Glu Pro Val His Gly Pro
275 280 285

Leu Leu Ile Ser Gly Leu Gly Ile Ile Ala Leu Ala Glu Leu Leu Gly
290 295 300

Leu Val Tyr Met Lys Phe Val Glu
305 310

<210> SEQ ID NO 57
<211> LENGTH: 321
<212> TYPE: PRT
<213> ORGANISM: Mus musculus

<400> SEQUENCE: 57

Met Trp Pro Leu Ala Ala Ala Leu Leu Leu Gly Ser Cys Cys Cys Gly

```
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Lys Ala Val
    290                 295                 300

Glu Glu Pro Leu Asn Ala Phe Lys Glu Ser Lys Gly Met Met Asn Asp
305                 310                 315                 320

Glu


<210> SEQ ID NO 58
<211> LENGTH: 303
<212> TYPE: PRT
<213> ORGANISM: Mus musculus

<400> SEQUENCE: 58

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
```

```
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Asn Arg
    290                 295                 300
```

<210> SEQ ID NO 59
<211> LENGTH: 5346
<212> TYPE: DNA
<213> ORGANISM: Homo sapiens

<400> SEQUENCE: 59

```
ggggagcagg cgggggagcg ggcgggaagc agtgggagcg cgcgtgcgcg cggccgtgca      60

gcctgggcag tgggtcctgc ctgtgacgcg cggcggcggt cggtcctgcc tgtaacggcg     120

gcggcggctg ctgctccaga cacctgcggc ggcggcggcg accccgcggc gggcgcggag     180

atgtggcccc tggtagcggc gctgttgctg ggctcggcgt gctgcggatc agctcagcta     240

ctatttaata aaacaaaatc tgtagaattc acgttttgta atgacactgt cgtcattcca     300

tgctttgtta ctaatatgga ggcacaaaac actactgaag tatacgtaaa gtggaaattt     360

aaaggaagag atatttacac ctttgatgga gctctaaaca agtccactgt ccccactgac     420

tttagtagtg caaaaattga agtctcacaa ttactaaaag gagatgcctc tttgaagatg     480

gataagagtg atgctgtctc acacacagga aactacactt gtgaagtaac agaattaacc     540

agagaaggtg aaacgatcat cgagctaaaa tatcgtgttg tttcatggtt ttctccaaat     600

gaaaatattc ttattgttat tttcccaatt tttgctatac tcctgttctg gggacagttt     660

ggtattaaaa cacttaaata tagatccggt ggtatggatg agaaaacaat tgctttactt     720
```

```
gttgctggac tagtgatcac tgtcattgtc attgttggag ccattctttt cgtcccaggt    780
gaatattcat taaagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactatacaa   1080
cctcctagga aagctgtaga ggaacccctt aatgcattca aagaatcaaa aggaatgatg   1140
aatgatgaat aactgaagtg aagtgatgga ctccgatttg gagagtagta agacgtgaaa   1200
ggaatacact tgtgtttaag caccatggcc ttgatgattc actgttgggg agaagaaaca   1260
agaaaagtaa ctggttgtca cctatgagac ccttacgtga ttgttagtta agtttttatt   1320
caaagcagct gtaatttagt taataaaata attatgatct atgttgtttg cccaattgag   1380
atccagtttt ttgttgttat ttttaatcaa ttaggggcaa tagtagaatg gacaatttcc   1440
aagaatgatg cctttcaggt cctagggcct ctggcctcta ggtaaccagt ttaaattggt   1500
tcagggtgat aactacttag cactgccctg gtgattaccc agagatatct atgaaaacca   1560
gtggcttcca tcaaaccttt gccaactcag gttcacagca gctttgggca gttatggcag   1620
tatggcatta gctgagaggt gtctgccact tctgggtcaa tggaataata aattaagtac   1680
aggcaggaat ttggttggga gcatcttgta tgatctccgt atgatgtgat attgatggag   1740
atagtggtcc tcattcttgg gggttgccat tcccacattc cccccttcaac aaacagtgta   1800
acaggtcctt cccagattta gggtactttt attgatggat atgttttcct tttattcaca   1860
taaccccttg aaaccctgtc ttgtcctcct gttacttgct tctgctgtac aagatgtagc   1920
accttttctc ctctttgaac atggtctagt gacacggtag caccagttgc aggaaggagc   1980
cagacttgtt ctcagagcac tgtgttcaca cttttcagca aaaatagcta tggttgtaac   2040
atatgtattc ccttcctctg atttgaaggc aaaaatctac agtgtttctt cacttctttt   2100
ctgatctggg gcatgaaaaa agcaagattg aaatttgaac tatgagtctc ctgcatggca   2160
acaaaatgtg tgtcaccatc aggccaacag gccagccctt gaatggggat ttattactgt   2220
tgtatctatg ttgcatgata aacattcatc accttcctcc tgtagtcctg cctcgtactc   2280
cccttcccct atgattgaaa agtaaacaaa acccacattt cctatcctgg ttagaagaaa   2340
attaatgttc tgacagttgt gatcgcctgg agtactttta gacttttagc attcgttttt   2400
tacctgtttg tggatgtgtg tttgtatgtg catacgtatg agataggcac atgcatcttc   2460
tgtatggaca aaggtggggt acctacagga gagcaaaggt taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc   2640
ctgtaaaaat acgtaattct tcctgtttgt gtaataagat attcatattt gtagttgcat   2700
taataatagt tatttcttag tccatcagat gttcccgtgt gcctctttta tgccaaattg   2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
tatgtataca caaatatata cgtatatcta tatatacgta tgtatataca cacatgtata   2940
ttcttccttg attgtgtagc tgtccaaaat aataacatat atagagggag ctgtattcct   3000
ttatacaaat ctgatggctc ctgcagcact ttttccttct gaaaatattt acattttgct   3060
aacctagttt gttactttaa aaatcagttt tgatgaaagg agggaaaagc agatggactt   3120
```

```
gaaaaagatc caagctccta ttagaaaagg tatgaaaatc tttatagtaa aatttttat   3180
aaactaaagt tgtacctttt aatatgtagt aaactctcat ttatttgggg ttcgctcttg   3240
gatctcatcc atccattgtg ttctctttaa tgctgcctgc cttttgaggc attcactgcc   3300
ctagacaatg ccaccagaga tagtggggga aatgccagat gaaaccaact cttgctctca   3360
ctagttgtca gcttctctgg ataagtgacc acagaagcag gagtcctcct gcttgggcat   3420
cattgggcca gttccttctc tttaaatcag atttgtaatg gctcccaaat tccatcacat   3480
cacatttaaa ttgcagacag tgttttgcac atcatgtatc tgttttgtcc cataatatgc   3540
tttttactcc ctgatcccag tttctgctgt tgactcttcc attcagtttt atttattgtg   3600
tgttctcaca gtgacaccat ttgtcctttt ctgcaacaac ctttccagct acttttgcca   3660
aattctattt gtcttctcct tcaaaacatt ctcctttgca gttcctcttc atctgtgtag   3720
ctgctctttt gtctcttaac ttaccattcc tatagtactt tatgcatctc tgcttagttc   3780
tattagtttt ttggccttgc tcttctcctt gattttaaaa ttccttctat agctagagct   3840
tttctttctt tcattctctc ttcctgcagt gttttgcata catcagaagc taggtacata   3900
agttaaatga ttgagagttg gctgtattta gatttatcac tttttaatag ggtgagcttg   3960
agagttttct ttctttctgt tttttttttt tgtttttttt tttttttttt tttttttttt   4020
ttttgactaa tttcacatgc tctaaaaacc ttcaaaggtg attatttttc tcctggaaac   4080
tccaggtcca ttctgtttaa atccctaaga atgtcagaat taaaataaca gggctatccc   4140
gtaattggaa atatttcttt tttcaggatg ctatagtcaa tttagtaagt gaccaccaaa   4200
ttgttatttg cactaacaaa gctcaaaaca cgataagttt actcctccat ctcagtaata   4260
aaaattaagc tgtaatcaac cttctaggtt tctcttgtct taaaatgggt attcaaaaat   4320
ggggatctgt ggtgtatgta tggaaacaca tactccttaa tttacctgtt gttggaaact   4380
ggagaaatga ttgtcgggca accgtttatt ttttattgta ttttatttgg ttgagggatt   4440
tttttataaa cagttttact tgtgtcatat tttaaaatta ctaactgcca tcacctgctg   4500
gggtcctttg ttaggtcatt ttcagtgact aatagggata atccaggtaa ctttgaagag   4560
atgagcagtg agtgaccagg cagtttttct gcctttagct ttgacagttc ttaattaaga   4620
tcattgaaga ccagctttct cataaatttc tctttttgaa aaaaagaaag catttgtact   4680
aagctcctct gtaagacaac atcttaaatc ttaaaagtgt tgttatcatg actggtgaga   4740
gaagaaaaca ttttgttttt attaaatgga gcattattta caaaaagcca ttgttgagaa   4800
ttagatccca catcgtataa atatctatta accattctaa ataaagagaa ctccagtgtt   4860
gctatgtgca agatcctctc ttggagcttt tttgcatagc aattaaaggt gtgctatttg   4920
tcagtagcca ttttttttgca gtgatttgaa gaccaaagtt gttttacagc tgtgttaccg   4980
ttaaaggttt ttttttttat atgtattaaa tcaatttatc actgtttaaa gctttgaata   5040
tctgcaatct ttgccaaggt actttttttat ttaaaaaaaa acataacttt gtaaatatta   5100
ccctgtaata ttatatatac ttaataaaac attttaagct attttgttgg gctatttcta   5160
ttgctgctac agcagaccac aagcacattt ctgaaaaatt taatttatta atgtattttt   5220
aagttgctta tattctaggt aacaatgtaa agaatgattt aaaatattaa ttatgaattt   5280
tttgagtata atacccaata agcttttaat tagagcagag ttttaattaa aagttttaaa   5340
tcagtc                                                              5346
```

<210> SEQ ID NO 60

<211> LENGTH: 5288
<212> TYPE: DNA
<213> ORGANISM: Homo sapiens

<400> SEQUENCE: 60

```
ggggagcagg cgggggagcg ggcgggaagc agtgggagcg cgcgtgcgcg cggccgtgca     60
gcctgggcag tgggtcctgc ctgtgacgcg cggcggcggt cggtcctgcc tgtaacggcg    120
gcggcggctg ctgctccaga cacctgcggc ggcggcggcg accccgcggc gggcgcggag    180
atgtggcccc tggtagcggc gctgttgctg ggctcggcgt gctgcggatc agctcagcta    240
ctatttaata aaacaaaatc tgtagaattc acgttttgta atgacactgt cgtcattcca    300
tgctttgtta ctaatatgga ggcacaaaac actactgaag tatacgtaaa gtggaaattt    360
aaaggaagag atatttacac ctttgatgga gctctaaaca agtccactgt ccccactgac    420
tttagtagtg caaaaattga agtctcacaa ttactaaaag gagatgcctc tttgaagatg    480
gataagagtg atgctgtctc acacacagga aactacactt gtgaagtaac agaattaacc    540
agagaaggtg aaacgatcat cgagctaaaa tatcgtgttg tttcatggtt ttctccaaat    600
gaaaatattc ttattgttat tttcccaatt tttgctatac tcctgttctg gggacagttt    660
ggtattaaaa cacttaaata tagatccggt ggtatggatg agaaaacaat tgctttactt    720
gttgctggac tagtgatcac tgtcattgtc attgttggag ccattctttt cgtcccaggt    780
gaatattcat taaagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactatacaa   1080
cctcctagga ataactgaag tgaagtgatg gactccgatt tggagagtag taagacgtga   1140
aaggaataca cttgtgttta agcaccatgg ccttgatgat tcactgttgg ggagaagaaa   1200
caagaaaagt aactggttgt cacctatgag acccttacgt gattgttagt taagttttta   1260
ttcaaagcag ctgtaattta gttaataaaa taattatgat ctatgttgtt tgcccaattg   1320
agatccagtt ttttgttgtt atttttaatc aattaggggc aatagtagaa tggacaattt   1380
ccaagaatga tgcctttcag gtcctagggc ctctggcctc taggtaacca gtttaaattg   1440
gttcagggtg ataactactt agcactgccc tggtgattac ccagagatat ctatgaaaac   1500
cagtggcttc catcaaacct ttgccaactc aggttcacag cagctttggg cagttatggc   1560
agtatggcat tagctgagag gtgtctgcca cttctgggtc aatggaataa taaattaagt   1620
acaggcagga atttggttgg gagcatcttg tatgatctcc gtatgatgtg atattgatgg   1680
agatagtggt cctcattctt gggggttgcc attcccacat tccccccttca acaaacagtg   1740
taacaggtcc ttcccagatt tagggtactt ttattgatgg atatgttttc cttttattca   1800
cataacccct tgaaaccctg tcttgtcctc ctgttacttg cttctgctgt acaagatgta   1860
gcaccttttc tcctctttga acatggtcta gtgacacggt agcaccagtt gcaggaagga   1920
gccagacttg ttctcagagc actgtgttca cacttttcag caaaaatagc tatggttgta   1980
acatatgtat tcccttcctc tgatttgaag gcaaaaatct acagtgtttc ttcacttctt   2040
ttctgatctg gggcatgaaa aaagcaagat tgaaatttga actatgagtc tcctgcatgg   2100
caacaaaatg tgtgtcacca tcaggccaac aggccagccc ttgaatgggg atttattact   2160
gttgtatcta tgttgcatga taaacattca tcaccttcct cctgtagtcc tgcctcgtac   2220
```

```
tccccttccc ctatgattga aaagtaaaca aaacccacat ttcctatcct ggttagaaga   2280
aaattaatgt tctgacagtt gtgatcgcct ggagtacttt tagactttta gcattcgttt   2340
tttacctgtt tgtggatgtg tgtttgtatg tgcatacgta tgagataggc acatgcatct   2400
tctgtatgga caaaggtggg gtacctacag gagagcaaag gttaattttg tgcttttagt   2460
aaaaacattt aaatacaaag ttctttattg ggtggaatta tatttgatgc aaatatttga   2520
tcacttaaaa cttttaaaac ttctaggtaa tttgccacgc tttttgactg ctcaccaata   2580
ccctgtaaaa atacgtaatt cttcctgttt gtgtaataag atattcatat ttgtagttgc   2640
attaataata gttatttctt agtccatcag atgttcccgt gtgcctcttt tatgccaaat   2700
tgattgtcat atttcatgtt gggaccaagt agtttgccca tggcaaacct aaatttatga   2760
cctgctgagg cctctcagaa aactgagcat actagcaaga cagctcttct tgaaaaaaaa   2820
aatatgtata cacaaatata tacgtatatc tatatatacg tatgtatata cacacatgta   2880
tattcttcct tgattgtgta gctgtccaaa ataataacat atatagaggg agctgtattc   2940
ctttatacaa atctgatggc tcctgcagca ctttttcctt ctgaaaatat ttacattttg   3000
ctaacctagt ttgttacttt aaaaatcagt tttgatgaaa ggagggaaaa gcagatggac   3060
ttgaaaaaga tccaagctcc tattagaaaa ggtatgaaaa tctttatagt aaaatttttt   3120
ataaactaaa gttgtacctt ttaatatgta gtaaactctc atttatttgg ggttcgctct   3180
tggatctcat ccatccattg tgttctcttt aatgctgcct gccttttgag gcattcactg   3240
ccctagacaa tgccaccaga gatagtgggg gaaatgccag atgaaaccaa ctcttgctct   3300
cactagttgt cagcttctct ggataagtga ccacagaagc aggagtcctc ctgcttgggc   3360
atcattgggc cagttccttc tctttaaatc agatttgtaa tggctcccaa attccatcac   3420
atcacattta aattgcagac agtgttttgc acatcatgta tctgttttgt cccataatat   3480
gctttttact ccctgatccc agtttctgct gttgactctt ccattcagtt ttatttattg   3540
tgtgttctca cagtgacacc atttgtcctt ttctgcaaca acctttccag ctacttttgc   3600
caaattctat ttgtcttctc cttcaaaaca ttctcctttg cagttcctct tcatctgtgt   3660
agctgctctt ttgtctctta acttaccatt cctatagtac tttatgcatc tctgcttagt   3720
tctattagtt ttttggcctt gctcttctcc ttgattttaa aattccttct atagctagag   3780
cttttctttc tttcattctc tcttcctgca gtgttttgca tacatcagaa gctaggtaca   3840
taagttaaat gattgagagt tggctgtatt tagatttatc actttttaat agggtgagct   3900
tgagagtttt ctttctttct gttttttttt tttgtttttt tttttttttt tttttttttt   3960
ttttttgact aatttcacat gctctaaaaa ccttcaaagg tgattatttt tctcctggaa   4020
actccaggtc cattctgttt aaatccctaa gaatgtcaga attaaaataa cagggctatc   4080
ccgtaattgg aaatatttct tttttcagga tgctatagtc aatttagtaa gtgaccacca   4140
aattgttatt tgcactaaca aagctcaaaa cacgataagt ttactcctcc atctcagtaa   4200
taaaaattaa gctgtaatca accttctagg tttctcttgt cttaaaatgg gtattcaaaa   4260
atggggatct gtggtgtatg tatggaaaca catactcctt aatttacctg ttgttggaaa   4320
ctggagaaat gattgtcggg caaccgttta ttttttattg tattttattt ggttgaggga   4380
ttttttttata aacagtttta cttgtgtcat attttaaaat tactaactgc catcacctgc   4440
tggggtcctt tgttaggtca ttttcagtga ctaataggga taatccaggt aactttgaag   4500
agatgagcag tgagtgacca ggcagttttt ctgcctttag ctttgacagt tcttaattaa   4560
```

```
gatcattgaa gaccagcttt ctcataaatt tctcttttttg aaaaaaagaa agcatttgta   4620

ctaagctcct ctgtaagaca acatcttaaa tcttaaaagt gttgttatca tgactggtga   4680

gagaagaaaa catttttgttt ttattaaatg gagcattatt tacaaaaagc cattgttgag   4740

aattagatcc cacatcgtat aaatatctat taaccattct aaataaagag aactccagtg   4800

ttgctatgtg caagatcctc tcttggagct tttttgcata gcaattaaag gtgtgctatt   4860

tgtcagtagc catttttttg cagtgatttg aagaccaaag ttgttttaca gctgtgttac   4920

cgttaaaggt ttttttttt atatgtatta aatcaattta tcactgttta aagctttgaa   4980

tatctgcaat ctttgccaag gtactttttt atttaaaaaa aaacataact ttgtaaatat   5040

taccctgtaa tattatatat acttaataaa acattttaag ctattttgtt gggctatttc   5100

tattgctgct acagcagacc acaagcacat ttctgaaaaa tttaatttat taatgtattt   5160

ttaagttgct tatattctag gtaacaatgt aaagaatgat ttaaaatatt aattatgaat   5220

tttttgagta taatacccaa taagctttta attagagcag agttttaatt aaaagtttta   5280

aatcagtc                                                            5288
```

<210> SEQ ID NO 61
<211> LENGTH: 5021
<212> TYPE: DNA
<213> ORGANISM: Homo sapiens

<400> SEQUENCE: 61

```
agtgggagcg cgcgtgcgcg cggccgtgca gcctgggcag tgggtcctgc ctgtgacgcg     60

cggcggcggt cggtcctgcc tgtaacggcg gcggcggctg ctgctccgga cacctgcggc    120

ggcggcggcg accccgcggc gggcgcggag atgtggcccc tggtagcggc gctgttgctg    180

ggctcggcgt gctgcggatc agctcagcta ctatttaata aaacaaaatc tgtagaattc    240

acgttttgta atgacactgt cgtcattcca tgctttgtta ctaatatgga ggcacaaaac    300

actactgaag tatacgtaaa gtggaaattt aaaggaagag atatttacac ctttgatgga    360

gctctaaaca agtccactgt ccccactgac tttagtagtg caaaaattga agtctcacaa    420

ttactaaaag gagatgcctc tttgaagatg gataagagtg atgctgtctc acacacagga    480

aactacactt gtgaagtaac agaattaacc agagaaggtg aaacgatcat cgagctaaaa    540

tatcgtgttg tttcatggtt ttctccaaat gaaaatattc ttattgttat tttcccaatt    600

tttgctatac tcctgttctg ggacagtttt ggtattaaaa cacttaaata tagatccggt    660

ggtatggatg agaaaacaat tgctttactt gttgctggac tagtgatcac tgtcattgtc    720

attgttggag ccattctttt cgtcccaggt gaatattcat taaagaatgc tactggcctt    780

ggtttaattg tgacttctac agggatatta atattacttc actactatgt gtttagtaca    840

gcgattggat taacctcctt cgtcattgcc atattggtta ttcaggtgat agcctatatc    900

ctcgctgtgg ttggactgag tctctgtatt gcggcgtgta taccaatgca tggccctctt    960

ctgatttcag gtttgagtat cttagctcta gcacaattac ttggactagt ttatatgaaa   1020

tttgtggaat aactgaagtg aagtgatgga ctccgatttg gagagtagta agacgtgaaa   1080

ggaatacact tgtgtttaag caccatggcc ttgatgattc actgttgggg agaagaaaca   1140

agaaaagtaa ctggttgtca cctatgagac ccttacgtga ttgttagtta agtttttatt   1200

caaagcagct gtaatttagt taataaaata attatgatct atgttgtttg cccaattgag   1260

atccagtttt ttgttgttat ttttaatcaa ttaggggcaa tagtagaatg gacaatttcc   1320

aagaatgatg cctttcaggt cctagggcct ctggcctcta ggtaaccagt ttaaattggt   1380
```

```
tcagggtgat aactacttag cactgccctg gtgattaccc agagatatct atgaaaacca   1440
gtggcttcca tcaaaccttt gccaactcag gttcacagca gctttgggca gttatggcag   1500
tatggcatta gctgagaggt gtctgccact tctgggtcaa tggaataata aattaagtac   1560
aggcaggaat ttggttggga gcatcttgta tgatctccgt atgatgtgat attgatggag   1620
atagtggtcc tcattcttgg gggttgccat tcccacattc ccccttcaac aaacagtgta   1680
acaggtcctt cccagattta gggtactttt attgatggat atgttttcct tttattcaca   1740
taacccccttg aaaccctgtc ttgtcctcct gttacttgct tctgctgtac aagatgtagc   1800
accttttctc ctctttgaac atggtctagt gacacggtag caccagttgc aggaaggagc   1860
cagacttgtt ctcagagcac tgtgttcaca cttttcagca aaaatagcta tggttgtaac   1920
atatgtattc ccttcctctg atttgaaggc aaaaatctac agtgtttctt cacttctttt   1980
ctgatctggg gcatgaaaaa agcaagattg aaatttgaac tatgagtctc ctgcatggca   2040
acaaaatgtg tgtcaccatc aggccaacag gccagccctt gaatggggat ttattactgt   2100
tgtatctatg ttgcatgata aacattcatc accttcctcc tgtagtcctg cctcgtactc   2160
cccttcccct atgattgaaa agtaaacaaa acccacattt cctatcctgg ttagaagaaa   2220
attaatgttc tgacagttgt gatcgcctgg agtactttta gacttttagc attcgttttt   2280
tacctgtttg tggatgtgtg tttgtatgtg catacgtatg agataggcac atgcatcttc   2340
tgtatggaca aaggtggggt acctacagga gagcaaaggt taattttgtg cttttagtaa   2400
aaacatttaa atacaaagtt ctttattggg tggaattata tttgatgcaa atatttgatc   2460
acttaaaact tttaaaactt ctaggtaatt tgccacgctt tttgactgct caccaatacc   2520
ctgtaaaaat acgtaattct tcctgtttgt gtaataagat attcatattt gtagttgcat   2580
taataatagt tatttcttag tccatcagat gttcccgtgt gcctctttta tgccaaattg   2640
attgtcatat ttcatgttgg gaccaagtag tttgcccatg gcaaacctaa atttatgacc   2700
tgctgaggcc tctcagaaaa ctgagcatac tagcaagaca gctcttcttg aaaaaaaaaa   2760
tatgtataca caaatatata cgtatatcta tatatacgta tgtatataca cacatgtata   2820
ttcttccttg attgtgtagc tgtccaaaat aataacatat atagagggag ctgtattcct   2880
ttatacaaat ctgatggctc ctgcagcact ttttccttct gaaaatattt acattttgct   2940
aacctagttt gttactttaa aaatcagttt tgatgaaagg agggaaaagc agatggactt   3000
gaaaaagatc caagctccta ttagaaaagg tatgaaaatc tttatagtaa aatttttttat   3060
aaactaaagt tgtacctttt aatatgtagt aaactctcat ttatttgggg ttcgctcttg   3120
gatctcatcc atccattgtg ttctctttaa tgctgcctgc cttttgaggc attcactgcc   3180
ctagacaatg ccaccagaga tagtggggga aatgccagat gaaaccaact cttgctctca   3240
ctagttgtca gcttctctgg ataagtgacc acagaagcag gagtcctcct gcttgggcat   3300
cattgggcca gttccttctc tttaaatcag atttgtaatg gctcccaaat tccatcacat   3360
cacatttaaa ttgcagacag tgttttgcac atcatgtatc tgttttgtcc cataaatatgc   3420
tttttactcc ctgatcccag tttctgctgt tgactcttcc attcagtttt atttattgtg   3480
tgttctcaca gtgacaccat ttgtcctttt ctgcaacaac ctttccagct acttttgcca   3540
aattctattt gtcttctcct tcaaaacatt ctcctttgca gttcctcttc atctgtgtag   3600
ctgctctttt gtctcttaac ttaccattcc tatagtactt tatgcatctc tgcttagttc   3660
tattagtttt ttggccttgc tcttctcctt gattttaaaa ttccttctat agctagagct   3720
```

```
tttctttctt tcattctctc ttcctgcagt gttttgcata catcagaagc taggtacata   3780
agttaaatga ttgagagttg gctgtattta gatttatcac tttttaatag ggtgagcttg   3840
agagttttct ttctttctgt ttttttttt tgttttttt ttttttttt ttttttttt   3900
ttttgactaa tttcacatgc tctaaaaacc ttcaaaggtg attatttttc tcctggaaac   3960
tccaggtcca ttctgtttaa atccctaaga atgtcagaat taaaataaca gggctatccc   4020
gtaattggaa atatttcttt tttcaggatg ctatagtcaa tttagtaagt gaccaccaaa   4080
ttgttatttg cactaacaaa gctcaaaaca cgataagttt actcctccat ctcagtaata   4140
aaaattaagc tgtaatcaac cttctaggtt tctcttgtct taaaatgggt attcaaaaat   4200
ggggatctgt ggtgtatgta tggaaacaca tactccttaa tttacctgtt gttggaaact   4260
ggagaaatga ttgtcgggca accgtttatt ttttattgta ttttatttgg ttgagggatt   4320
tttttataaa cagttttact tgtgtcatat tttaaaatta ctaactgcca tcacctgctg   4380
gggtcctttg ttaggtcatt ttcagtgact aatagggata atccaggtaa ctttgaagag   4440
atgagcagtg agtgaccagg cagtttttct gcctttagct ttgacagttc ttaattaaga   4500
tcattgaaga ccagctttct cataaatttc tctttttgaa aaaaagaaag catttgtact   4560
aagctcctct gtaagacaac atcttaaatc ttaaaagtgt tgttatcatg actggtgaga   4620
gaagaaaaca ttttgttttt attaaatgga gcattattta caaaaagcca ttgttgagaa   4680
ttagatccca catcgtataa atatctatta accattctaa ataaagagaa ctccagtgtt   4740
gctatgtgca agatcctctc ttggagcttt tttgcatagc aattaaaggt gtgctatttg   4800
tcagtagcca tttttttgca gtgatttgaa gaccaaagtt gttttacagc tgtgttaccg   4860
ttaaaggttt tttttttat atgtattaaa tcaatttatc actgtttaaa gctttgaata   4920
tctgcaatct ttgccaaggt actttttat ttaaaaaaaa acataacttt gtaaatatta   4980
ccctgtaata ttatatatac ttaataaaac attttaagct a                       5021
```

<210> SEQ ID NO 62
<211> LENGTH: 5078
<212> TYPE: DNA
<213> ORGANISM: Homo sapiens

<400> SEQUENCE: 62

```
agtgggagcg cgcgtgcgcg cggccgtgca gcctgggcag tgggtcctgc ctgtgacgcg     60
cggcggcggt cggtcctgcc tgtaacggcg gcggcggctg ctgctccgga cacctgcggc    120
ggcggcggcg accccgcggc gggcgcggag atgtggcccc tggtagcggc gctgttgctg    180
ggctcggcgt gctgcggatc agctcagcta ctatttaata aaacaaaatc tgtagaattc    240
acgttttgta atgacactgt cgtcattcca tgctttgtta ctaatatgga ggcacaaaac    300
actactgaag tatacgtaaa gtggaaattt aaaggaagag atatttacac ctttgatgga    360
gctctaaaca agtccactgt ccccactgac tttagtagtg caaaaattga agtctcacaa    420
ttactaaaag gagatgcctc tttgaagatg gataagagtg atgctgtctc acacacagga    480
aactacactt gtgaagtaac agaattaacc agagaaggtg aaacgatcat cgagctaaaa    540
tatcgtgttg tttcatggtt ttctccaaat gaaaatattc ttattgttat tttcccaatt    600
tttgctatac tcctgttctg ggacagtttt ggtattaaaa cacttaaata tagatccggt    660
ggtatggatg agaaaacaat tgctttactt gttgctggac tagtgatcac tgtcattgtc    720
attgttggag ccattctttt cgtcccaggt gaatattcat taaagaatgc tactggcctt    780
ggtttaattg tgacttctac agggatatta atattacttc actactatgt gtttagtaca    840
```

```
gcgattggat taacctcctt cgtcattgcc atattggtta ttcaggtgat agcctatatc    900
ctcgctgtgg ttggactgag tctctgtatt gcggcgtgta taccaatgca tggccctctt    960
ctgatttcag gtttgagtat cttagctcta gcacaattac ttggactagt ttatatgaaa   1020
tttgtggctt ccaatcagaa gactatacaa cctcctagga aagctgtaga ggaacccctt   1080
aatgaataac tgaagtgaag tgatggactc cgatttggag agtagtaaga cgtgaaagga   1140
atacacttgt gtttaagcac catggccttg atgattcact gttggggaga agaaacaaga   1200
aaagtaactg gttgtcacct atgagaccct tacgtgattg ttagttaagt ttttattcaa   1260
agcagctgta atttagttaa taaaataatt atgatctatg ttgtttgccc aattgagatc   1320
cagtttttg ttgttatttt taatcaatta ggggcaatag tagaatggac aatttccaag    1380
aatgatgcct ttcaggtcct agggcctctg gcctctaggt aaccagttta aattggttca   1440
gggtgataac tacttagcac tgccctggtg attacccaga gatatctatg aaaaccagtg   1500
gcttccatca aacctttgcc aactcaggtt cacagcagct ttgggcagtt atggcagtat   1560
ggcattagct gagaggtgtc tgccacttct gggtcaatgg aataataaat taagtacagg   1620
caggaatttg gttgggagca tcttgtatga tctccgtatg atgtgatatt gatggagata   1680
gtggtcctca ttcttggggg ttgccattcc cacattcccc cttcaacaaa cagtgtaaca   1740
ggtccttccc agatttaggg tacttttatt gatggatatg ttttcctttt attcacataa   1800
cccctgaaa ccctgtcttg tcctcctgtt acttgcttct gctgtacaag atgtagcacc    1860
ttttctcctc tttgaacatg gtctagtgac acggtagcac cagttgcagg aaggagccag   1920
acttgttctc agagcactgt gttcacactt ttcagcaaaa atagctatgg ttgtaacata   1980
tgtattccct tcctctgatt tgaaggcaaa aatctacagt gtttcttcac ttcttttctg   2040
atctggggca tgaaaaaagc aagattgaaa tttgaactat gagtctcctg catggcaaca   2100
aaatgtgtgt caccatcagg ccaacaggcc agcccttgaa tggggattta ttactgttgt   2160
atctatgttg catgataaac attcatcacc ttcctcctgt agtcctgcct cgtactcccc   2220
ttcccctatg attgaaaagt aaacaaaacc cacatttcct atcctggtta gaagaaaatt   2280
aatgttctga cagttgtgat cgcctggagt acttttagac ttttagcatt cgtttttac    2340
ctgtttgtgg atgtgtgttt gtatgtgcat acgtatgaga taggcacatg catcttctgt   2400
atggacaaag gtggggtacc tacaggagag caaaggttaa ttttgtgctt ttagtaaaaa   2460
catttaaata caaagttctt tattgggtgg aattatattt gatgcaaata tttgatcact   2520
taaaactttt aaaacttcta ggtaatttgc cacgcttttt gactgctcac caataccctg   2580
taaaaatacg taattcttcc tgtttgtgta ataagatatt catatttgta gttgcattaa   2640
taatagttat ttcttagtcc atcagatgtt cccgtgtgcc tcttttatgc caaattgatt   2700
gtcatatttc atgttgggac caagtagttt gcccatggca aacctaaatt tatgacctgc   2760
tgaggcctct cagaaaactg agcatactag caagacagct cttcttgaaa aaaaaaatat   2820
gtatacacaa atatatacgt atatctatat atacgtatgt atatacacac atgtatattc   2880
ttccttgatt gtgtagctgt ccaaaataat aacatatata gagggagctg tattccttta   2940
tacaaatctg atggctcctg cagcactttt tccttctgaa aatatttaca ttttgctaac   3000
ctagtttgtt actttaaaaa tcagttttga tgaaaggagg gaaaagcaga tggacttgaa   3060
aaagatccaa gctcctatta gaaaaggtat gaaaatcttt atagtaaaat tttttataaa   3120
ctaaagttgt accttttaat atgtagtaaa ctctcattta tttggggttc gctcttggat   3180
```

```
ctcatccatc cattgtgttc tctttaatgc tgcctgcctt ttgaggcatt cactgcccta   3240

gacaatgcca ccagagatag tgggggaaat gccagatgaa accaactctt gctctcacta   3300

gttgtcagct tctctggata agtgaccaca gaagcaggag tcctcctgct tgggcatcat   3360

tgggccagtt ccttctcttt aaatcagatt tgtaatggct cccaaattcc atcacatcac   3420

atttaaattg cagacagtgt tttgcacatc atgtatctgt tttgtcccat aatatgcttt   3480

ttactccctg atcccagttt ctgctgttga ctcttccatt cagttttatt tattgtgtgt   3540

tctcacagtg acaccatttg tccttttctg caacaacctt tccagctact tttgccaaat   3600

tctatttgtc ttctccttca aaacattctc ctttgcagtt cctcttcatc tgtgtagctg   3660

ctcttttgtc tcttaactta ccattcctat agtactttat gcatctctgc ttagttctat   3720

tagtttttg gccttgctct tctccttgat tttaaaattc cttctatagc tagagctttt   3780

ctttctttca ttctctcttc ctgcagtgtt ttgcatacat cagaagctag gtacataagt   3840

taaatgattg agagttggct gtatttagat ttatcacttt ttaatagggt gagcttgaga   3900

gtttcttttc tttctgtttt tttttttgt ttttttttt ttttttttt ttttttttt   3960

tgactaattt cacatgctct aaaaaccttc aaaggtgatt atttttctcc tggaaactcc   4020

aggtccattc tgtttaaatc cctaagaatg tcagaattaa aataacaggg ctatcccgta   4080

attggaaata tttcttttt caggatgcta tagtcaattt agtaagtgac caccaaattg   4140

ttatttgcac taacaaagct caaaacacga taagtttact cctccatctc agtaataaaa   4200

attaagctgt aatcaacctt ctaggtttct cttgtcttaa aatgggtatt caaaaatggg   4260

gatctgtggt gtatgtatgg aaacacatac tccttaattt acctgttgtt ggaaactgga   4320

gaaatgattg tcgggcaacc gtttattttt tattgtattt tatttggttg agggattttt   4380

ttataaacag ttttacttgt gtcatatttt aaaattacta actgccatca cctgctgggg   4440

tcctttgtta ggtcattttc agtgactaat agggataatc caggtaactt tgaagagatg   4500

agcagtgagt gaccaggcag tttttctgcc tttagctttg acagttctta attaagatca   4560

ttgaagacca gctttctcat aaatttctct ttttgaaaaa aagaaagcat ttgtactaag   4620

ctcctctgta agacaacatc ttaaatctta aaagtgttgt tatcatgact ggtgagagaa   4680

gaaaacattt tgtttttatt aaatggagca ttatttacaa aaagccattg ttgagaatta   4740

gatcccacat cgtataaata tctattaacc attctaaata aagagaactc cagtgttgct   4800

atgtgcaaga tcctctcttg gagctttttt gcatagcaat taaaggtgtg ctatttgtca   4860

gtagccattt ttttgcagtg atttgaagac caaagttgtt ttacagctgt gttaccgtta   4920

aaggtttttt tttttatatg tattaaatca atttatcact gtttaaagct ttgaatatct   4980

gcaatctttg ccaaggtact tttttattta aaaaaaaaca taactttgta aatattaccc   5040

tgtaatatta tatatactta ataaaacatt ttaagcta                         5078
```

```
<210> SEQ ID NO 63
<211> LENGTH: 323
<212> TYPE: PRT
<213> ORGANISM: Homo sapiens

<400> SEQUENCE: 63

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
```

```
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu


<210> SEQ ID NO 64
<211> LENGTH: 305
<212> TYPE: PRT
<213> ORGANISM: Homo sapiens

<400> SEQUENCE: 64

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
```

```
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305


<210> SEQ ID NO 65
<211> LENGTH: 293
<212> TYPE: PRT
<213> ORGANISM: Homo sapiens

<400> SEQUENCE: 65

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140
```

```
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290


<210> SEQ ID NO 66
<211> LENGTH: 312
<212> TYPE: PRT
<213> ORGANISM: Homo sapiens

<400> SEQUENCE: 66

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220
```

```
Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Glu
305                 310


<210> SEQ ID NO 67
<211> LENGTH: 1934
<212> TYPE: DNA
<213> ORGANISM: Artificial
<220> FEATURE:
<223> OTHER INFORMATION: Homo sapiens and Mus musculus

<400> SEQUENCE: 67

cccgggcagc ctgggcggcc gctcctgcct gtcactgctg cggcgctgct ggtcggtcgt     60

ttcccttgaa ggcagcagcg gaggcggcgg ctgctccaga cacctgcggc ggcgaccccc    120

cggcggcgcg gagatgtggc ccttggcggc ggcgctgttg ctgggctcct gctgctgcgg    180

ttcagctcaa ctactgttta ataaaacaaa atctgtagaa ttcacgtttt gtaatgacac    240

tgtcgtcatt ccatgctttg ttactaatat ggaggcacaa aacactactg aagtatacgt    300

aaagtggaaa tttaaaggaa gagatatcta cacctttgat ggagctctaa acaagtccac    360

tgtccccact gactttagta gtgcaaaaat tgaagtctca caattactaa aaggagatgc    420

ctctttgaag atggataaga gtgatgctgt ctcacacaca ggaaactaca cttgtgaagt    480

aacagaatta accagagaag gtgaaacgat catagagctg aaaaaccgca cggccttcaa    540

cactgaccaa ggatcagcct gttcttacga ggaggagaaa ggaggttgca aattagtttc    600

gtggttttct ccaaatgaaa agatcctcat tgttattttc ccaattttgg ctatactcct    660

gttctgggga aagtttggta ttttaacact caaatataaa tccagccata cgaataagag    720

aatcattctg ctgctcgttg ccgggctggt gctcacagtc atcgtggttg ttggagccat    780

ccttctcatc ccaggagaaa agcccgtgaa gaatgcttct ggacttggcc tcattgtaat    840

ctctacgggg atattaatac tacttcagta caatgtgttt atgacagctt ttggaatgac    900

ctctttcacc attgccatat tgatcactca agtgctgggc tacgtccttg ctttggtcgg    960

gctgtgtctc tgcatcatgg catgtgagcc agtgcacggc cccctttttga tttcaggttt   1020

ggggatcata gctctagcag aactacttgg attagtttat atgaagtttg tcgcttccaa   1080

ccagaggact atccaacctc ctaggaatag gtgaagggaa gtgacggact gtaacttgga   1140

agtcagaaat ggaagaatac agttgtctaa gcaccaggtc ttcacgactc acagctggaa   1200

ggaacagaca acagtaactg acttccatcc aggaaaacat gtcacataaa tgattactaa   1260

gtttatattc aaagcagctg tactttacat aataaaaaaa atatgatgtg ctgtgtaacc   1320

aattggaatc ccattttttct attgtttcta ctcaactagg ggcaaacgtt tcaggggcaa   1380

cttccaagaa tgatgcttgt tagatcctag agtctctgaa cactgagttt aaattgattc   1440

cgagtgagac tcgccaagca ctaacctgag ggttagttac ccagagatac ctatgaaaaa   1500
```

```
cagtggtatc cagcaagcct tagtaaactc aggttgccag cagctttgcc acttccgctg   1560
ctagctgaat aacaagactg ccacttctgg gtcatagtga tagagactga agtagaaaaa   1620
cgaatgtggt tgggcaaatc ccgtgtggcc cctctgtgtg ctatgatatt gatggcactg   1680
gtgtcttcat tcttgggggt tgccatcatt cacacacacc cctttgacat acagtgcacc   1740
ccagttttga atacattttt tttgcaccct gtcccgttct gctactttga tttgcgttat   1800
gatatatata tatatatata atacctttc tcctctttaa acatggtcct gtgacacaat   1860
agtcagttgc agaaaggagc cagacttatt cgcaaagcac tgtgctcaaa ctcttcagaa   1920
aaaaaaaaaa aaaa                                                     1934
```

<210> SEQ ID NO 68
<211> LENGTH: 3107
<212> TYPE: DNA
<213> ORGANISM: Artificial
<220> FEATURE:
<223> OTHER INFORMATION: Homo sapiens and Mus musculus

<400> SEQUENCE: 68

```
tggtgaaagc agaagcagcg cctacaccgg gagagcaggg aggaggagtt ggactgaggt     60
tgggcggctc cgaggtccag ggcgagcttg gccagaggga gtagagagca gcggggctgc    120
gcagggacgc gtgccgtgag ttccggtgag cgtgtgtgtc ccatgctccc gtctttcagg    180
ccggcccagg acacgaagcc ggaagagagc tggctggagg gacgggggcc gtgagcagag    240
agtgcaaccc gcgcagcccc ggggacaggc tgattcttgg cgctctccgc cggagcctgc    300
ccagggctgg gtgtgaggct ggcgtcacgt caacgagcag aggcggccag gcggggcgga    360
gtgcgcgtgc gcggggcggc gagcacgcgc gcgcgcgcac ccccgggcag cctgggcggc    420
cgctcctgcc tgtcactgct gcggcgctgc tggtcggtcg tttcccttga aggcagcagc    480
ggaggcggcg gctgctccag acacctgcgg cggcgacccc ccggcggcgc ggagatgtgg    540
cccttggcgg cggcgctgtt gctgggctcc tgctgctgcg gttcagctca actactgttt    600
aataaaacaa aatctgtaga attcacgttt tgtaatgaca ctgtcgtcat tccatgcttt    660
gttactaata tggaggcaca aaacactact gaagtatacg taaagtggaa atttaaagga    720
agagatatct acacctttga tggagctcta aacaagtcca ctgtccccac tgactttagt    780
agtgcaaaaa ttgaagtctc acaattacta aaaggagatg cctctttgaa gatggataag    840
agtgatgctg tctcacacac aggaaactac acttgtgaag taacagaatt aaccagagaa    900
ggtgaaacga tcatagagct gaaaaaccgc acggccttca acactgacca aggatcagcc    960
tgttcttacg aggaggagaa aggaggttgc aaattagttt cgtggttttc tccaaatgaa   1020
aagatcctca ttgttatttt cccaattttg gctatactcc tgttctgggg aaagtttggt   1080
attttaacac tcaaatataa atccagccat acgaataaga gaatcattct gctgctcgtt   1140
gccgggctgg tgctcacagt catcgtggtt gttggagcca tccttctcat cccaggagaa   1200
aagcccgtga agaatgcttc tggacttggc ctcattgtaa tctctacggg gatattaata   1260
ctacttcagt acaatgtgtt tatgacagct tttggaatga cctctttcac cattgccata   1320
ttgatcactc aagtgctggg ctacgtcctt gctttggtcg ggctgtgtct ctgcatcatg   1380
gcatgtgagc cagtgcacgg cccccttttg atttcaggtt tggggatcat agctctagca   1440
gaactacttg gattagttta tatgaagttt gtcgagtgga gagagacacc ttcggtcagt   1500
tgagaggcaa gaaggaaagc ttccaaccag aggactatcc aacctcctag gaataggtga   1560
agggaagtga cggactgtaa cttggaagtc agaaatggaa gaatacagtt gtctaagcac   1620
```

```
caggtcttca cgactcacag ctggaaggaa cagacaacag taactgactt ccatccagga   1680

aaacatgtca cataaatgat tactaagttt atattcaaag cagctgtact ttacataata   1740

aaaaaaatat gatgtgctgt gtaaccaatt ggaatcccat ttttctattg tttctactca   1800

actaggggca aacgtttcag gggcaacttc caagaatgat gcttgttaga tcctagagtc   1860

tctgaacact gagtttaaat tgattccgag tgagactcgc caagcactaa cctgagggtt   1920

agttacccag agatacctat gaaaaacagt ggtatccagc aagccttagt aaactcaggt   1980

tgccagcagc tttgccactt ccgctgctag ctgaataaca agactgccac ttctgggtca   2040

tagtgataga gactgaagta gaaaaacgaa tgtggttggg caaatcccgt gtggcccctc   2100

tgtgtgctat gatattgatg gcactggtgt cttcattctt gggggttgcc atcattcaca   2160

cacacccctt tgacatacag tgcaccccag ttttgaatac atttttttg caccctgtcc    2220

cgttctgcta ctttgatttg cgttatgata tatatatata tatataatac cttttctcct   2280

ctttaaacat ggtcctgtga cacaatagtc agttgcagaa aggagccaga cttattcgca   2340

aagcactgtg ctcaaactct tcagaaaaaa aggaaaaaaa aaaaaagcta tagttgtaac   2400

atatgtattc cagacctctg gtttaaaggc aaaagaaaaa aaatctacag tgtttcttct   2460

catgttttct gatcggaggc atgacaaagc aagactgaaa tctgaactgt gtctcctgca   2520

tggcaacacg tgtctccgtc aggccctcgc aaggcccggg gagggggttc tacgcctctt   2580

gtctctttgt tgcatgctga acactcatcg ccttcctact gtatcctgcc tcctgcagcc   2640

tccctcttcc tcctcctctt cctcttcctc ctcttcctcc tcctcctcct cttcctccaa   2700

gtttgaaagg tcaaacaaaa ctaccacatt ccctacccag ttagaagaaa accaccgtcc   2760

tgacagttgt gatcgcatgg agtactttta gattattagc acctgttttt acctcgtttg   2820

tgggcgtgtt tgtatgtgca catgtatgaa gtcggcacat gcaccttctg tatgggcaga   2880

ggcgtggcat ctacagaaga gcagatgcca actttgtgct tttagtgaat acattaaaaa   2940

aaaaaaacca acggtcctta ttgagtggaa ttctatttga tgcaaatatt tgagctcttt   3000

aagactttaa aactagataa tgtgccaagc ttttaggact gctcaccagt gccctctgaa   3060

gaaacaccag tactttttcc tgtttgtgta ataaaggcat atttgta                 3107
```

<210> SEQ ID NO 69
<211> LENGTH: 3120
<212> TYPE: DNA
<213> ORGANISM: Artificial
<220> FEATURE:
<223> OTHER INFORMATION: Homo sapiens and Mus musculus

<400> SEQUENCE: 69

```
tggtgaaagc agaagcagcg cctacaccgg gagagcaggg aggaggagtt ggactgaggt     60

tgggcggctc cgaggtccag ggcgagcttg gccagaggga gtagagagca gcggggctgc    120

gcagggacgc gtgccgtgag ttccggtgag cgtgtgtgtc ccatgctccc gtctttcagg    180

ccggcccagg acacgaagcc ggaagagagc tggctggagg gacgggggcc gtgagcagag    240

agtgcaaccc gcgcagcccc ggggacaggc tgattcttgg cgctctccgc cggagcctgc    300

ccagggctgg gtgtgaggct ggcgtcacgt caacgagcag aggcggccag gcggggcgga    360

gtgcgcgtgc gcggggcggc gagcacgcgc gcgcgcgcac ccccgggcag cctgggcggc    420

cgctcctgcc tgtcactgct gcggcgctgc tggtcggtcg tttcccttga aggcagcagc    480

ggaggcggcg gctgctccag acacctgcgg cggcgacccc ccggcggcgc ggagatgtgg    540
```

```
ccccttggcgg cggcgctgtt gctgggctcc tgctgctgcg gttcagctca actactgttt    600
aataaaacaa aatctgtaga attcacgttt tgtaatgaca ctgtcgtcat tccatgcttt    660
gttactaata tggaggcaca aaacactact gaagtatacg taaagtggaa atttaaagga    720
agagatatct acacctttga tggagctcta aacaagtcca ctgtccccac tgactttagt    780
agtgcaaaaa ttgaagtctc acaattacta aaaggagatg cctctttgaa gatggataag    840
agtgatgctg tctcacacac aggaaactac acttgtgaag taacagaatt aaccagagaa    900
ggtgaaacga tcatagagct gaaaaaccgc acggccttca acactgacca aggatcagcc    960
tgttcttacg aggaggagaa aggaggttgc aaattagttt cgtggttttc tccaaatgaa   1020
aagatcctca ttgttatttt cccaattttg gctatactcc tgttctgggg aaagtttggt   1080
attttaacac tcaaatataa atccagccat acgaataaga gaatcattct gctgctcgtt   1140
gccgggctgg tgctcacagt catcgtggtt gttggagcca tccttctcat cccaggagaa   1200
aagcccgtga agaatgcttc tggacttggc ctcattgtaa tctctacggg gatattaata   1260
ctacttcagt acaatgtgtt tatgacagct tttggaatga cctctttcac cattgccata   1320
ttgatcactc aagtgctggg ctacgtcctt gctttggtcg ggctgtgtct ctgcatcatg   1380
gcatgtgagc cagtgcacgg cccccttttg atttcaggtt tggggatcat agctctagca   1440
gaactacttg gattagttta tatgaagttt gtcgcttcca accagaggac tatccaacct   1500
cctaggaaag ctgtagagga acccccttaac gcatttaaag agtcaaaagg aatgatgaat   1560
gacgaatagg tgaagggaag tgacggactg taacttggaa gtcagaaatg gaagaataca   1620
gttgtctaag caccaggtct tcacgactca cagctggaag gaacagacaa cagtaactga   1680
cttccatcca ggaaaacatg tcacataaat gattactaag tttatattca aagcagctgt   1740
actttacata ataaaaaaaa tatgatgtgc tgtgtaacca attggaatcc catttttcta   1800
ttgtttctac tcaactaggg gcaaacgttt caggggcaac ttccaagaat gatgcttgtt   1860
agatcctaga gtctctgaac actgagttta aattgattcc gagtgagact cgccaagcac   1920
taacctgagg gttagttacc cagagatacc tatgaaaaac agtggtatcc agcaagcctt   1980
agtaaactca ggttgccagc agctttgcca cttccgctgc tagctgaata acaagactgc   2040
cacttctggg tcatagtgat agagactgaa gtagaaaaac gaatgtggtt gggcaaatcc   2100
cgtgtggccc ctctgtgtgc tatgatattg atggcactgg tgtcttcatt cttgggggtt   2160
gccatcattc acacacaccc ctttgacata cagtgcaccc cagttttgaa tacatttttt   2220
ttgcaccctg tcccgttctg ctactttgat ttgcgttatg atatatatat atatatataa   2280
taccttttct cctctttaaa catggtcctg tgacacaata gtcagttgca gaaaggagcc   2340
agacttattc gcaaagcact gtgctcaaac tcttcagaaa aaaaggaaaa aaaaaaaaag   2400
ctatagttgt aacatatgta ttccagacct ctggtttaaa ggcaaaagaa aaaaaatcta   2460
cagtgtttct tctcatgttt tctgatcgga ggcatgacaa agcaagactg aaatctgaac   2520
tgtgtctcct gcatggcaac acgtgtctcc gtcaggccct cgcaaggccc ggggaggggg   2580
ttctacgcct cttgtctctt tgttgcatgc tgaacactca tcgccttcct actgtatcct   2640
gcctcctgca gcctccctct tcctcctcct cttcctcttc ctcctcttcc tcctcctcct   2700
cctcttcctc caagtttgaa aggtcaaaca aaactaccac attccctacc cagttagaag   2760
aaaaccaccg tcctgacagt tgtgatcgca tggagtactt ttagattatt agcacctgtt   2820
tttacctcgt ttgtgggcgt gtttgtatgt gcacatgtat gaagtcggca catgcacctt   2880
ctgtatgggc agaggcgtgg catctacaga agagcagatg ccaactttgt gcttttagtg   2940
```

```
aatacattaa aaaaaaaaaa ccaacggtcc ttattgagtg gaattctatt tgatgcaaat   3000

atttgagctc tttaagactt taaaactaga taatgtgcca agcttttagg actgctcacc   3060

agtgccctct gaagaaacac cagtactttt tcctgtttgt gtaataaagg catatttgta   3120


<210> SEQ ID NO 70
<211> LENGTH: 3087
<212> TYPE: DNA
<213> ORGANISM: Artificial
<220> FEATURE:
<223> OTHER INFORMATION: Homo sapiens and Mus musculus

<400> SEQUENCE: 70

tggtgaaagc agaagcagcg cctacaccgg gagagcaggg aggaggagtt ggactgaggt     60

tgggcggctc cgaggtccag ggcgagcttg gccagaggga gtagagagca gcggggctgc    120

gcagggacgc gtgccgtgag ttccggtgag cgtgtgtgtc ccatgctccc gtctttcagg    180

ccggcccagg acacgaagcc ggaagagagc tggctggagg gacgggggcc gtgagcagag    240

agtgcaaccc gcgcagcccc ggggacaggc tgattcttgg cgctctccgc cggagcctgc    300

ccagggctgg gtgtgaggct ggcgtcacgt caacgagcag aggcggccag gcggggcgga    360

gtgcgcgtgc gcggggcggc gagcacgcgc gcgcgcgcac ccccgggcag cctgggcggc    420

cgctcctgcc tgtcactgct gcggcgctgc tggtcggtcg tttcccttga aggcagcagc    480

ggaggcggcg gctgctccag acacctgcgg cggcgacccc ccggcggcgc ggagatgtgg    540

cccttggcgg cggcgctgtt gctgggctcc tgctgctgcg gttcagctca actactgttt    600

aataaaacaa aatctgtaga attcacgttt tgtaatgaca ctgtcgtcat tccatgcttt    660

gttactaata tggaggcaca aaacactact gaagtatacg taaagtggaa atttaaagga    720

agagatatct acacctttga tggagctcta aacaagtcca ctgtccccac tgactttagt    780

agtgcaaaaa ttgaagtctc acaattacta aaaggagatg cctctttgaa gatggataag    840

agtgatgctg tctcacacac aggaaactac acttgtgaag taacagaatt aaccagagaa    900

ggtgaaacga tcatagagct gaaaaaccgc acggccttca acactgacca aggatcagcc    960

tgttcttacg aggaggagaa aggaggttgc aaattagttt cgtggttttc tccaaatgaa   1020

aagatcctca ttgttatttt cccaattttg gctatactcc tgttctgggg aaagtttggt   1080

attttaacac tcaaatataa atccagccat acgaataaga gaatcattct gctgctcgtt   1140

gccgggctgg tgctcacagt catcgtggtt gttggagcca tccttctcat cccaggagaa   1200

aagcccgtga agaatgcttc tggacttggc ctcattgtaa tctctacggg gatattaata   1260

ctacttcagt acaatgtgtt tatgacagct tttggaatga cctctttcac cattgccata   1320

ttgatcactc aagtgctggg ctacgtcctt gctttggtcg ggctgtgtct ctgcatcatg   1380

gcatgtgagc cagtgcacgg cccccttttg atttcaggtt tggggatcat agctctagca   1440

gaactacttg gattagttta tatgaagttt gtcgcttcca accagaggac tatccaacct   1500

cctaggaaag ctgtagagga accccttaac gaataggtga agggaagtga cggactgtaa   1560

cttggaagtc agaaatggaa gaatacagtt gtctaagcac caggtcttca cgactcacag   1620

ctggaaggaa cagacaacag taactgactt ccatccagga aaacatgtca cataaatgat   1680

tactaagttt atattcaaag cagctgtact ttacataata aaaaaaatat gatgtgctgt   1740

gtaaccaatt ggaatcccat ttttctattg tttctactca actaggggca aacgtttcag   1800

gggcaacttc caagaatgat gcttgttaga tcctagagtc tctgaacact gagtttaaat   1860
```

```
tgattccgag tgagactcgc caagcactaa cctgagggtt agttacccag agatacctat   1920
gaaaaacagt ggtatccagc aagccttagt aaactcaggt tgccagcagc tttgccactt   1980
ccgctgctag ctgaataaca agactgccac ttctgggtca tagtgataga gactgaagta   2040
gaaaaacgaa tgtggttggg caaatcccgt gtggcccctc tgtgtgctat gatattgatg   2100
gcactggtgt cttcattctt gggggttgcc atcattcaca cacacccctt tgacatacag   2160
tgcaccccag ttttgaatac attttttttg caccctgtcc cgttctgcta ctttgatttg   2220
cgttatgata tatatatata tatataatac cttttctcct ctttaaacat ggtcctgtga   2280
cacaatagtc agttgcagaa aggagccaga cttattcgca aagcactgtg ctcaaactct   2340
tcagaaaaaa aggaaaaaaa aaaaaagcta tagttgtaac atatgtattc cagacctctg   2400
gtttaaaggc aaaagaaaaa aaatctacag tgtttcttct catgttttct gatcggaggc   2460
atgacaaagc aagactgaaa tctgaactgt gtctcctgca tggcaacacg tgtctccgtc   2520
aggccctcgc aaggcccggg gagggggttc tacgcctctt gtctctttgt tgcatgctga   2580
acactcatcg ccttcctact gtatcctgcc tcctgcagcc tccctcttcc tcctcctctt   2640
cctcttcctc ctcttcctcc tcctcctcct cttcctccaa gtttgaaagg tcaaacaaaa   2700
ctaccacatt ccctacccag ttagaagaaa accaccgtcc tgacagttgt gatcgcatgg   2760
agtactttta gattattagc acctgttttt acctcgtttg tgggcgtgtt tgtatgtgca   2820
catgtatgaa gtcggcacat gcaccttctg tatgggcaga ggcgtggcat ctacagaaga   2880
gcagatgcca actttgtgct tttagtgaat acattaaaaa aaaaaaacca acggtcctta   2940
ttgagtggaa ttctatttga tgcaaatatt tgagctcttt aagactttaa aactagataa   3000
tgtgccaagc ttttaggact gctcaccagt gccctctgaa gaaacaccag tacttttttcc  3060
tgtttgtgta ataaaggcat atttgta                                       3087
```

<210> SEQ ID NO 71
<211> LENGTH: 3030
<212> TYPE: DNA
<213> ORGANISM: Artificial
<220> FEATURE:
<223> OTHER INFORMATION: Homo sapiens and Mus musculus

<400> SEQUENCE: 71

```
tggtgaaagc agaagcagcg cctacaccgg gagagcaggg aggaggagtt ggactgaggt     60
tgggcggctc cgaggtccag ggcgagcttg gccagaggga gtagagagca gcggggctgc    120
gcagggacgc gtgccgtgag ttccggtgag cgtgtgtgtc ccatgctccc gtctttcagg    180
ccggcccagg acacgaagcc ggaagagagc tggctggagg gacgggggcc gtgagcagag    240
agtgcaaccc gcgcagcccc ggggacaggc tgattcttgg cgctctccgc cggagcctgc    300
ccagggctgg gtgtgaggct ggcgtcacgt caacgagcag aggcggccag gcggggcgga    360
gtgcgcgtgc gcggggcggc gagcacgcgc gcgcgcgcac ccccgggcag cctgggcggc    420
cgctcctgcc tgtcactgct gcggcgctgc tggtcggtcg tttcccttga aggcagcagc    480
ggaggcggcg gctgctccag acacctgcgg cggcgacccc ccggcggcgc ggagatgtgg    540
cccttggcgg cggcgctgtt gctgggctcc tgctgctgcg gttcagctca actactgttt    600
aataaaacaa aatctgtaga attcacgttt tgtaatgaca ctgtcgtcat tccatgcttt    660
gttactaata tggaggcaca aaacactact gaagtatacg taaagtggaa atttaaagga    720
agagatatct acacctttga tggagctcta aacaagtcca ctgtccccac tgactttagt    780
agtgcaaaaa ttgaagtctc acaattacta aaaggagatg cctctttgaa gatggataag    840
```

```
agtgatgctg tctcacacac aggaaactac acttgtgaag taacagaatt aaccagagaa    900
ggtgaaacga tcatagagct gaaaaaccgc acggccttca acactgacca aggatcagcc    960
tgttcttacg aggaggagaa aggaggttgc aaattagttt cgtggttttc tccaaatgaa   1020
aagatcctca ttgttatttt cccaattttg gctatactcc tgttctgggg aaagtttggt   1080
attttaacac tcaaatataa atccagccat acgaataaga gaatcattct gctgctcgtt   1140
gccgggctgg tgctcacagt catcgtggtt gttggagcca tccttctcat cccaggagaa   1200
aagcccgtga agaatgcttc tggacttggc ctcattgtaa tctctacggg gatattaata   1260
ctacttcagt acaatgtgtt tatgacagct tttggaatga cctctttcac cattgccata   1320
ttgatcactc aagtgctggg ctacgtcctt gctttggtcg ggctgtgtct ctgcatcatg   1380
gcatgtgagc cagtgcacgg ccccctttg atttcaggtt tggggatcat agctctagca    1440
gaactacttg gattagttta tatgaagttt gtcgaatagg tgaagggaag tgacggactg   1500
taacttggaa gtcagaaatg gaagaataca gttgtctaag caccaggtct tcacgactca   1560
cagctggaag gaacagacaa cagtaactga cttccatcca ggaaaacatg tcacataaat   1620
gattactaag tttatattca aagcagctgt actttacata ataaaaaaaa tatgatgtgc   1680
tgtgtaacca attggaatcc catttttcta ttgtttctac tcaactaggg gcaaacgttt   1740
caggggcaac ttccaagaat gatgcttgtt agatcctaga gtctctgaac actgagttta   1800
aattgattcc gagtgagact cgccaagcac taacctgagg gttagttacc cagagatacc   1860
tatgaaaaac agtggtatcc agcaagcctt agtaaactca ggttgccagc agctttgcca   1920
cttccgctgc tagctgaata acaagactgc cacttctggg tcatagtgat agagactgaa   1980
gtagaaaaac gaatgtggtt gggcaaatcc cgtgtggccc ctctgtgtgc tatgatattg   2040
atggcactgg tgtcttcatt cttgggggtt gccatcattc acacacaccc ctttgacata   2100
cagtgcaccc cagttttgaa tacatttttt ttgcaccctg tcccgttctg ctactttgat   2160
ttgcgttatg atatatatat atatatataa taccttttct cctctttaaa catggtcctg   2220
tgacacaata gtcagttgca gaaaggagcc agacttattc gcaaagcact gtgctcaaac   2280
tcttcagaaa aaaaggaaaa aaaaaaaaag ctatagttgt aacatatgta ttccagacct   2340
ctggtttaaa ggcaaaagaa aaaaaatcta cagtgtttct tctcatgttt tctgatcgga   2400
ggcatgacaa agcaagactg aaatctgaac tgtgtctcct gcatggcaac acgtgtctcc   2460
gtcaggccct cgcaaggccc ggggaggggg ttctacgcct cttgtctctt tgttgcatgc   2520
tgaacactca tcgccttcct actgtatcct gcctcctgca gcctccctct tcctcctcct   2580
cttcctcttc ctcctcttcc tcctcctcct cctcttcctc caagtttgaa aggtcaaaca   2640
aaactaccac attccctacc cagttagaag aaaaccaccg tcctgacagt tgtgatcgca   2700
tggagtactt ttagattatt agcacctgtt tttacctcgt ttgtgggcgt gtttgtatgt   2760
gcacatgtat gaagtcggca catgcacctt ctgtatgggc agaggcgtgg catctacaga   2820
agagcagatg ccaactttgt gcttttagtg aatacattaa aaaaaaaaaa ccaacggtcc   2880
ttattgagtg gaattctatt tgatgcaaat atttgagctc tttaagactt taaaactaga   2940
taatgtgcca agcttttagg actgctcacc agtgccctct gaagaaacac cagtactttt   3000
tcctgtttgt gtaataaagg catatttgta                                    3030
```

<210> SEQ ID NO 72
<211> LENGTH: 3057
<212> TYPE: DNA

<213> ORGANISM: Artificial
<220> FEATURE:
<223> OTHER INFORMATION: Homo sapiens and Mus musculus

<400> SEQUENCE: 72
tggtgaaagc agaagcagcg cctacaccgg gagagcaggg aggaggagtt ggactgaggt 60
tgggcggctc cgaggtccag ggcgagcttg gccagaggga gtagagagca gcggggctgc 120
gcagggacgc gtgccgtgag ttccggtgag cgtgtgtgtc ccatgctccc gtctttcagg 180
ccggcccagg acacgaagcc ggaagagagc tggctggagg gacgggggcc gtgagcagag 240
agtgcaaccc gcgcagcccc ggggacaggc tgattcttgg cgctctccgc cggagcctgc 300
ccagggctgg gtgtgaggct ggcgtcacgt caacgagcag aggcggccag gcggggcgga 360
gtgcgcgtgc gcggggcggc gagcacgcgc gcgcgcgcac ccccgggcag cctgggcggc 420
cgctcctgcc tgtcactgct gcggcgctgc tggtcggtcg tttcccttga aggcagcagc 480
ggaggcggcg gctgctccag acacctgcgg cggcgacccc ccggcggcgc ggagatgtgg 540
cccttggcgg cggcgctgtt gctgggctcc tgctgctgcg gttcagctca actactgttt 600
aataaaacaa aatctgtaga attcacgttt tgtaatgaca ctgtcgtcat tccatgcttt 660
gttactaata tggaggcaca aaacactact gaagtatacg taaagtggaa atttaaagga 720
agagatatct acacctttga tggagctcta aacaagtcca ctgtccccac tgactttagt 780
agtgcaaaaa ttgaagtctc acaattacta aaaggagatg cctctttgaa gatggataag 840
agtgatgctg tctcacacac aggaaactac acttgtgaag taacagaatt aaccagagaa 900
ggtgaaacga tcatagagct gaaaaaccgc acggtttcgt ggttttctcc aaatgaaaag 960
atcctcattg ttattttccc aattttggct atactcctgt tctggggaaa gtttggtatt 1020
ttaacactca aatataaatc cagccatacg aataagagaa tcattctgct gctcgttgcc 1080
gggctggtgc tcacagtcat cgtggttgtt ggagccatcc ttctcatccc aggagaaaag 1140
cccgtgaaga atgcttctgg acttggcctc attgtaatct ctacggggat attaatacta 1200
cttcagtaca atgtgtttat gacagctttt ggaatgacct ctttcaccat tgccatattg 1260
atcactcaag tgctgggcta cgtccttgct ttggtcgggc tgtgtctctg catcatggca 1320
tgtgagccag tgcacggccc ccttttgatt tcaggtttgg ggatcatagc tctagcagaa 1380
ctacttggat tagtttatat gaagtttgtc gcttccaacc agaggactat ccaacctcct 1440
aggaaagctg tagaggaacc ccttaacgca tttaaagagt caaaaggaat gatgaatgac 1500
gaataggtga agggaagtga cggactgtaa cttggaagtc agaaatggaa gaatacagtt 1560
gtctaagcac caggtcttca cgactcacag ctggaaggaa cagacaacag taactgactt 1620
ccatccagga aaacatgtca cataaatgat tactaagttt atattcaaag cagctgtact 1680
ttacataata aaaaaaatat gatgtgctgt gtaaccaatt ggaatcccat ttttctattg 1740
tttctactca actaggggca aacgtttcag gggcaacttc caagaatgat gcttgttaga 1800
tcctagagtc tctgaacact gagtttaaat tgattccgag tgagactcgc caagcactaa 1860
cctgagggtt agttacccag agatacctat gaaaaacagt ggtatccagc aagccttagt 1920
aaactcaggt tgccagcagc tttgccactt ccgctgctag ctgaataaca agactgccac 1980
ttctgggtca tagtgataga gactgaagta gaaaaacgaa tgtggttggg caaatcccgt 2040
gtggcccctc tgtgtgctat gatattgatg gcactggtgt cttcattctt gggggttgcc 2100
atcattcaca cacacccctt tgacatacag tgcaccccag ttttgaatac attttttttg 2160
caccctgtcc cgttctgcta ctttgatttg cgttatgata tatatatata tatataatac 2220

```
cttttctcct ctttaaacat ggtcctgtga cacaatagtc agttgcagaa aggagccaga   2280

cttattcgca aagcactgtg ctcaaactct tcagaaaaaa aggaaaaaaa aaaaaagcta   2340

tagttgtaac atatgtattc cagacctctg gtttaaaggc aaaagaaaaa aaatctacag   2400

tgtttcttct catgttttct gatcggaggc atgacaaagc aagactgaaa tctgaactgt   2460

gtctcctgca tggcaacacg tgtctccgtc aggccctcgc aaggcccggg gagggggttc   2520

tacgcctctt gtctctttgt tgcatgctga acactcatcg ccttcctact gtatcctgcc   2580

tcctgcagcc tccctcttcc tcctcctctt cctcttcctc ctcttcctcc tcctcctcct   2640

cttcctccaa gtttgaaagg tcaaacaaaa ctaccacatt ccctacccag ttagaagaaa   2700

accaccgtcc tgacagttgt gatcgcatgg agtactttta gattattagc acctgttttt   2760

acctcgtttg tgggcgtgtt tgtatgtgca catgtatgaa gtcggcacat gcaccttctg   2820

tatgggcaga ggcgtggcat ctacagaaga gcagatgcca actttgtgct tttagtgaat   2880

acattaaaaa aaaaaaacca acggtcctta ttgagtggaa ttctatttga tgcaaatatt   2940

tgagctcttt aagactttaa aactagataa tgtgccaagc ttttaggact gctcaccagt   3000

gccctctgaa gaaacaccag tactttttcc tgtttgtgta ataaaggcat atttgta      3057
```

<210> SEQ ID NO 73
<211> LENGTH: 2999
<212> TYPE: DNA
<213> ORGANISM: Artificial
<220> FEATURE:
<223> OTHER INFORMATION: Homo sapiens and Mus musculus

<400> SEQUENCE: 73

```
tggtgaaagc agaagcagcg cctacaccgg gagagcaggg aggaggagtt ggactgaggt     60

tgggcggctc cgaggtccag ggcgagcttg gccagaggga gtagagagca gcggggctgc    120

gcagggacgc gtgccgtgag ttccggtgag cgtgtgtgtc ccatgctccc gtctttcagg    180

ccggcccagg acacgaagcc ggaagagagc tggctggagg gacgggggcc gtgagcagag    240

agtgcaaccc gcgcagcccc ggggacaggc tgattcttgg cgctctccgc cggagcctgc    300

ccagggctgg gtgtgaggct ggcgtcacgt caacgagcag aggcggccag gcggggcgga    360

gtgcgcgtgc gcggggcggc gagcacgcgc gcgcgcgcac ccccgggcag cctgggcggc    420

cgctcctgcc tgtcactgct gcggcgctgc tggtcggtcg tttcccttga aggcagcagc    480

ggaggcggcg gctgctccag acacctgcgg cggcgacccc ccggcggcgc ggagatgtgg    540

cccttggcgg cggcgctgtt gctgggctcc tgctgctgcg gttcagctca actactgttt    600

aataaaacaa aatctgtaga attcacgttt tgtaatgaca ctgtcgtcat tccatgcttt    660

gttactaata tggaggcaca aaacactact gaagtatacg taaagtggaa atttaaagga    720

agagatatct acacctttga tggagctcta aacaagtcca ctgtccccac tgactttagt    780

agtgcaaaaa ttgaagtctc acaattacta aaaggagatg cctctttgaa gatggataag    840

agtgatgctg tctcacacac aggaaactac acttgtgaag taacagaatt aaccagagaa    900

ggtgaaacga tcatagagct gaaaaaccgc acggtttcgt ggttttctcc aaatgaaaag    960

atcctcattg ttattttccc aattttggct atactcctgt tctggggaaa gtttggtatt   1020

ttaacactca aatataaatc cagccatacg aataagagaa tcattctgct gctcgttgcc   1080

gggctggtgc tcacagtcat cgtggttgtt ggagccatcc ttctcatccc aggagaaaag   1140

cccgtgaaga atgcttctgg acttggcctc attgtaatct ctacggggat attaatacta   1200
```

```
cttcagtaca atgtgtttat gacagctttt ggaatgacct ctttcaccat tgccatattg   1260
atcactcaag tgctgggcta cgtccttgct ttggtcgggc tgtgtctctg catcatggca   1320
tgtgagccag tgcacggccc ccttttgatt tcaggtttgg ggatcatagc tctagcagaa   1380
ctacttggat tagtttatat gaagtttgtc gcttccaacc agaggactat ccaacctcct   1440
aggaataggt gaagggaagt gacggactgt aacttggaag tcagaaatgg aagaatacag   1500
ttgtctaagc accaggtctt cacgactcac agctggaagg aacagacaac agtaactgac   1560
ttccatccag gaaaacatgt cacataaatg attactaagt ttatattcaa agcagctgta   1620
ctttacataa taaaaaaaat atgatgtgct gtgtaaccaa ttggaatccc atttttctat   1680
tgtttctact caactagggg caaacgtttc aggggcaact tccaagaatg atgcttgtta   1740
gatcctagag tctctgaaca ctgagtttaa attgattccg agtgagactc gccaagcact   1800
aacctgaggg ttagttaccc agagatacct atgaaaaaca gtggtatcca gcaagcctta   1860
gtaaactcag gttgccagca gctttgccac ttccgctgct agctgaataa caagactgcc   1920
acttctgggt catagtgata gagactgaag tagaaaaacg aatgtggttg ggcaaatccc   1980
gtgtggcccc tctgtgtgct atgatattga tggcactggt gtcttcattc ttgggggttg   2040
ccatcattca cacacacccc tttgacatac agtgcacccc agttttgaat acattttttt   2100
tgcaccctgt cccgttctgc tactttgatt tgcgttatga tatatatata tatatataat   2160
accttttctc ctctttaaac atggtcctgt gacacaatag tcagttgcag aaaggagcca   2220
gacttattcg caaagcactg tgctcaaact cttcagaaaa aaaggaaaaa aaaaaaaagc   2280
tatagttgta acatatgtat tccagacctc tggtttaaag gcaaaagaaa aaaaatctac   2340
agtgtttctt ctcatgtttt ctgatcggag gcatgacaaa gcaagactga aatctgaact   2400
gtgtctcctg catggcaaca cgtgtctccg tcaggccctc gcaaggcccg gggagggggt   2460
tctacgcctc ttgtctcttt gttgcatgct gaacactcat cgccttccta ctgtatcctg   2520
cctcctgcag cctccctctt cctcctcctc ttcctcttcc tcctcttcct cctcctcctc   2580
ctcttcctcc aagtttgaaa ggtcaaacaa aactaccaca ttccctaccc agttagaaga   2640
aaaccaccgt cctgacagtt gtgatcgcat ggagtacttt tagattatta gcacctgttt   2700
ttacctcgtt tgtgggcgtg tttgtatgtg cacatgtatg aagtcggcac atgcaccttc   2760
tgtatgggca gaggcgtggc atctacagaa gagcagatgc caactttgtg cttttagtga   2820
atacattaaa aaaaaaaaac caacggtcct tattgagtgg aattctattt gatgcaaata   2880
tttgagctct ttaagacttt aaaactagat aatgtgccaa gcttttagga ctgctcacca   2940
gtgccctctg aagaaacacc agtacttttt cctgtttgtg taataaaggc atatttgta    2999
```

```
<210> SEQ ID NO 74
<211> LENGTH: 326
<212> TYPE: PRT
<213> ORGANISM: Artificial
<220> FEATURE:
<223> OTHER INFORMATION: Homo sapiens and Mus musculus

<400> SEQUENCE: 74

Met Trp Pro Leu Ala Ala Ala Leu Leu Leu Gly Ser Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45
```

```
Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Ala Phe Asn Thr Asp Gln Gly Ser Ala Cys Ser
    130                 135                 140

Tyr Glu Glu Glu Lys Gly Gly Cys Lys Leu Val Ser Trp Phe Ser Pro
145                 150                 155                 160

Asn Glu Lys Ile Leu Ile Val Ile Phe Pro Ile Leu Ala Ile Leu Leu
                165                 170                 175

Phe Trp Gly Lys Phe Gly Ile Leu Thr Leu Lys Tyr Lys Ser Ser His
            180                 185                 190

Thr Asn Lys Arg Ile Ile Leu Leu Leu Val Ala Gly Leu Val Leu Thr
        195                 200                 205

Val Ile Val Val Val Gly Ala Ile Leu Leu Ile Pro Gly Glu Lys Pro
    210                 215                 220

Val Lys Asn Ala Ser Gly Leu Gly Leu Ile Val Ile Ser Thr Gly Ile
225                 230                 235                 240

Leu Ile Leu Leu Gln Tyr Asn Val Phe Met Thr Ala Phe Gly Met Thr
                245                 250                 255

Ser Phe Thr Ile Ala Ile Leu Ile Thr Gln Val Leu Gly Tyr Val Leu
            260                 265                 270

Ala Leu Val Gly Leu Cys Leu Cys Ile Met Ala Cys Glu Pro Val His
        275                 280                 285

Gly Pro Leu Leu Ile Ser Gly Leu Gly Ile Ile Ala Leu Ala Glu Leu
    290                 295                 300

Leu Gly Leu Val Tyr Met Lys Phe Val Ala Ser Asn Gln Arg Thr Ile
305                 310                 315                 320

Gln Pro Pro Arg Asn Arg
                325


<210> SEQ ID NO 75
<211> LENGTH: 322
<212> TYPE: PRT
<213> ORGANISM: Artificial
<220> FEATURE:
<223> OTHER INFORMATION: Homo sapiens and Mus musculus

<400> SEQUENCE: 75

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80
```

```
Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Ala Phe Asn Thr Asp Gln Gly Ser Ala Cys Ser
    130                 135                 140

Tyr Glu Glu Glu Lys Gly Gly Cys Lys Leu Val Ser Trp Phe Ser Pro
145                 150                 155                 160

Asn Glu Lys Ile Leu Ile Val Ile Phe Pro Ile Leu Ala Ile Leu Leu
                165                 170                 175

Phe Trp Gly Lys Phe Gly Ile Leu Thr Leu Lys Tyr Lys Ser Ser His
            180                 185                 190

Thr Asn Lys Arg Ile Ile Leu Leu Leu Val Ala Gly Leu Val Leu Thr
        195                 200                 205

Val Ile Val Val Val Gly Ala Ile Leu Leu Ile Pro Gly Glu Lys Pro
    210                 215                 220

Val Lys Asn Ala Ser Gly Leu Gly Leu Ile Val Ile Ser Thr Gly Ile
225                 230                 235                 240

Leu Ile Leu Leu Gln Tyr Asn Val Phe Met Thr Ala Phe Gly Met Thr
                245                 250                 255

Ser Phe Thr Ile Ala Ile Leu Ile Thr Gln Val Leu Gly Tyr Val Leu
            260                 265                 270

Ala Leu Val Gly Leu Cys Leu Cys Ile Met Ala Cys Glu Pro Val His
        275                 280                 285

Gly Pro Leu Leu Ile Ser Gly Leu Gly Ile Ile Ala Leu Ala Glu Leu
    290                 295                 300

Leu Gly Leu Val Tyr Met Lys Phe Val Glu Trp Arg Glu Thr Pro Ser
305                 310                 315                 320

Val Ser


<210> SEQ ID NO 76
<211> LENGTH: 344
<212> TYPE: PRT
<213> ORGANISM: Artificial
<220> FEATURE:
<223> OTHER INFORMATION: Homo sapiens and Mus musculus

<400> SEQUENCE: 76

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
```

```
        115                 120                 125

Leu Lys Asn Arg Thr Ala Phe Asn Thr Asp Gln Gly Ser Ala Cys Ser
    130                 135                 140

Tyr Glu Glu Glu Lys Gly Gly Cys Lys Leu Val Ser Trp Phe Ser Pro
145                 150                 155                 160

Asn Glu Lys Ile Leu Ile Val Ile Phe Pro Ile Leu Ala Ile Leu Leu
                165                 170                 175

Phe Trp Gly Lys Phe Gly Ile Leu Thr Leu Lys Tyr Lys Ser Ser His
            180                 185                 190

Thr Asn Lys Arg Ile Ile Leu Leu Leu Val Ala Gly Leu Val Leu Thr
        195                 200                 205

Val Ile Val Val Val Gly Ala Ile Leu Leu Ile Pro Gly Glu Lys Pro
    210                 215                 220

Val Lys Asn Ala Ser Gly Leu Gly Leu Ile Val Ile Ser Thr Gly Ile
225                 230                 235                 240

Leu Ile Leu Leu Gln Tyr Asn Val Phe Met Thr Ala Phe Gly Met Thr
                245                 250                 255

Ser Phe Thr Ile Ala Ile Leu Ile Thr Gln Val Leu Gly Tyr Val Leu
            260                 265                 270

Ala Leu Val Gly Leu Cys Leu Cys Ile Met Ala Cys Glu Pro Val His
        275                 280                 285

Gly Pro Leu Leu Ile Ser Gly Leu Gly Ile Ile Ala Leu Ala Glu Leu
    290                 295                 300

Leu Gly Leu Val Tyr Met Lys Phe Val Ala Ser Asn Gln Arg Thr Ile
305                 310                 315                 320

Gln Pro Pro Arg Lys Ala Val Glu Glu Pro Leu Asn Ala Phe Lys Glu
                325                 330                 335

Ser Lys Gly Met Met Asn Asp Glu
            340


<210> SEQ ID NO 77
<211> LENGTH: 333
<212> TYPE: PRT
<213> ORGANISM: Artificial
<220> FEATURE:
<223> OTHER INFORMATION: Homo sapiens and Mus musculus

<400> SEQUENCE: 77

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Ala Phe Asn Thr Asp Gln Gly Ser Ala Cys Ser
```

```
    130                 135                 140

Tyr Glu Glu Glu Lys Gly Gly Cys Lys Leu Val Ser Trp Phe Ser Pro
145                 150                 155                 160

Asn Glu Lys Ile Leu Ile Val Ile Phe Pro Ile Leu Ala Ile Leu Leu
                165                 170                 175

Phe Trp Gly Lys Phe Gly Ile Leu Thr Leu Lys Tyr Lys Ser Ser His
            180                 185                 190

Thr Asn Lys Arg Ile Ile Leu Leu Leu Val Ala Gly Leu Val Leu Thr
        195                 200                 205

Val Ile Val Val Val Gly Ala Ile Leu Leu Ile Pro Gly Glu Lys Pro
    210                 215                 220

Val Lys Asn Ala Ser Gly Leu Gly Leu Ile Val Ile Ser Thr Gly Ile
225                 230                 235                 240

Leu Ile Leu Leu Gln Tyr Asn Val Phe Met Thr Ala Phe Gly Met Thr
                245                 250                 255

Ser Phe Thr Ile Ala Ile Leu Ile Thr Gln Val Leu Gly Tyr Val Leu
            260                 265                 270

Ala Leu Val Gly Leu Cys Leu Cys Ile Met Ala Cys Glu Pro Val His
        275                 280                 285

Gly Pro Leu Leu Ile Ser Gly Leu Gly Ile Ile Ala Leu Ala Glu Leu
    290                 295                 300

Leu Gly Leu Val Tyr Met Lys Phe Val Ala Ser Asn Gln Arg Thr Ile
305                 310                 315                 320

Gln Pro Pro Arg Lys Ala Val Glu Glu Pro Leu Asn Glu
                325                 330


<210> SEQ ID NO 78
<211> LENGTH: 314
<212> TYPE: PRT
<213> ORGANISM: Artificial
<220> FEATURE:
<223> OTHER INFORMATION: Homo sapiens and Mus musculus

<400> SEQUENCE: 78

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Ala Phe Asn Thr Asp Gln Gly Ser Ala Cys Ser
    130                 135                 140

Tyr Glu Glu Glu Lys Gly Gly Cys Lys Leu Val Ser Trp Phe Ser Pro
145                 150                 155                 160

Asn Glu Lys Ile Leu Ile Val Ile Phe Pro Ile Leu Ala Ile Leu Leu
```

```
                165                 170                 175

Phe Trp Gly Lys Phe Gly Ile Leu Thr Leu Lys Tyr Lys Ser Ser His
            180                 185                 190

Thr Asn Lys Arg Ile Ile Leu Leu Leu Val Ala Gly Leu Val Leu Thr
        195                 200                 205

Val Ile Val Val Val Gly Ala Ile Leu Leu Ile Pro Gly Glu Lys Pro
    210                 215                 220

Val Lys Asn Ala Ser Gly Leu Gly Leu Ile Val Ile Ser Thr Gly Ile
225                 230                 235                 240

Leu Ile Leu Leu Gln Tyr Asn Val Phe Met Thr Ala Phe Gly Met Thr
                245                 250                 255

Ser Phe Thr Ile Ala Ile Leu Ile Thr Gln Val Leu Gly Tyr Val Leu
            260                 265                 270

Ala Leu Val Gly Leu Cys Leu Cys Ile Met Ala Cys Glu Pro Val His
        275                 280                 285

Gly Pro Leu Leu Ile Ser Gly Leu Gly Ile Ile Ala Leu Ala Glu Leu
    290                 295                 300

Leu Gly Leu Val Tyr Met Lys Phe Val Glu
305                 310


<210> SEQ ID NO 79
<211> LENGTH: 323
<212> TYPE: PRT
<213> ORGANISM: Artificial
<220> FEATURE:
<223> OTHER INFORMATION: Homo sapiens and Mus musculus

<400> SEQUENCE: 79

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Val Ser Trp Phe Ser Pro Asn Glu Lys Ile Leu
    130                 135                 140

Ile Val Ile Phe Pro Ile Leu Ala Ile Leu Leu Phe Trp Gly Lys Phe
145                 150                 155                 160

Gly Ile Leu Thr Leu Lys Tyr Lys Ser Ser His Thr Asn Lys Arg Ile
                165                 170                 175

Ile Leu Leu Leu Val Ala Gly Leu Val Leu Thr Val Ile Val Val Val
            180                 185                 190

Gly Ala Ile Leu Leu Ile Pro Gly Glu Lys Pro Val Lys Asn Ala Ser
        195                 200                 205

Gly Leu Gly Leu Ile Val Ile Ser Thr Gly Ile Leu Ile Leu Leu Gln
```

```
    210                 215                 220

Tyr Asn Val Phe Met Thr Ala Phe Gly Met Thr Ser Phe Thr Ile Ala
225                 230                 235                 240

Ile Leu Ile Thr Gln Val Leu Gly Tyr Val Leu Ala Leu Val Gly Leu
                245                 250                 255

Cys Leu Cys Ile Met Ala Cys Glu Pro Val His Gly Pro Leu Leu Ile
            260                 265                 270

Ser Gly Leu Gly Ile Ile Ala Leu Ala Glu Leu Leu Gly Leu Val Tyr
        275                 280                 285

Met Lys Phe Val Ala Ser Asn Gln Arg Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu


<210> SEQ ID NO 80
<211> LENGTH: 305
<212> TYPE: PRT
<213> ORGANISM: Artificial
<220> FEATURE:
<223> OTHER INFORMATION: Homo sapiens and Mus musculus

<400> SEQUENCE: 80

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Val Ser Trp Phe Ser Pro Asn Glu Lys Ile Leu
    130                 135                 140

Ile Val Ile Phe Pro Ile Leu Ala Ile Leu Leu Phe Trp Gly Lys Phe
145                 150                 155                 160

Gly Ile Leu Thr Leu Lys Tyr Lys Ser Ser His Thr Asn Lys Arg Ile
                165                 170                 175

Ile Leu Leu Leu Val Ala Gly Leu Val Leu Thr Val Ile Val Val Val
            180                 185                 190

Gly Ala Ile Leu Leu Ile Pro Gly Glu Lys Pro Val Lys Asn Ala Ser
        195                 200                 205

Gly Leu Gly Leu Ile Val Ile Ser Thr Gly Ile Leu Ile Leu Leu Gln
    210                 215                 220

Tyr Asn Val Phe Met Thr Ala Phe Gly Met Thr Ser Phe Thr Ile Ala
225                 230                 235                 240

Ile Leu Ile Thr Gln Val Leu Gly Tyr Val Leu Ala Leu Val Gly Leu
                245                 250                 255
```

```
Cys Leu Cys Ile Met Ala Cys Glu Pro Val His Gly Pro Leu Leu Ile
            260                 265                 270

Ser Gly Leu Gly Ile Ile Ala Leu Ala Glu Leu Leu Gly Leu Val Tyr
        275                 280                 285

Met Lys Phe Val Ala Ser Asn Gln Arg Thr Ile Gln Pro Pro Arg Asn
    290                 295                 300

Arg
305


<210> SEQ ID NO 81
<211> LENGTH: 25
<212> TYPE: DNA
<213> ORGANISM: Artificial
<220> FEATURE:
<223> OTHER INFORMATION: PCR primer

<400> SEQUENCE: 81

acaaacattt cttcggtgct ttgcg                                           25


<210> SEQ ID NO 82
<211> LENGTH: 26
<212> TYPE: DNA
<213> ORGANISM: Artificial
<220> FEATURE:
<223> OTHER INFORMATION: PCR primer

<400> SEQUENCE: 82

gtcttgagtt acaggctcat gtgggg                                          26


<210> SEQ ID NO 83
<211> LENGTH: 25
<212> TYPE: DNA
<213> ORGANISM: Artificial
<220> FEATURE:
<223> OTHER INFORMATION: PCR primer

<400> SEQUENCE: 83

cgaggaacgt attctcctgc gaaac                                           25


<210> SEQ ID NO 84
<211> LENGTH: 25
<212> TYPE: DNA
<213> ORGANISM: Artificial
<220> FEATURE:
<223> OTHER INFORMATION: PCR primer

<400> SEQUENCE: 84

agctatgtgg cttagcactc tgtgc                                           25


<210> SEQ ID NO 85
<211> LENGTH: 25
<212> TYPE: DNA
<213> ORGANISM: Artificial
<220> FEATURE:
<223> OTHER INFORMATION: PCR primer

<400> SEQUENCE: 85

cttaaactcc acgtcatcgg ggctc                                           25


<210> SEQ ID NO 86
<211> LENGTH: 19
<212> TYPE: DNA
<213> ORGANISM: Artificial
<220> FEATURE:
```

-continued

```
<223> OTHER INFORMATION: PCR primer

<400> SEQUENCE: 86

ttgctgctgg ggattcgac                                                   19


<210> SEQ ID NO 87
<211> LENGTH: 22
<212> TYPE: DNA
<213> ORGANISM: Artificial
<220> FEATURE:
<223> OTHER INFORMATION: PCR primer

<400> SEQUENCE: 87

ctgctggggt gacattactg at                                               22


<210> SEQ ID NO 88
<211> LENGTH: 19
<212> TYPE: DNA
<213> ORGANISM: Artificial
<220> FEATURE:
<223> OTHER INFORMATION: PCR primer

<400> SEQUENCE: 88

cctgacaagt ccgtgttgg                                                   19


<210> SEQ ID NO 89
<211> LENGTH: 21
<212> TYPE: DNA
<213> ORGANISM: Artificial
<220> FEATURE:
<223> OTHER INFORMATION: PCR primer

<400> SEQUENCE: 89

ctcctctgaa ccactggatg g                                                21
```